US012708566B2

(12) United States Patent
van der Leest et al.

(10) Patent No.: US 12,708,566 B2
(45) Date of Patent: Aug. 18, 2026

(54) NEGATIVE PRESSURE WOUND THERAPY (NPWT) BANDAGE

(71) Applicant: Guard Medical SAS, Paris (FR)

(72) Inventors: Machiel van der Leest, Paris (FR); John Frederick Cornhill, Fort Lauderdale, FL (US); Russell Corwin, Elmsford, NY (US)

(73) Assignee: Stryker Corporation, Portage, MI (US)

( * ) Notice: Subject to any disclaimer, the term of this patent is extended or adjusted under 35 U.S.C. 154(b) by 0 days.

(21) Appl. No.: 17/771,166

(22) PCT Filed: Oct. 22, 2020

(86) PCT No.: PCT/US2020/056871

§ 371 (c)(1),
(2) Date: Apr. 22, 2022

(87) PCT Pub. No.: WO2021/081210

PCT Pub. Date: Apr. 29, 2021

(65) Prior Publication Data

US 2022/0378623 A1 Dec. 1, 2022

Related U.S. Application Data

(60) Provisional application No. 63/081,690, filed on Sep. 22, 2020, provisional application No. 62/992,667, (Continued)

(51) Int. Cl.

| | |
|---|---|
| *A61F 13/05* | (2024.01) |
| *A61F 13/0206* | (2024.01) |

(Continued)

(52) U.S. Cl.

CPC .......... *A61F 13/05* (2024.01); *A61F 13/0206* (2013.01); *A61M 1/7415* (2021.05); *A61M 1/962* (2021.05); *A61M 39/24* (2013.01)

(58) Field of Classification Search

CPC ...... A61M 1/74; A61M 1/742; A61M 1/7413; A61M 1/7415; A61M 1/743; A61M 1/962;

(Continued)

(56) References Cited

U.S. PATENT DOCUMENTS

| | | |
|---|---|---|
| 3,486,504 A | 12/1969 | Austin, Jr. |
| 3,874,387 A | 4/1975 | Barbieri |

(Continued)

FOREIGN PATENT DOCUMENTS

| | | |
|---|---|---|
| CN | 105457110 W | 4/2016 |
| EP | 3695819 | 8/2020 |

(Continued)

OTHER PUBLICATIONS

Argenta et al., Vacuum-Assisted Closure: A New Method for Wound Control and Treatment: Clinical Experience, Annals of Plastic Surgery, Jun. 1997, vol. 38, No. 6, 563-577.

(Continued)

*Primary Examiner* — Philip R Wiest
*Assistant Examiner* — Seth Han
(74) *Attorney, Agent, or Firm* — McDonnell Boehnen Hulbert & Berghoff LLP

(57) ABSTRACT

A negative pressure wound therapy bandage for applying negative pressure to a wound, the bandage comprising: a membrane configured for disposition over a wound so as to form a wound chamber between the membrane and the wound, the membrane comprising a wound-side surface, an atmosphere-side surface, and an opening extending through the membrane from the wound-side surface to the atmosphere-side surface; and a pump assembly carried by the membrane, the pump assembly comprising: a pump body comprising a wall structure disposed about a pump chamber, wherein at least a portion of the wall structure is resilient, (Continued)

and further wherein the pump chamber communicates with the wound chamber through the opening formed in the membrane; and an atmosphere-side passageway extending through the wall structure so as to fluidically connect the pump chamber to the atmosphere.

16 Claims, 50 Drawing Sheets

Related U.S. Application Data filed on Mar. 20, 2020, provisional application No. 62/924,290, filed on Oct. 22, 2019, provisional application No. 62/924,432, filed on Oct. 22, 2019, provisional application No. 62/924,386, filed on Oct. 22, 2019.

(51) Int. Cl.
*A61M 1/00* (2006.01)
*A61M 39/24* (2006.01)

(58) Field of Classification Search
CPC .......... A61M 1/82; A61M 1/912; A61M 1/96; A61M 1/915; A61M 1/68; A61M 1/682; A61M 1/684; A61F 13/00068
See application file for complete search history.

(56) References Cited

U.S. PATENT DOCUMENTS

| | | | | | |
|---|---|---|---|---|---|
| 3,938,514 | A | | 2/1976 | Boucher | |
| 4,073,294 | A | | 2/1978 | Stanley et al. | |
| 4,341,208 | A | | 7/1982 | Gordon et al. | |
| 4,429,693 | A | * | 2/1984 | Blake | A61M 1/68 604/319 |
| 4,465,062 | A | | 8/1984 | Versaggi et al. | |
| 4,614,183 | A | | 9/1986 | McCracken et al. | |
| 4,664,106 | A | | 5/1987 | Snedeker | |
| 4,997,438 | A | | 3/1991 | Nipper | |
| 5,263,922 | A | | 11/1993 | Sova et al. | |
| 5,437,622 | A | | 8/1995 | Carion | |
| 5,454,779 | A | | 10/1995 | Lurie et al. | |
| 5,478,333 | A | | 12/1995 | Asherman, Jr. | |
| 5,549,584 | A | | 8/1996 | Gross | |
| 5,562,107 | A | | 10/1996 | Lavender et al. | |
| 5,589,256 | A | | 12/1996 | Hansen et al. | |
| 5,599,289 | A | | 2/1997 | Castellena | |
| 5,636,643 | A | | 6/1997 | Argenta et al. | |
| 5,645,081 | A | | 7/1997 | Argenta et al. | |
| 5,788,463 | A | | 8/1998 | Chan | |
| 5,848,993 | A | * | 12/1998 | Tanhehco | A61M 1/682 D24/115 |
| 6,008,429 | A | | 12/1999 | Ritger | |
| 6,431,212 | B1 | | 8/2002 | Hayenga et al. | |
| 6,436,432 | B2 | | 8/2002 | Heinecke et al. | |
| 6,936,037 | B2 | | 8/2005 | Bubb et al. | |
| 6,951,553 | B2 | | 10/2005 | Bubb et al. | |
| 7,070,584 | B2 | | 7/2006 | Johnson et al. | |
| 7,290,660 | B2 | | 11/2007 | Tilman et al. | |
| 7,338,482 | B2 | | 3/2008 | Lockwood et al. | |
| 7,534,039 | B2 | | 5/2009 | Wu | |
| 7,569,742 | B2 | | 8/2009 | Haggstrom et al. | |
| 7,699,823 | B2 | | 4/2010 | Haggstrom et al. | |
| 7,763,769 | B2 | | 7/2010 | Johnson et al. | |
| 7,779,625 | B2 | | 8/2010 | Joshi et al. | |
| 7,790,945 | B1 | | 9/2010 | Watson, Jr. | |
| 7,794,438 | B2 | | 9/2010 | Henley et al. | |
| 7,838,717 | B2 | | 11/2010 | Haggstrom et al. | |
| 7,874,731 | B2 | | 1/2011 | Turvey et al. | |
| 7,886,746 | B2 | | 2/2011 | Heaton et al. | |
| 7,909,805 | B2 | | 3/2011 | Weston | |
| 7,942,866 | B2 | | 5/2011 | Radl et al. | |
| 7,951,100 | B2 | | 5/2011 | Hunt et al. | |
| 7,964,766 | B2 | | 6/2011 | Blott et al. | |
| 8,084,664 | B2 | | 12/2011 | Johnson et al. | |
| 8,187,210 | B2 | | 5/2012 | Hunt et al. | |
| 8,188,331 | B2 | | 5/2012 | Barta et al. | |
| 8,202,002 | B2 | | 6/2012 | McMahon et al. | |
| 8,207,392 | B2 | | 6/2012 | Haggstrom et al. | |
| 8,212,100 | B2 | | 7/2012 | Moore | |
| 8,257,326 | B2 | | 9/2012 | Vitaris | |
| 8,337,474 | B2 | | 12/2012 | Hu et al. | |
| 8,353,928 | B2 | | 1/2013 | Joshi | |
| 8,439,894 | B1 | | 5/2013 | Miller | |
| 8,460,255 | B2 | | 6/2013 | Joshi et al. | |
| 8,460,257 | B2 | | 6/2013 | Locke et al. | |
| 8,535,283 | B2 | | 9/2013 | Heaton et al. | |
| 8,545,466 | B2 | | 10/2013 | Andresen et al. | |
| 8,545,469 | B2 | | 10/2013 | Andresen et al. | |
| 8,569,566 | B2 | | 10/2013 | Blott et al. | |
| 8,604,265 | B2 | | 12/2013 | Locke et al. | |
| 8,632,523 | B2 | | 1/2014 | Eriksson et al. | |
| 8,679,079 | B2 | | 3/2014 | Heaton et al. | |
| 8,680,360 | B2 | | 3/2014 | Greener et al. | |
| 8,735,644 | B2 | | 5/2014 | Johnson et al. | |
| 8,764,732 | B2 | | 7/2014 | Hartwell | |
| 8,771,244 | B2 | | 7/2014 | Eckstein et al. | |
| 8,829,263 | B2 | | 9/2014 | Haggstrom et al. | |
| 8,961,481 | B2 | | 2/2015 | Hu et al. | |
| 9,033,942 | B2 | | 5/2015 | Vess | |
| 9,265,665 | B2 | | 2/2016 | Robinson et al. | |
| 9,302,033 | B2 | | 4/2016 | Riesinger | |
| 9,427,502 | B2 | | 8/2016 | Robinson et al. | |
| 9,427,505 | B2 | | 8/2016 | Askem et al. | |
| 9,545,465 | B2 | | 1/2017 | Allen et al. | |
| 9,561,312 | B2 | | 2/2017 | Heaton et al. | |
| 9,717,829 | B2 | | 8/2017 | Eriksson et al. | |
| 9,820,888 | B2 | | 11/2017 | Greener et al. | |
| 9,839,560 | B2 | | 12/2017 | Marcoux et al. | |
| 9,895,471 | B2 | | 2/2018 | Hu et al. | |
| 9,925,313 | B2 | | 3/2018 | Weston | |
| 9,968,488 | B2 | | 5/2018 | Zamierowski et al. | |
| 10,058,642 | B2 | | 8/2018 | Weston | |
| 10,064,984 | B2 | | 9/2018 | Locke et al. | |
| 10,123,909 | B2 | | 11/2018 | Hartwell | |
| 10,159,604 | B2 | | 12/2018 | Adie et al. | |
| 10,201,644 | B2 | | 2/2019 | Haggstrom et al. | |
| 10,426,875 | B2 | | 10/2019 | Blott et al. | |
| 10,485,907 | B2 | | 11/2019 | Huang | |
| 10,493,184 | B2 | | 12/2019 | Collinson et al. | |
| 10,548,776 | B2 | | 2/2020 | Greener et al. | |
| 10,610,414 | B2 | | 4/2020 | Hartwell et al. | |
| 10,653,823 | B2 | | 5/2020 | Bharti et al. | |
| 10,758,651 | B2 | | 9/2020 | Blott et al. | |
| 10,842,919 | B2 | | 11/2020 | Weston | |
| 11,071,653 | B2 | | 7/2021 | Hunt | |
| 11,110,010 | B2 | | 9/2021 | Hartwell | |
| 11,129,751 | B2 | | 9/2021 | Hartwell | |
| 11,179,276 | B2 | | 11/2021 | Hartwell | |
| 11,229,555 | B2 | | 1/2022 | Eaves, III | |
| 11,246,975 | B2 | | 2/2022 | Locke et al. | |
| 11,324,639 | B2 | | 5/2022 | Daich et al. | |
| 11,351,064 | B2 | | 6/2022 | Hartwell | |
| 11,433,176 | B2 | | 9/2022 | Hall et al. | |
| 11,596,552 | B2 | | 3/2023 | Hartwell et al. | |
| 11,614,170 | B2 | | 3/2023 | Tumey et al. | |
| 11,717,655 | B2 | | 8/2023 | Hall et al. | |
| 11,723,809 | B2 | | 8/2023 | Askem et al. | |
| 11,806,469 | B2 | | 11/2023 | Fujisaki | |
| 11,819,385 | B2 | | 11/2023 | Sexton | |
| 11,826,236 | B2 | | 11/2023 | Bergstöm et al. | |
| 11,839,527 | B2 | * | 12/2023 | Johnson | A61M 1/962 |
| 11,903,798 | B2 | | 2/2024 | Askem et al. | |
| 12,064,579 | B2 | | 8/2024 | Hall et al. | |
| 12,121,420 | B2 | | 10/2024 | Askem et al. | |
| 2001/0029956 | A1 | | 10/2001 | Argenta et al. | |
| 2002/0111576 | A1 | | 8/2002 | Greene et al. | |
| 2003/0188754 | A1 | | 10/2003 | Heaton et al. | |
| 2004/0033750 | A1 | | 2/2004 | Everett et al. | |
| 2004/0054313 | A1 | | 3/2004 | Molan | |
| 2005/0070835 | A1 | | 3/2005 | Joshi | |
| 2005/0101940 | A1 | | 5/2005 | Radl et al. | |

(56) References Cited

U.S. PATENT DOCUMENTS

2005/0143697 A1 6/2005 Riesinger
2005/0175649 A1 8/2005 Disalvo et al.
2005/0222528 A1 10/2005 Weston
2005/0261642 A1* 11/2005 Weston ................... A61M 1/98 604/313
2006/0076069 A1 4/2006 Haamer
2006/0079852 A1 4/2006 Bubb et al.
2007/0055209 A1 3/2007 Patel et al.
2008/0003274 A1 1/2008 Kaiser
2008/0033330 A1* 2/2008 Moore ................ A61F 13/0246 602/54
2008/0108977 A1 5/2008 Heaton et al.
2008/0287892 A1 11/2008 Khan et al.
2008/0306456 A1 12/2008 Riesinger
2009/0105670 A1 4/2009 Bentley et al.
2009/0187130 A1 7/2009 Asmus et al.
2009/0281526 A1 11/2009 Kenny et al.
2009/0299256 A1 12/2009 Barta et al.
2009/0299341 A1 12/2009 Kazala, Jr. et al.
2009/0326430 A1 12/2009 Frederiksen et al.
2010/0063483 A1 3/2010 Adahan
2010/0137775 A1 6/2010 Hu et al.
2010/0160881 A1 6/2010 Lin et al.
2010/0160901 A1 6/2010 Hu et al.
2010/0191197 A1 7/2010 Braga et al.
2010/0286635 A1 11/2010 Watson, Jr.
2010/0305490 A1 12/2010 Coulthard et al.
2010/0305524 A1 12/2010 Vess et al.
2011/0087177 A2 4/2011 Weston
2011/0106030 A1 5/2011 Scholz
2011/0112492 A1 5/2011 Bharti et al.
2011/0137270 A1 6/2011 Hu et al.
2011/0196321 A1 8/2011 Wudyka
2012/0035562 A1 2/2012 Locke et al.
2012/0041401 A1 2/2012 Chao et al.
2012/0109083 A1 5/2012 Coulthard et al.
2012/0222687 A1* 9/2012 Czajka, Jr. ............ A61M 1/984 128/853
2012/0238932 A1 9/2012 Atteia et al.
2012/0316538 A1 12/2012 Heiser et al.
2013/0046223 A1 2/2013 Schrammel
2013/0085462 A1 4/2013 Nip et al.
2013/0144231 A1 6/2013 Hu et al.
2013/0209281 A1 8/2013 Locke et al.
2013/0226115 A1 8/2013 Robinson et al.
2013/0296816 A1* 11/2013 Greener .................. A61M 1/74 604/320
2013/0304007 A1 11/2013 Toth
2013/0310809 A1 11/2013 Armstrong et al.
2014/0088521 A1 3/2014 Eriksson et al.
2014/0107597 A1 4/2014 Hu et al.
2014/0171920 A1 6/2014 Smith et al.
2014/0188061 A1 7/2014 Locke et al.
2014/0221907 A1 8/2014 Scholz et al.
2014/0241922 A1 8/2014 Yang
2014/0243767 A1 8/2014 Hu et al.
2014/0276498 A1 9/2014 Connor et al.
2014/0343518 A1 11/2014 Riesinger
2015/0005722 A1 1/2015 Hu et al.
2015/0025486 A1 1/2015 Hu et al.
2015/0057625 A1 2/2015 Coulthard
2015/0141941 A1 5/2015 Allen et al.
2015/0148761 A1 5/2015 Hu et al.
2015/0174304 A1 6/2015 Askem et al.
2015/0202354 A1 7/2015 Wall
2015/0217032 A1 8/2015 Allen et al.
2015/0250931 A1 9/2015 Bharti et al.
2015/0314052 A1 11/2015 Vess
2016/0045375 A1 2/2016 Zurovcik
2016/0184495 A1 6/2016 Fouillet et al.
2016/0199230 A1 7/2016 Doshi et al.
2016/0206792 A1 7/2016 Worthley
2016/0206793 A1 7/2016 Robinson et al.
2016/0287446 A1 10/2016 Meixner et al.
2016/0361205 A1 12/2016 Mumby et al.
2017/0080133 A1 3/2017 Locke et al.
2017/0112974 A1 4/2017 Fujisaki
2017/0128272 A1 5/2017 Wu et al.
2017/0143552 A1 5/2017 Hartwell et al.
2017/0172806 A1 6/2017 Fung et al.
2017/0181894 A1 6/2017 Allen et al.
2017/0181896 A1 6/2017 Hartwell
2017/0181897 A1 6/2017 Hartwell
2017/0209312 A1 7/2017 Kanchagar et al.
2017/0246113 A1 8/2017 Blaskovich et al.
2017/0266051 A1 9/2017 Hartwell
2017/0304512 A1 10/2017 Hu et al.
2017/0367895 A1 12/2017 Holm et al.
2017/0367896 A1 12/2017 Holm et al.
2018/0021178 A1 1/2018 Locke et al.
2018/0133065 A1 5/2018 Hartwell
2018/0140466 A1 5/2018 Hunt
2018/0140753 A1 5/2018 Askem et al.
2018/0168869 A1 6/2018 Allen et al.
2018/0185629 A1* 7/2018 Luckemeyer ........... A61M 1/94
2018/0221511 A1 8/2018 Ohri et al.
2018/0228482 A1 8/2018 Madsen et al.
2018/0243463 A1 8/2018 Chatterjee et al.
2018/0272052 A1 9/2018 Locke et al.
2018/0303676 A1 10/2018 Bonn
2018/0305468 A1 10/2018 Tramontano et al.
2018/0318477 A1 11/2018 Eksteen
2018/0369460 A1 12/2018 Bonn
2019/0099171 A1 4/2019 Lichty, II et al.
2019/0117575 A1 4/2019 Blaskovich et al.
2019/0183685 A1 6/2019 McNulty et al.
2019/0184076 A1 6/2019 Gourlay
2019/0269835 A1 9/2019 Pinto et al.
2019/0282740 A1 9/2019 Luckemeyer et al.
2019/0350965 A1 11/2019 Ohri et al.
2020/0000727 A1 1/2020 Blaskovich et al.
2020/0016081 A1 1/2020 Ohri et al.
2020/0069477 A1 3/2020 Holm et al.
2020/0078225 A1 3/2020 Grillitsch et al.
2020/0078499 A1 3/2020 Gadde et al.
2020/0085349 A1 3/2020 Bremer
2020/0085626 A1 3/2020 Braga et al.
2020/0086013 A1 3/2020 Quintanar
2020/0086016 A1 3/2020 Bannister et al.
2020/0093970 A1 3/2020 Hunt et al.
2020/0100945 A1 4/2020 Albert et al.
2020/0101207 A1 4/2020 Weston et al.
2020/0107964 A1 4/2020 Locke et al.
2020/0107967 A1 4/2020 Holm et al.
2020/0108235 A1 4/2020 Locke et al.
2020/0113741 A1 4/2020 Rehbein et al.
2020/0114050 A1 4/2020 Collinson et al.
2020/0114051 A1 4/2020 Pratt et al.
2020/0121509 A1 4/2020 Locke et al.
2020/0121510 A1 4/2020 Hartwell et al.
2020/0121511 A1 4/2020 Locke et al.
2020/0121512 A1 4/2020 Locke et al.
2020/0121833 A9 4/2020 Askem et al.
2020/0129341 A1 4/2020 Coulthard et al.
2020/0129674 A1 4/2020 Moore et al.
2020/0129675 A1 4/2020 Robinson et al.
2020/0146898 A1 5/2020 Locke et al.
2020/0155356 A1 5/2020 Greener et al.
2020/0268562 A1 8/2020 Dunn
2020/0282115 A1 9/2020 Gardner et al.
2021/0046224 A1 2/2021 Blott et al.
2021/0077669 A1 3/2021 Weston
2021/0100691 A1 4/2021 Gilding et al.
2021/0169699 A1* 6/2021 Johnson ................ A61M 39/24
2022/0000672 A1 1/2022 Hunt
2022/0000673 A1 1/2022 Hartwell
2022/0176032 A1 6/2022 Randolph et al.
2022/0183895 A1 6/2022 Rehbein et al.
2022/0226162 A1 7/2022 Daich et al.
2023/0043747 A1 2/2023 Albert et al.
2023/0190533 A1 6/2023 Locke et al.
2023/0210699 A1 7/2023 Svensson et al.
2023/0225906 A1 7/2023 Johannison et al.
2023/0285200 A1 9/2023 Gardner et al.

(56) References Cited

U.S. PATENT DOCUMENTS

| | | | |
|---|---|---|---|
| 2023/0338194 | A1 | 10/2023 | Seddon et al. |
| 2024/0075199 | A1 | 3/2024 | Cotton et al. |
| 2024/0156645 | A1 | 5/2024 | Braga et al. |
| 2024/0207102 | A1 | 6/2024 | Allen et al. |

FOREIGN PATENT DOCUMENTS

| | | | | |
|---|---|---|---|---|
| EP | 3744361 | | 7/2024 | |
| EP | 4400152 | | 7/2024 | |
| EP | 3703637 | | 9/2024 | |
| GB | 2540955 | | 2/2017 | |
| WO | WO 02/087993 | | 11/2002 | |
| WO | WO 2005/051461 | | 6/2005 | |
| WO | WO 2007/068477 | W | 6/2007 | |
| WO | WO 2008/048527 | | 4/2008 | |
| WO | WO 2009/124125 | | 10/2009 | |
| WO | WO 2009/124473 | W | 10/2009 | |
| WO | WO 2010/068502 | | 6/2010 | |
| WO | WO 2010/121186 | | 10/2010 | |
| WO | WO 2011/049562 | | 4/2011 | |
| WO | WO 2011/162862 | | 12/2011 | |
| WO | WO 2012/021657 | | 2/2012 | |
| WO | WO 2012/038727 | | 3/2012 | |
| WO | WO 2012/151359 | | 11/2012 | |
| WO | WO 2013/039713 | | 3/2013 | |
| WO | WO 2014/039557 | | 3/2014 | |
| WO | WO 2014/140606 | | 9/2014 | |
| WO | WO 2014/145014 | | 9/2014 | |
| WO | WO 2015/052219 | | 4/2015 | |
| WO | WO 2015/193257 | | 12/2015 | |
| WO | WO 2016/094742 | | 6/2016 | |
| WO | WO 2016/182977 | | 11/2016 | |
| WO | WO-2016182977 | A1 * | 11/2016 | ....... A61F 13/00068 |
| WO | WO 2017/053384 | | 3/2017 | |
| WO | WO 2019/113275 | | 6/2019 | |
| WO | WO 2021/084444 | | 5/2021 | |
| WO | WO 2021/090277 | | 5/2021 | |
| WO | WO 2024/121724 | | 6/2024 | |

OTHER PUBLICATIONS

Blackburn et al., Negative-Pressure Dressings as a Bolster for Skin Grafts, Annals of Plastic Surgery, May 1998, vol. 40, No. 5, 453-457.

Genecov et al., A Controlled Subatmospheric Pressure Dressing Increases the Rate of Skin Graft Donor Site Reepithelialization, Annals of Plastic Surgery, Mar. 1998, vol. 40, No. 3, 219-225.

Molnar et al., Single-Stage Approach to Skin Grafting the Exposed Skull, Jan. 5, 1999, vol. 105, No. 1, 174-177.

Morykwas et al., Vacuum-Assisted Closure: A New Method for Wound Control and Treatment: Animal Studies and Basic Foundation, Annals of Plastic Surgery, Jun. 1997, vol. 38, No. 6, 553-562.

Muensterer et al., A Simple Vacuum Dressing Reduces the Wound Infection Rate of Single-Incision Pediatric Endosurgical Appendectomy, JSLS (2011)15:147-150.

Seifarth et al., A Simple Postoperative Umbilical Negative-Pressure Dressing. Advances in Skin & Wound Care, vol. 26, No. 1 (2013), 26-29.

Sposato et al., Ambulant vacuum-assisted closure of skin-graft dressing in the lower limbs using a portable mini-VAC device. British Journal of Plastic Surgery, (2001), 54, 235-237.

* cited by examiner

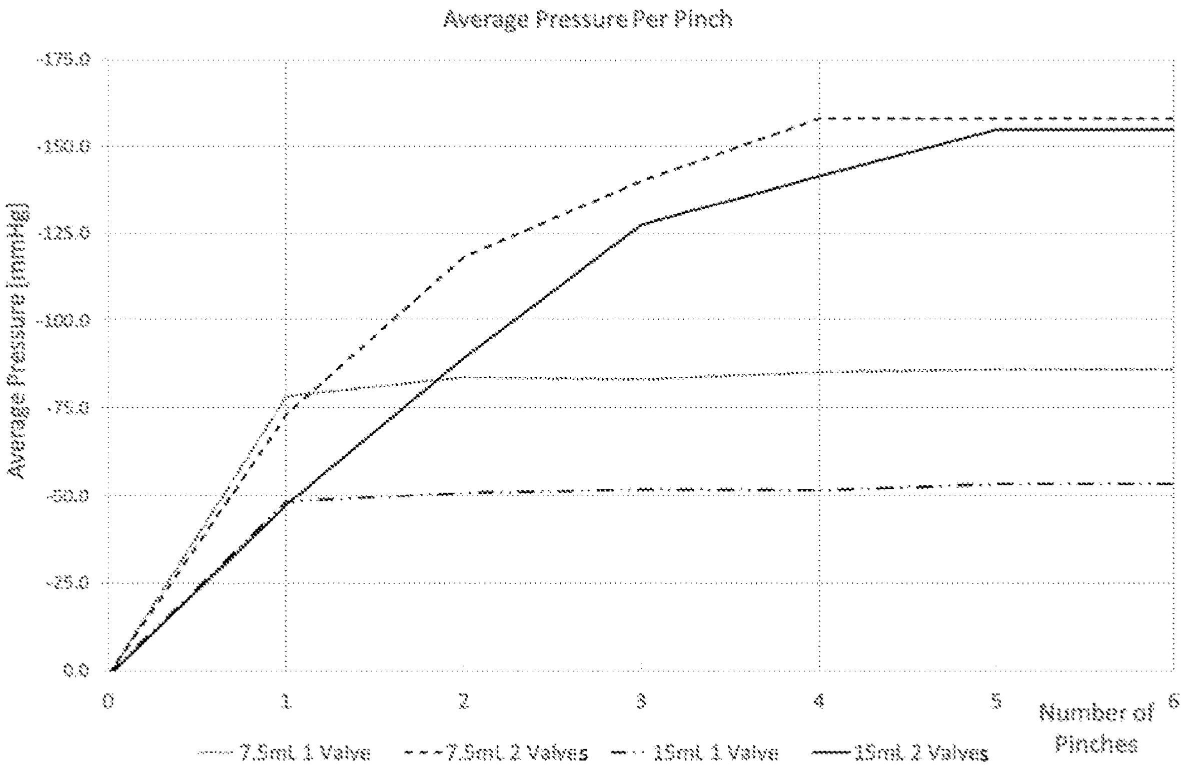

7.5 mL 1 Valve = 7.5 mL wound chamber, deformable body pump assembly with 1 one-way valve
7.5 mL 2 Valves = 7.5 mL wound chamber, deformable body pump assembly with 2 one-way valves
15 mL 1 Valve = 15 mL wound chamber, deformable body pump assembly with 1 one-way valve
15 mL 2 Valves = 15 mL wound chamber, deformable body pump assembly with 2 one-way valves Note: in the comparison shown in this figure, the volume of the pump chamber of the deformable pump body with 1 one-way valve is the same as the volume of the pump chamber of the deformable pump body with 2 one-way valves

FIG. 4A

UNBOX PRODUCT

UNWRAP PRODUCT FROM STERILE PACKAGING

PRODUCT UNPACKAGED AND READY FOR USE

REMOVE RELEASE LINER

APPLY PRODUCT TO WOUND SITE, AND REMOVE REMOVABLE STIFFENER

SQUEEZE SIDES OF PUMP TO EXPEL AIR FROM SEALED WOUND SITE

FULLY COLLAPSED PUMP BODY INDICATES NEGATIVE PRESSURE ACHIEVED

NEGATIVE PRESSURE WOUND THERAPY (NPWT) BANDAGE

REFERENCE TO PENDING PRIOR PATENT APPLICATIONS

This patent application:

(i) is a continuation-in-part of pending prior U.S. patent application Ser. No. 16/768,481, filed May 21, 2020 by Cornell University and Timothy Johnson et al. for MANUALLY-OPERATED NEGATIVE PRESSURE WOUND THERAPY (NPWT) BANDAGE WITH IMPROVED PUMP EFFICIENCY, AUTOMATIC PRESSURE INDICATOR AND AUTOMATIC PRESSURE LIMITER, which patent application:

(a) claims benefit of International (PCT) Patent Application No. PCT/US18/64178, filed Dec. 6, 2018 by Cornell University and Timothy Johnson et al. for MANUALLY-OPERATED NEGATIVE PRESSURE WOUND THERAPY (NPWT) BANDAGE WITH IMPROVED PUMP EFFICIENCY, AUTOMATIC PRESSURE INDICATOR AND AUTOMATIC PRESSURE LIMITER, which patent application in turn claims benefit of:

(1) prior U.S. Provisional Patent Application Ser. No. 62/595,398, filed Dec. 6, 2017 by Cornell University and Timothy Johnson et al. for MANUALLY-OPERATED NEGATIVE PRESSURE WOUND THERAPY (NPWT) BANDAGE WITH IMPROVED PUMP EFFICIENCY, AUTOMATIC PRESSURE INDICATOR AND AUTOMATIC PRESSURE LIMITER; and (2) prior U.S. Provisional Patent Application Ser. No. 62/611,227, filed Dec. 28, 2017 by Cornell University and Timothy Johnson et al. for MANUALLY-OPERATED NEGATIVE PRESSURE WOUND THERAPY (NPWT) BANDAGE WITH IMPROVED PUMP EFFICIENCY, AUTOMATIC PRESSURE INDICATOR AND AUTOMATIC PRESSURE LIMITER;

(ii) claims benefit of prior U.S. Provisional Patent Application Ser. No. 62/924,386, filed Oct. 22, 2019 by Guard Medical SAS and Russell Corwin et al. for MANUALLY-OPERATED NEGATIVE PRESSURE WOUND THERAPY (NPWT) BANDAGE WITH IMPROVED PUMP EFFICIENCY, AUTOMATIC PRESSURE INDICATOR AND AUTOMATIC PRESSURE LIMITER, INCLUDING NEGATIVE PRESSURE DECAY "WARNING STATE" INDICATOR;

(iii) claims benefit of prior U.S. Provisional Patent Application Ser. No. 62/924,290, filed Oct. 22, 2019 by Guard Medical SAS and Machiel van der Leest et al. for MANUALLY-OPERATED NEGATIVE PRESSURE WOUND THERAPY (NPWT) BANDAGE WITH IMPROVED PUMP EFFICIENCY, AUTOMATIC PRESSURE INDICATOR AND AUTOMATIC PRESSURE LIMITER, INCLUDING CANISTER FOR COLLECTING EXUDATES;

(iv) claims benefit of prior U.S. Provisional Patent Application Ser. No. 62/924,432, filed Oct. 22, 2019 by Guard Medical SAS and Machiel van der Leest et al. for MANUALLY-OPERATED NEGATIVE PRESSURE WOUND THERAPY (NPWT) BANDAGE WITH IMPROVED PUMP EFFICIENCY, AUTOMATIC PRESSURE INDICATOR AND AUTOMATIC PRESSURE LIMITER, INCLUDING LUER LOCK FOR SUCTION ATTACHMENT;

(v) claims benefit of prior U.S. Provisional Patent Application Ser. No. 62/992,667, filed Mar. 20, 2020 by Guard Medical SAS and Machiel van der Leest et al. for MANUALLY-OPERATED NEGATIVE PRESSURE WOUND THERAPY (NPWT) BANDAGE WITH IMPROVED PUMP EFFICIENCY, AUTOMATIC PRESSURE INDICATOR AND AUTOMATIC PRESSURE LIMITER, WHEREIN THE WOUND CHAMBER COMPRISES A LATERAL EXTENSION, AND WHEREIN THE PUMP ASSEMBLY IS IN FLUID COMMUNICATION WITH THE LATERAL EXTENSION, SO THAT THE PUMP ASSEMBLY IS LATERALLY OFFSET FROM THE WOUND WHILE REMAINING IN FLUID COMMUNICATION WITH THE WOUND; and (vi) claims benefit of prior U.S. Provisional Patent Application Ser. No. 63/081,690, filed Sep. 22, 2020 by Guard Medical SAS and Machiel van der Leest et al. for NEGATIVE PRESSURE WOUND THERAPY (NPWT) BANDAGE.

The nine (9) above-identified patent applications are hereby incorporated herein by reference.

FIELD OF THE INVENTION

This invention relates to bandages in general, and more particularly to negative pressure wound therapy (NPWT) bandages.

BACKGROUND OF THE INVENTION

Bandages are used to provide wound care during healing. More particularly, bandages generally provide a covering for a wound so as to shield the wound from contaminants and microbes during healing. Most bandages also provide a closure feature to help hold the edges of the wound in close apposition during healing. Bandages also frequently include gauze or the like to receive exudates emerging from the wound during healing.

Negative pressure wound therapy (NPWT) bandages apply a negative pressure to a wound during healing. This negative pressure helps reduce the likelihood of contaminants and microbes entering the wound during healing, helps draw exudates from the wound during healing, and can promote beneficial biological responses at the wound site. More particularly, NPWT bandages typically comprise (i) an absorbent dressing configured to make a fully-sealed chamber around the perimeter of a wound ("the wound chamber"), (ii) a source of negative pressure, and (iii) a conduit extending between the fully-sealed wound chamber and the source of negative pressure. As a result of this construction, the absorbent dressing can be applied to a wound so as to create a fully-sealed chamber around the perimeter of the wound, and the source of negative pressure can apply a negative pressure to the fully-sealed wound chamber, such that any contaminants and microbes present at the wound site are drawn away from the wound, exudates are drawn out of the wound, and beneficial biological responses are promoted at the wound site.

Most NPWT bandages are part of a large, complex NPWT system, in the sense that (i) the absorbent dressings are generally fairly large (e.g., they are sized to cover large open wounds), (ii) the sources of negative pressure are generally fairly large, and formed and located separate from the absorbent dressings (e.g., the sources of negative pressure typically comprise electrically-powered suction pumps or vacuum canisters), and (iii) the NPWT systems generally require substantial training to use. These NPWT systems also tend to be quite expensive.

Efforts have been made to provide a small, simplified and less expensive NPWT bandage where the source of negative pressure is integrated with the absorbent dressing. By way of example but not limitation, efforts have been made to provide an NPWT bandage where a manually-operated suction pump is integrated into the absorbent dressing. Unfortunately, current NPWT bandages integrating a suction pump with the absorbent dressing tend to suffer from a variety of deficiencies, e.g., they have a complex design, and/or are expensive, and/or are complicated to use, and/or are bulky (including having a high profile), and/or cause additional trauma to the wound during use, and/or have poor pump efficiency, and/or lack a way of indicating the level of negative pressure created, and/or lack a way of limiting the level of negative pressure created, etc. In this latter respect it should be appreciated that where too high a level of negative pressure is created, the NPWT bandage can cause trauma to the patient, e.g., blistering, capillary leakage, etc.

Thus there is a need for a new and improved NPWT bandage which is simple, inexpensive, easy-to-use, small in size (including having a low profile), is atraumatic to the wound during use, has improved pump efficiency, incorporates an automatic pressure indicator for indicating the level of negative pressure created, and provides an automatic pressure limiter for limiting the level of negative pressure created.

SUMMARY OF THE INVENTION

These and other objects of the invention are addressed by the provision and use of a new and improved NPWT bandage which is simple, inexpensive, easy-to-use, small in size (including having a low profile), is atraumatic to the wound during use, has improved pump efficiency, incorporates an automatic pressure indicator for indicating the level of negative pressure created, and provides an automatic pressure limiter for limiting the level of negative pressure created.

In one preferred form of the invention, there is provided a negative pressure wound therapy (NPWT) bandage for applying negative pressure to a wound, said NPWT bandage comprising:

a membrane configured for disposition over a wound so as to form a wound chamber between said membrane and the wound, said membrane comprising a wound-side surface, an atmosphere-side surface, and an opening extending through said membrane from said wound-side surface to said atmosphere-side surface; and a pump assembly carried by said membrane, said pump assembly comprising:

- a pump body comprising a wall structure disposed about a pump chamber, wherein at least a portion of said wall structure is resilient;
- a wound-side passageway extending through said wall structure and communicating with the wound chamber through said opening formed in said membrane;
- a wound-side one-way valve disposed in said wound-side passageway, said wound-side one-way valve being configured to allow fluid to flow through said wound-side passageway from the wound chamber to said pump chamber but to prevent fluid from flowing through said wound-side passageway from said pump chamber to the wound chamber;
- an atmosphere-side passageway extending through said wall structure and connecting said pump chamber and the atmosphere; and
- an atmosphere-side one-way valve disposed in said atmosphere-side passageway, said atmosphere-side one-way valve being configured to allow fluid to flow through said atmosphere-side passageway from said pump chamber to the atmosphere but to prevent fluid from flowing through said atmosphere-side passageway from the atmosphere to said pump chamber;

such that when a compressive force is applied to said wall structure of said pump body, fluid within said pump chamber will be forced out of said pump chamber via said atmosphere-side passageway, and when the compressive force applied to said wall structure of said pump body is thereafter reduced, fluid within the wound chamber will be drawn into said pump chamber through said wound-side passageway.

Preferably, the NPWT bandage is configured so that when the pressure differential between the pressure of the fluid within said pump chamber and atmospheric pressure is below a predetermined threshold, said pump body of said pump assembly will assume a substantially fully expanded configuration, and when said pressure differential between the pressure of the fluid within said pump chamber and atmospheric pressure is above said predetermined threshold, said pump body of said pump assembly will assume a substantially fully collapsed configuration.

Even more preferably, the NPWT bandage is configured so that said pump body abruptly changes state between said substantially fully expanded configuration and said substantially fully collapsed configuration, and between said substantially fully collapsed configuration and said substantially fully expanded configuration, as said pressure differential crosses said predetermined threshold so as to effectively constitute a substantially "binary state" device.

In another preferred form of the invention, there is provided a method for applying negative pressure to a wound, the method comprising:

providing a negative pressure wound therapy (NPWT) bandage comprising:

- a membrane configured for disposition over a wound so as to form a wound chamber between said membrane and the wound, said membrane comprising a wound-side surface, an atmosphere-side surface, and an opening extending through said membrane from said wound-side surface to said atmosphere-side surface; and
- a pump assembly carried by said membrane, said pump assembly comprising:
  - a pump body comprising a wall structure disposed about a pump chamber, wherein at least a portion of said wall structure is resilient;
  - a wound-side passageway extending through said wall structure and communicating with the wound chamber through said opening formed in said membrane;
  - a wound-side one-way valve disposed in said wound-side passageway, said wound-side one-way valve being configured to allow fluid to flow through said wound-side passageway from the wound chamber to said pump chamber but to prevent fluid from flowing through said wound-side passageway from said pump chamber to the wound chamber;
  - an atmosphere-side passageway extending through said wall structure and connecting said pump chamber and the atmosphere; and an atmosphere-side one-way valve disposed in said atmosphere-side passageway, said atmosphere-side one-way valve being configured to allow fluid to flow through said atmosphere-side passageway from said pump chamber to the atmosphere but to prevent fluid from flowing through said atmosphere-side passageway from the atmosphere to said pump chamber;

such that when a compressive force is applied to said wall structure of said pump body, fluid within said pump chamber will be forced out of said pump chamber via said atmosphere-side passageway, and when the compressive force applied to said wall structure of said pump body is thereafter reduced, fluid within the wound chamber will be drawn into said pump chamber through said wound-side passageway;

positioning said negative pressure wound therapy (NPWT) bandage over the wound so as to form a wound chamber between said membrane and the wound; and applying a compressive force to said wall structure of said pump body, and thereafter reducing the compressive force applied to said wall structure of said pump body, so as to apply negative pressure to the wound.

In another preferred form of the invention, there is provided a negative pressure wound therapy (NPWT) bandage for applying negative pressure to a wound, said NPWT bandage comprising:

a membrane configured for disposition over a wound so as to form a wound chamber between said membrane and the wound, said membrane comprising a wound-side surface, an atmosphere-side surface, and an opening extending through said membrane from said wound-side surface to said atmosphere-side surface; and a pump carried by said membrane and comprising a wall chamber disposed about a pump chamber, wherein at least a portion of said wall chamber is resilient, and further wherein said pump chamber communicates with the wound chamber through said opening formed in said membrane;

wherein no part of said pump chamber is defined by the wound.

In another preferred form of the invention, there is provided a negative pressure wound therapy (NPWT) bandage for applying negative pressure to a wound, said NPWT bandage comprising:

a membrane configured for disposition over a wound so as to form a wound chamber between said membrane and the wound, said membrane comprising a wound-side surface, an atmosphere-side surface, and an opening extending through said membrane from said wound-side surface to said atmosphere-side surface; and a pump carried by said membrane and comprising a wall chamber disposed about a pump chamber, wherein at least a portion of said wall chamber is resilient, and further wherein said pump chamber communicates with the wound chamber through said opening formed in said membrane;

wherein said pump does not apply positive pressure to the wound.

In another preferred form of the invention, there is provided a negative pressure wound therapy (NPWT) bandage for applying negative pressure to a wound, said NPWT bandage comprising:

a membrane configured for disposition over a wound so as to form a wound chamber between said membrane and the wound, said membrane comprising a wound-side surface, an atmosphere-side surface, and an opening extending through said membrane from said wound-side surface to said atmosphere-side surface; and a pump carried by said membrane and comprising a wall chamber disposed about a pump chamber, wherein at least a portion of said wall chamber is resilient, and further wherein said pump chamber communicates with the wound chamber through said opening formed in said membrane;

wherein said pump is connected to the wound chamber such that a reduction in the volume of the pump chamber does not cause a change in pressure in the wound chamber.

In another preferred form of the invention, the negative pressure wound therapy (NPWT) bandage is constructed so that it also provides a negative pressure decay "warning state" indicator.

In one form of the invention, there is provided a negative pressure wound therapy (NPWT) bandage for applying negative pressure to a wound, the NPWT bandage comprising:

a membrane configured for disposition over a wound so as to form a wound chamber between the membrane and the wound, the membrane comprising a wound-side surface, an atmosphere-side surface, and an opening extending through the membrane from the wound-side surface to the atmosphere-side surface; and a pump assembly carried by the membrane, the pump assembly comprising:

a pump body comprising a wall structure disposed about a pump chamber, wherein at least a portion of the wall structure is resilient, and further wherein the pump chamber communicates with the wound chamber through the opening formed in the membrane; and an atmosphere-side passageway extending through the wall structure so as to fluidically connect the pump chamber to the atmosphere;

such that when a compressive force is applied to the wall structure of the pump body, fluid within the pump chamber is forced out of the pump chamber via the atmosphere-side passageway, and when the compressive force applied to the wall structure of the pump body is thereafter reduced, fluid within the wound chamber is drawn into the pump chamber through the opening formed in the membrane;

wherein when the pressure differential between the pressure of the fluid within the pump chamber and the atmospheric pressure is below a predetermined threshold, the pump body will assume a substantially fully expanded configuration, whereby to indicate that negative pressure within the wound chamber is below the predetermined threshold, and when the pressure differential between the pressure of the fluid within the pump chamber and the atmospheric pressure is above the predetermined threshold, the pump body will assume a substantially fully collapsed configuration, whereby to indicate that the negative pressure within the wound chamber is above the predetermined threshold; and further wherein the pump body is configured to provide a visual indicator that the negative pressure within the wound chamber is falling, but has not fallen enough to go below the predetermined threshold and cause a transformation of the pump body into its substantially fully expanded configuration.

In another form of the invention, there is provided a method for applying negative pressure to a wound, the method comprising:

providing a negative pressure wound therapy (NPWT) bandage comprising:

a membrane configured for disposition over a wound so as to form a wound chamber between the membrane and the wound, the membrane comprising a wound-side surface, an atmosphere-side surface, and an opening extending through the membrane from the wound-side surface to the atmosphere-side surface; and a pump assembly carried by the membrane, the pump assembly comprising:

a pump body comprising a wall structure disposed about a pump chamber, wherein at least a portion of the wall structure is resilient, and further wherein the pump chamber communicates with the wound chamber through the opening formed in the membrane; and an atmosphere-side passageway extending through the wall structure so as to fluidically connect the pump chamber to the atmosphere;

wherein when a compressive force is applied to the wall structure of the pump body, fluid within the pump chamber is forced out of the pump chamber via the atmosphere-side passageway, and when the compressive force applied to the wall structure of the pump body is thereafter reduced, fluid within the wound chamber is drawn into the pump chamber through the opening formed in the membrane;

wherein when the pressure differential between the pressure of the fluid within the pump chamber and the atmospheric pressure is below a predetermined threshold, the pump body assumes a substantially fully expanded configuration, whereby to indicate that negative pressure within the wound chamber is below the predetermined threshold, and when the pressure differential between the pressure of the fluid within the pump chamber and the atmospheric pressure is above the predetermined threshold, the pump body assumes a substantially fully collapsed configuration, whereby to indicate that the negative pressure within the wound chamber is above the predetermined threshold; and further wherein the pump body is configured to provide a visual indicator that the negative pressure within the wound chamber is falling, but has not fallen enough to go below the predetermined threshold and cause a transformation of the pump body into its substantially fully expanded configuration;

positioning the NPWT bandage over the wound so as to form the wound chamber between the membrane and the wound; and applying a compressive force to the wall structure of the pump body, and thereafter reducing the compressive force applied to the wall structure of the pump body, so as to apply negative pressure to the wound.

In another preferred form of the invention, the negative pressure wound therapy (NPWT) bandage includes a canister for collecting exudates.

In one form of the invention, there is provided a negative pressure wound therapy (NPWT) bandage for applying negative pressure to a wound, the NPWT bandage comprising:

a membrane configured for disposition over a wound so as to form a wound chamber between the membrane and the wound, the membrane comprising a wound-side surface, an atmosphere-side surface, and an opening extending through the membrane from the wound-side surface to the atmosphere-side surface;

a pump assembly carried by the membrane, the pump assembly comprising:

a pump body comprising a wall structure disposed about a pump chamber, wherein at least a portion of the wall structure is resilient;

a wound-side passageway extending through the wall structure and communicating with the wound chamber; and an atmosphere-side passageway extending through the wall structure and connecting the pump chamber to the atmosphere; and a canister configured to be in fluid communication with the wound chamber and the pump assembly, the canister comprising an interior chamber for collecting exudates exiting the wound chamber; wherein the pump assembly is configured to generate a negative air pressure within the wound chamber such that exudates from the wound chamber will flow out of the wound chamber and into the interior chamber of the canister.

In another form of the invention, there is provided a method for applying negative pressure to a wound, the method comprising:

providing a negative pressure wound therapy (NPWT) bandage comprising:

a membrane configured for disposition over a wound so as to form a wound chamber between the membrane and the wound, the membrane comprising a wound-side surface, an atmosphere-side surface, and an opening extending through the membrane from the wound-side surface to the atmosphere-side surface;

a pump assembly carried by the membrane, the pump assembly comprising:

a pump body comprising a wall structure disposed about a pump chamber, wherein at least a portion of the wall structure is resilient;

a wound-side passageway extending through the wall structure and communicating with the wound chamber; and an atmosphere-side passageway extending through the wall structure and connecting the pump chamber to the atmosphere; and a canister configured to be in fluid communication with the wound chamber and the pump assembly, the canister comprising an interior chamber for collecting exudates exiting the wound chamber;

wherein the pump assembly is configured to generate a negative air pressure within the wound chamber such that exudates from the wound chamber will flow out of the wound chamber and into the interior chamber of the canister;

positioning the NPWT bandage over the wound so as to form a wound chamber between the membrane and the wound; and generating a negative air pressure within the wound chamber so that exudates flow from the wound chamber and into the interior chamber of the canister.

In another preferred form of the invention, the negative pressure wound therapy (NPWT) bandage includes a luer lock for suction attachment.

In one form of the invention, there is provided a negative pressure wound therapy (NPWT) bandage for applying negative pressure to a wound, the NPWT bandage comprising:

a membrane configured for disposition over a wound so as to form a wound chamber between the membrane and the wound, the membrane comprising a wound-side surface, an atmosphere-side surface, and an opening extending through the membrane from the wound-side surface to the atmosphere-side surface;

a pump assembly carried by the membrane, the pump assembly comprising:

a pump body comprising a wall structure disposed about a pump chamber, wherein at least a portion of the wall structure is resilient;

a wound-side passageway extending through the wall structure and communicating with the wound chamber through the opening in the membrane; and an atmosphere-side passageway extending through the wall structure and connecting the pump chamber to the atmosphere; and a suction source configured to be connected to the pump assembly for establishing negative air pressure within the wound chamber;

wherein when the negative air pressure within the wound chamber is below a predetermined threshold, the pump body will assume a substantially fully expanded configuration, and when the negative air pressure within the wound chamber is above the predetermined threshold, the pump body will assume a substantially fully collapsed configuration.

In another form of the invention, there is provided a method for applying negative pressure to a wound, the method comprising:

providing a negative pressure wound therapy (NPWT) bandage comprising:

a membrane configured for disposition over a wound so as to form a wound chamber between the membrane and the wound, the membrane comprising a wound-side surface, an atmosphere-side surface, and an opening extending through the membrane from the wound-side surface to the atmosphere-side surface;

a pump assembly carried by the membrane, the pump assembly comprising:

a pump body comprising a wall structure disposed about a pump chamber, wherein at least a portion of the wall structure is resilient;

a wound-side passageway extending through the wall structure and communicating with the wound chamber through the opening in the membrane;

an atmosphere-side passageway extending through the wall structure and connecting the pump chamber and the atmosphere; and a suction source configured to be connected to the pump assembly for establishing negative air pressure within the wound chamber;

wherein when the negative air pressure within the wound chamber is below a predetermined threshold, the pump body will assume a substantially fully expanded configuration, and when the negative air pressure within the wound chamber is above the predetermined threshold, the pump body will assume a substantially fully collapsed configuration;

positioning the NPWT bandage over the wound so as to form a wound chamber between the membrane and the wound; and connecting the suction source to the pump assembly to generate a negative air pressure within the wound chamber.

In another form of the invention, there is provided a negative pressure wound therapy (NPWT) bandage for applying negative pressure to a wound, the NPWT bandage comprising:

a membrane configured for disposition over a wound so as to form a wound chamber between the membrane and the wound, the membrane comprising a wound-side surface, an atmosphere-side surface, and an opening extending through the membrane from the wound-side surface to the atmosphere-side surface;

a pump assembly carried by the membrane, the pump assembly comprising:

a pump body comprising a wall structure disposed about a pump chamber, wherein at least a portion of the wall structure is resilient;

a wound-side passageway extending through the wall structure and communicating with the wound chamber through the opening in the membrane; and an atmosphere-side passageway extending through the wall structure and connecting the pump chamber to the atmosphere; and a connector for connecting a suction source to the pump assembly for establishing negative air pressure within the wound chamber;

wherein when the negative air pressure within the wound chamber is below a predetermined threshold, the pump body will assume a substantially fully expanded configuration, and when the negative air pressure within the wound chamber is above the predetermined threshold, the pump body will assume a substantially fully collapsed configuration.

In another preferred form of the invention, the negative pressure wound therapy (NPWT) bandage is provided with a pump assembly that is laterally offset from a wound while remaining in fluid communication with the wound.

In one form of the invention, there is provided a negative pressure wound therapy (NPWT) bandage for applying negative pressure to a wound, the NPWT bandage comprising:

a membrane comprising a first portion configured for disposition over a wound so as to form a wound chamber between the membrane and the wound, and a second portion configured to extend laterally away from the wound, the membrane comprising a wound-side surface, an atmosphere-side surface, and an opening extending from the wound-side surface to the atmosphere-side surface, the opening being in fluid communication with the wound chamber; and a pump assembly carried by the second portion of the membrane, the pump assembly comprising:

a pump body comprising a wall structure disposed about a pump chamber, wherein at least a portion of the wall structure is resilient;

a wound-side passageway extending through the wall structure and communicating with the wound chamber through the opening in the membrane; and an atmosphere-side passageway extending through the wall structure and connecting the pump chamber to the atmosphere;

wherein the pump assembly is configured to generate a negative air pressure within the wound chamber.

In another form of the invention, there is provided a method for applying negative pressure to a wound, the method comprising:

providing a negative pressure wound therapy (NPWT) bandage comprising:

a membrane comprising a first portion configured for disposition over a wound so as to form a wound chamber between the membrane and the wound, and a second portion configured to extend laterally away from the wound, the membrane comprising a wound-side surface, an atmosphere-side surface, and an opening extending from the wound-side surface to the atmosphere-side surface, the opening being in fluid communication with the wound chamber; and a pump assembly carried by the second portion of the membrane, the pump assembly comprising:

a pump body comprising a wall structure disposed about a pump chamber, wherein at least a portion of the wall structure is resilient;

a wound-side passageway extending through the wall structure and communicating with the wound chamber through the opening formed in the membrane; and an atmosphere-side passageway extending through the wall structure and connecting the pump chamber to the atmosphere;

wherein the pump assembly is configured to generate a negative air pressure within the wound chamber;

positioning the first portion of the NPWT bandage over the wound so as to form a wound chamber between the membrane and the wound and positioning the second portion of the membrane on anatomy that is laterally offset from the wound; and generating a negative air pressure within the wound chamber.

In another preferred form of the invention, there is provided a negative pressure wound therapy bandage for covering a wound, the bandage comprising a transparent top layer which captures a layer of foam against the wound, wherein the foam layer is provided with a series of windows which (i) allow direct visualization of the wound, and (ii) provide a metric along the length of the bandage to indicate whether the bandage needs to be replaced. The foam layer also comprises perimeter serrations which allow the bandage to conform to a curved wound. This novel negative pressure wound therapy bandage may be used with an on-board pump or with a pump located remote from the bandage (or with another source of suction, e.g., wall suction). This novel bandage may also be used without applying negative pressure to the wound.

In one form of the invention, there is provided a negative pressure wound therapy (NPWT) bandage for applying negative pressure to a wound, the NPWT bandage comprising:

a membrane configured for disposition over a wound so as to form a wound chamber between the membrane and the wound, the membrane comprising a wound-side surface, an atmosphere-side surface, and an opening extending from the wound-side surface to the atmosphere-side surface, the opening being in fluid communication with the wound chamber;

wherein the membrane comprises a transparent layer and an absorbent layer, wherein the absorbent layer is disposed on the wound-side of the membrane;

wherein the absorbent layer comprises a plurality of windows extending through the absorbent layer; and further wherein the transparent layer of the membrane and the plurality of windows of the absorbent layer of the membrane permit visualization of the wound through the membrane; and a pump assembly carried by the membrane, the pump assembly comprising:

a pump body comprising a wall structure defining a pump chamber, wherein at least a portion of the wall structure is resilient;

a wound-side passageway extending through the wall structure and communicating with the wound chamber through the opening in the membrane; and an atmosphere-side passageway extending through the wall structure and connecting the pump chamber to the atmosphere;

wherein the pump assembly is configured to generate a negative air pressure within the wound chamber.

In another form of the invention, there is provided a bandage for covering a wound releasing exudate, the bandage comprising:

a membrane configured for disposition over a wound so as to form a wound chamber between the membrane and the wound, the membrane comprising a wound-side surface, an atmosphere-side surface, and an opening extending from the wound-side surface to the atmosphere-side surface, the opening being in fluid communication with the wound chamber;

wherein the membrane comprises a transparent layer and an absorbent layer, wherein the absorbent layer is disposed on the wound-side of the membrane;

wherein the absorbent layer comprises a plurality of windows extending through the absorbent layer; and further wherein the transparent layer of the membrane and the plurality of windows of the absorbent layer of the membrane permit visualization of the wound through the membrane.

In another form of the invention, there is provided a method for applying negative pressure to a wound, the method comprising:

providing a negative pressure wound therapy (NPWT) bandage comprising:

a membrane configured for disposition over a wound so as to form a wound chamber between the membrane and the wound, the membrane comprising a wound-side surface, an atmosphere-side surface, and an opening extending from the wound-side surface to the atmosphere-side surface, the opening being in fluid communication with the wound chamber;

wherein the membrane comprises a transparent layer and an absorbent layer, wherein the absorbent layer is disposed on the wound-side of the membrane;

wherein the absorbent layer comprises a plurality of windows extending through the absorbent layer; and further wherein the transparent layer of the membrane and the plurality of windows of the absorbent layer of the membrane permit visualization of the wound through the membrane; and a pump assembly carried by the membrane, the pump assembly comprising:

a pump body comprising a wall structure defining a pump chamber, wherein at least a portion of the wall structure is resilient;

a wound-side passageway extending through the wall structure and communicating with the wound chamber through the opening formed in the membrane; and an atmosphere-side passageway extending through the wall structure and connecting the pump chamber to the atmosphere;

wherein the pump assembly is configured to generate a negative air pressure within the wound chamber;

positioning the NPWT bandage over the wound so as to form a wound chamber between the membrane and the wound;

generating a negative air pressure within the wound chamber; and visualizing the absorbent layer of the membrane to determine whether the NPWT bandage needs to be removed from the wound and replaced with a new NPWT bandage.

In another form of the invention, there is provided a method for covering a wound releasing exudate, the method comprising:

providing a bandage comprising:

a membrane configured for disposition over a wound so as to form a wound chamber between the membrane and the wound, the membrane comprising a wound-side surface, an atmosphere-side surface, and an opening extending from the wound-side surface to the atmosphere-side surface, the opening being in fluid communication with the wound chamber;

wherein the membrane comprises a transparent layer and an absorbent layer, wherein the absorbent layer is disposed on the wound-side of the membrane;

wherein the absorbent layer comprises a plurality of windows extending through the absorbent layer; and further wherein the transparent layer of the membrane and the plurality of windows of the absorbent layer of the membrane permit visualization of the wound through the membrane;

positioning the bandage over the wound so as to form a wound chamber between the membrane and the wound; and visualizing the absorbent layer of the membrane to determine whether the bandage needs to be removed from the wound and replaced with a new bandage.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 4A is a schematic view showing, for two different size wound chambers (i.e., a 7.5 mL wound chamber and a 15 mL wound chamber), a maximum negative pressure that may be established with (i) a deformable pump body having two one-way valves (with one one-way valve being disposed on either side of the deformable pump body), and (ii) a deformable pump body having a single one-way valve (note: in the comparison shown in FIG. 4A, the volume of the pump chamber of the deformable pump body with 1 one-way valve is the same as the volume of the pump chamber of the deformable pump body with 2 one-way valves);

DETAILED DESCRIPTION OF THE PREFERRED EMBODIMENTS

Figure 1:
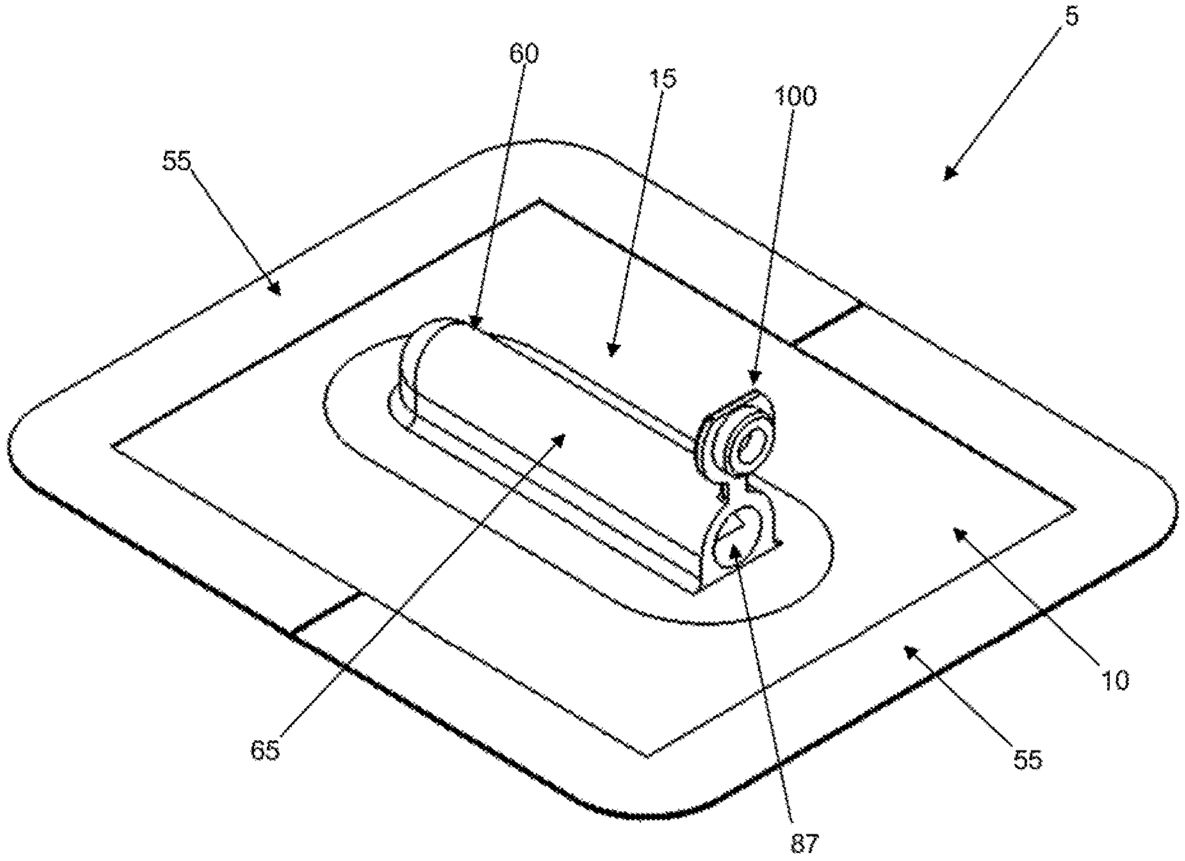
FIGS. 1-4 are schematic views showing a new and improved NPWT bandage formed in accordance with the present invention, with FIGS. 2 and 3 being exploded views.
Figure 2:
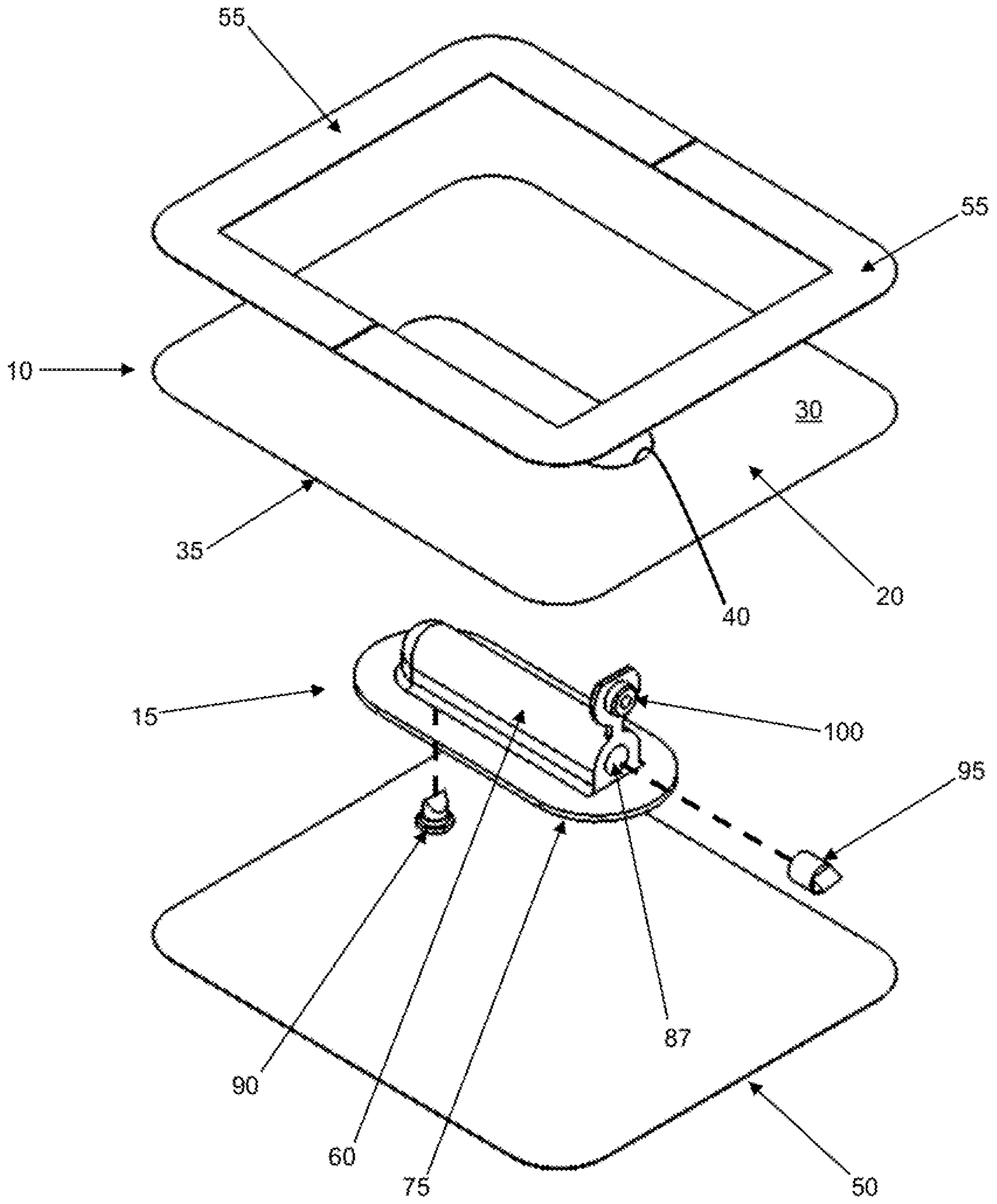
Figure 3:
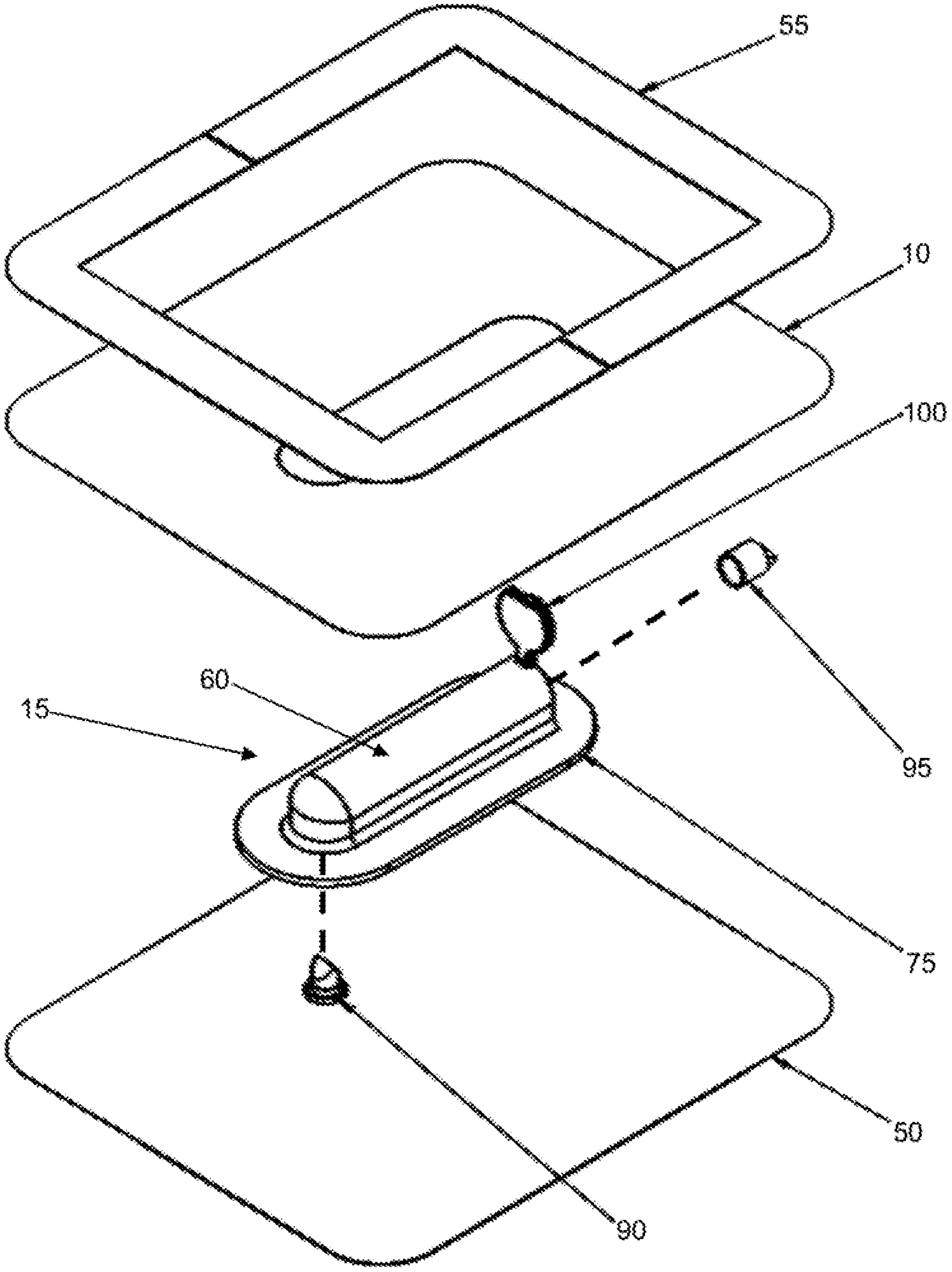
Figure 4:
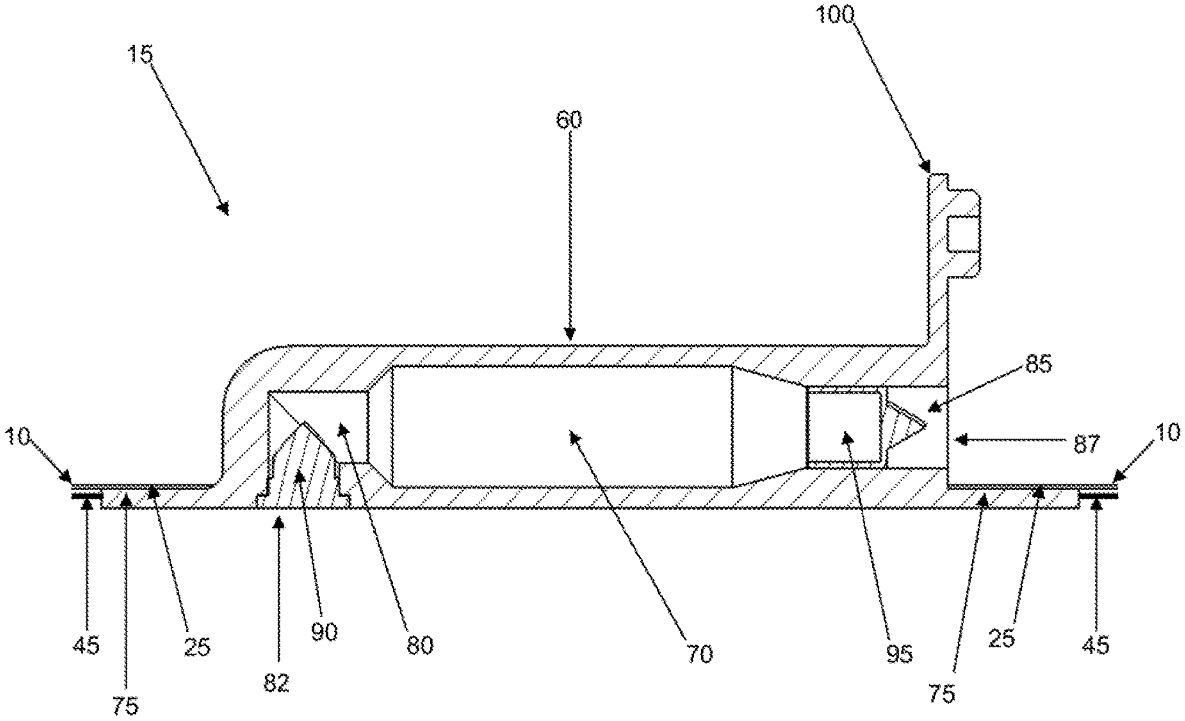

The present invention comprises the provision and use of a new and improved NPWT bandage which is simple, inexpensive, easy-to-use, small in size (including having a low profile), is atraumatic to the wound during use, has improved pump efficiency, incorporates an automatic pressure indicator for indicating the level of negative pressure created, and provides an automatic pressure limiter for limiting the level of negative pressure created.

The Manually-Operated Negative Pressure Wound Therapy (NPWT) Bandage in General More particularly, and looking first at FIGS. 1-4, there is shown a manually-operated negative pressure wound therapy (NPWT) bandage 5 having improved pump efficiency, an automatic pressure indicator for indicating the level of negative pressure created, and an automatic pressure limiter for limiting the level of negative pressure created.

NPWT bandage 5 generally comprises a membrane (or sheet) 10 and a pump assembly 15.

As will hereinafter be discussed, membrane 10 is configured to make a fully-sealed chamber around the perimeter of a wound, whereby to define a wound chamber.

And as will hereinafter be discussed, pump assembly 15 is configured to apply a negative pressure to the fully-sealed wound chamber, such that any contaminants and microbes present at the wound site are drawn away from the wound, exudates are drawn out of the wound, and beneficial biological responses are promoted at the wound site. Significantly, pump assembly 15 is designed to provide improved pump efficiency, an automatic pressure indicator for indicating the level of negative pressure created, and an automatic pressure limiter for limiting the level of negative pressure created, as will hereinafter be discussed.

The Membrane

More particularly, membrane 10 comprises a flat planar sheet 20 formed out of a flexible, substantially air-impermeable material, e.g., Tegaderm from 3M Company (which has also been known as the Minnesota Mining and Manufacturing Company), so that it can conform to body contours and form a substantially air-tight chamber around the perimeter of a wound (i.e., the wound chamber). Membrane 10 is characterized by a wound-side surface 25 and an atmosphere-side surface 30. Membrane 10 is also characterized by an outer perimeter 35 and an inner opening 40.

An adhesive 45 is preferably disposed on wound-side surface 25 of membrane 10. A release liner 50 is preferably disposed on wound-side surface 25 atop adhesive 45 so as to keep adhesive 45 covered until use.

A removable stiffener 55 is preferably disposed on atmosphere-side surface 30 of membrane 10. Removable stiffener 55 serves to facilitate manipulation of NPWT bandage 5 (and particularly membrane 10) during removal of the NPWT bandage from its sterile packaging and during positioning of the NPWT bandage about a wound. Removable stiffener 55 is intended to be removed from membrane 10 once NPWT bandage 5 has been secured about the wound site. Removable stiffener 55 may be provided as a single element or, more preferably, removable stiffener 55 is provided as a pair of elements so as to facilitate removal from membrane 10 after NPWT bandage 5 has been secured about the wound site.

The Pump Assembly

Figure 5:
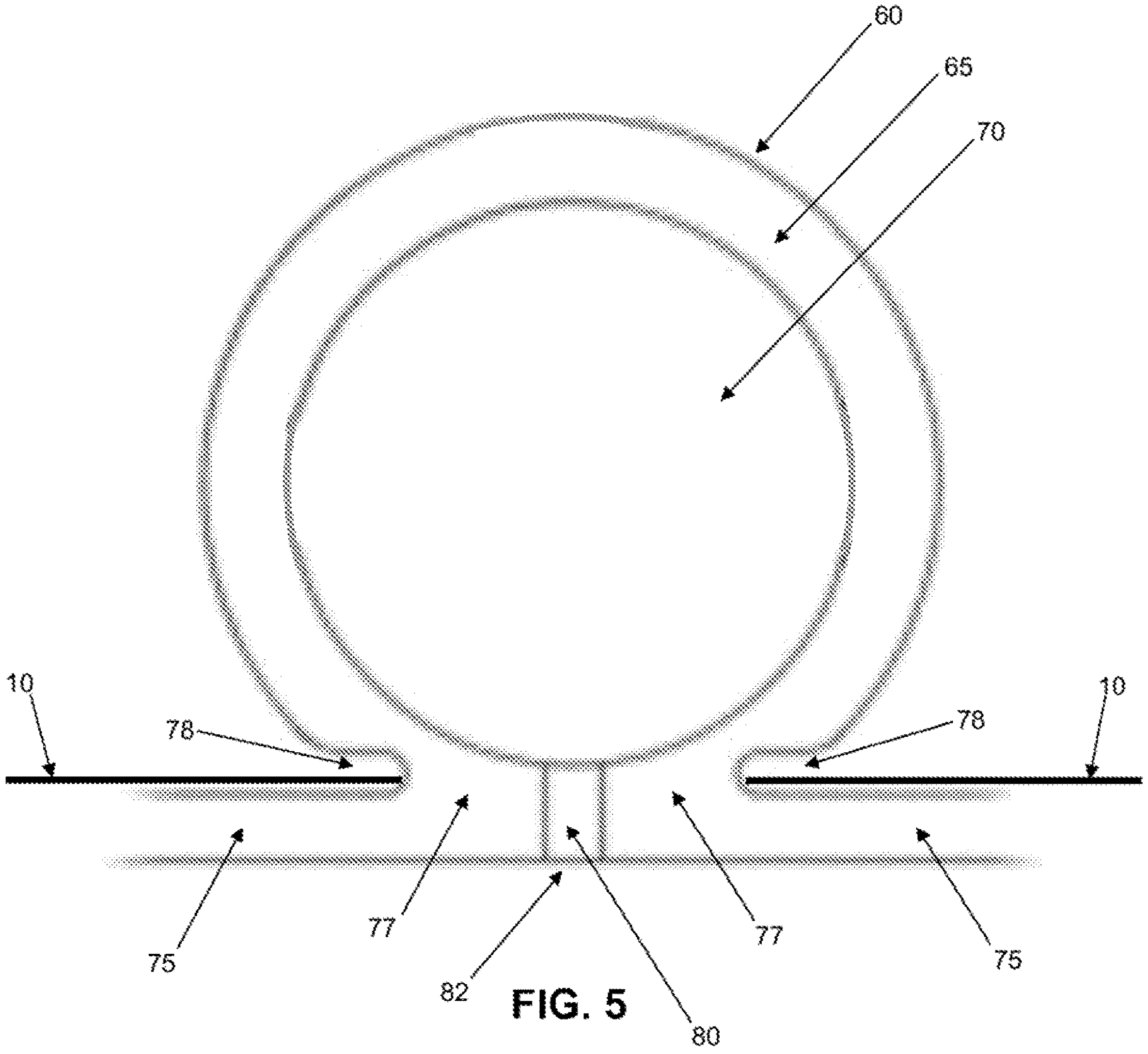
FIGS. 5 and 6 are schematic views showing the pump body of the pump assembly of the NPWT bandage shown in FIGS. 1-4 in its substantially fully expanded configuration (FIG. 5) and in its substantially fully collapsed configuration (FIG. 6)

Pump assembly 15 comprises a pump body 60 having a generally cylindrical shape and comprising a side wall 65 and an inner chamber 70. Pump body 60 is formed out of a resilient material, e.g., silicone, such that side wall 65 may be compressed inwardly by the application of an external force (e.g., squeezing by the thumb and forefinger of a user) and will then attempt to return to its original uncompressed state when the external force is removed. A pump flange 75 is preferably formed on one side of pump body 60. As will hereinafter be discussed in further detail, pump body 60 extends through inner opening 40 of membrane 10, and the upper surface of pump flange 75 is secured to the wound-side surface 25 of membrane 10 so that pump assembly 15 is secured to, and carried by, membrane 10. Pump flange 75 is preferably formed out of a flexible material so that it can conform (to at least a limited extent) to body contours. In one form of the invention, pump body 60 and pump flange 75 are formed integral with one another out of the same material, e.g., silicone. In one preferred form of the invention, side wall 65 of pump body 60 and pump flange 75 merge at a neck 77 (FIG. 5). And in one preferred form of the invention, neck 77 has a relatively small width relative to the full diameter of pump body 60, with recesses 78 extending inwardly between membrane 10 and pump body 60, such that pump body 60 is mounted to pump flange 75 but is still free to radially compress/radially expand with minimal interference from pump flange 75. A wound-side passageway 80 is formed in pump body 60 and communicates with inner chamber 70. Wound-side passageway 80 opens on the exterior of pump body 60 at a wound-side port 82. An atmosphere-side passageway 85 is formed in pump body 60 and also communicates with inner chamber 70. Atmosphere-side passageway 85 opens on the exterior of pump body 60 at an atmosphere-side port 87.

A wound-side one-way valve 90 is disposed in wound-side passageway 80 and is configured to permit fluid to enter inner chamber 70 through wound-side passageway 80 but to prevent fluid from exiting inner chamber 70 through wound-side passageway 80.

An atmosphere-side one-way valve 95 is disposed in atmosphere-side passageway 85 and is configured to permit fluid to exit inner chamber 70 through atmosphere-side passageway 85 but to prevent fluid from entering inner chamber 70 through atmosphere-side passageway 85.

As a result of this construction, when pump body 60 of pump assembly 15 is manually squeezed (e.g., by applying a compressive force to side wall 65 of pump body 60 with the thumb and forefinger of a user), fluid (e.g., air, liquid, etc.) within inner chamber 70 will be forced out of inner chamber 70 via atmosphere-side passageway 85, and when pump body 60 of pump assembly 15 is thereafter released (e.g., by relaxing the compressive force applied to side wall 65 of pump body 60 by the thumb and forefinger of a user), fluid (e.g., air, liquid, etc.) below wound-side surface 25 of membrane 10 (e.g., air, liquid, etc. within the wound chamber) will be drawn into inner chamber 70 through wound-side passageway 80 as the resilient side wall of the pump body returns to its uncompressed state.

Note that when pump body 60 of pump assembly 15 is manually squeezed, fluid (e.g., air, liquid, etc.) within inner chamber 70 is prevented from exiting inner chamber 70 through wound-side passageway 80 due to the one-way operation of wound-side one-way valve 90, and when pump body 60 of pump assembly 15 is thereafter released, air from the atmosphere is prevented from being drawn into inner chamber 70 through atmosphere-side passageway 85 due to the one-way operation of atmosphere-side one-way valve 95.

Thus it will be appreciated that repeatedly manually squeezing and releasing pump body 60 of pump assembly 15 will apply suction to the wound chamber disposed below wound-side surface 25 of membrane 10, whereby to create negative pressure at the wound site.

It should be appreciated that the present invention's approach of providing a pump assembly utilizing two one-way valves disposed on either side of a deformable pump body with an in-line configuration (i.e., wound-side one-way valve 90 and atmosphere-side one-way valve 95 disposed on either side of deformable pump body 60) provides a number of significant advantages which are not achievable with the prior art's approach of providing a deformable pump body utilizing a single one-way valve.

More particularly, and as will hereinafter be discussed, the present invention's approach of providing a pump assembly utilizing two one-way valves disposed on either side of a deformable pump body with an in-line configuration (i.e., wound-side one-way valve 90 and atmosphere-side one-way valve 95 disposed on either side of deformable pump body 60) allows substantially the same maximum negative pressure to be established at the wound site regardless of the size of the wound chamber. This is not achievable with the prior art's approach of providing a deformable pump body utilizing a single one-way valve.

In addition, the present invention's approach of providing a pump assembly utilizing two one-way valves disposed on either side of a deformable pump body with an in-line configuration (i.e., wound-side one-way valve 90 and atmosphere-side one-way valve 95 disposed on either side of deformable pump body 60) allows a greater constant selected maximum negative pressure to be achieved at the wound site than can be achieved at the wound site using a deformable pump body with a single one-way valve (which is reflective of the prior art's approach).

More particularly, FIG. 4A, shows, for two different size wound chambers (i.e., a 7.5 mL wound chamber and a 15 mL wound chamber), a maximum negative pressure that may be established with (i) a deformable pump body having two one-way valves (with one one-way valve being disposed on either side of the deformable pump body), and (ii) a deformable pump body having a single one-way valve (note: in the comparison shown in FIG. 4A, the volume of the pump chamber of the deformable pump body with 1 one-way valve is the same as the volume of the pump chamber of the deformable pump body with 2 one-way valves).

Inherent in FIG. 4A are a number of significant aspects of the present invention.

First, FIG. 4A shows that using a deformable pump body having two one-way valves (with one one-way valve being disposed on either side of the deformable pump body) to evacuate the wound chamber lets you establish substantially the same maximum negative pressure in the wound chamber regardless of the size of the wound chamber (i.e., it yields approximately −150.0 mm Hg for a 7.5 mL wound chamber and approximately −150.0 mm Hg for a 15 mL wound chamber), whereas using a deformable pump body having a single one-way valve does not (i.e., it yields approximately −80.0 mm Hg for a 7.5 mL wound chamber and approximately −50.0 mm Hg for a 15 mL wound chamber). Thus, the NPWT bandage of the present invention allows substantially the same maximum negative pressure to be established at the wound site regardless of the size of the wound chamber, whereas prior art NPWT bandages do not.

This unique feature of the present invention is clinically significant, inasmuch as (i) it is generally desirable to establish a selected maximum negative pressure at the wound site (e.g., between about 60 mm Hg and about 180 mm Hg), and (ii) it is generally difficult to know in advance the volume of the wound chamber (e.g., due to variations in medical applications, variations in patient anatomy, etc.). Thus, inasmuch as the NPWT bandage of the present invention allows substantially the same maximum negative pressure to be established at the wound site regardless of the size of the wound chamber, the present invention allows the NPWT bandage to be engineered in advance (e.g., at the time of manufacture) to establish a selected maximum negative pressure at the wound site, whereas prior art NPWT bandages do not.

Second, FIG. 4A shows that using a deformable pump body having two one-way valves (with one one-way valve being disposed on either side of the deformable pump body) to evacuate the wound chamber lets you establish a substantially higher maximum negative pressure in the wound chamber (i.e., it yields approximately −150.0 mm Hg for a 7.5 mL wound chamber and approximately −150.0 mm Hg for a 15 mL wound chamber) than can be established using a deformable pump body having a single one-way valve (i.e., it yields approximately −80.0 mm Hg for a 7.5 mL wound chamber and approximately −50.0 mm Hg for a 15 mL wound chamber). Thus, the NPWT bandage of the present invention allows a substantially higher maximum negative pressure to be established at the wound site.

Note also that the pressure within inner chamber 70 of pump body 60 is generally equal to the pressure below wound-side surface 25 of membrane 10 (i.e., the pressure within inner chamber 70 of pump body 60 is generally equal to the pressure within the wound chamber).

In one preferred form of the invention, pump assembly 15 also comprises a removable cap 100. Removable cap 100 is configured to selectively close off atmosphere-side passageway 85 to fluid flow when removable cap 100 is inserted into atmosphere-side passageway 85 so as to close off atmosphere-side port 87.

Pump assembly 15 is mounted to membrane 10 such that pump assembly is carried by membrane 10. More particularly, pump assembly 15 is mounted to membrane 10 by (i) passing pump body 60 of pump assembly 15 through inner opening 40 of membrane 10, (ii) bringing pump flange 75 up against wound-side surface 25 of membrane 10, and then (iii) adhering pump flange 75 to wound-side surface 25 of membrane 10 (e.g., by bonding, gluing, etc.). Note that pump assembly 15 and membrane 10 make a substantially air-tight connection.

Significantly, pump body 60 of pump assembly 15 is carefully configured to provide (i) improved pump efficiency, (ii) an automatic pressure indicator for indicating the level of negative pressure created, and (iii) an automatic pressure limiter for limiting the level of negative pressure created, as will hereinafter be discussed.

More particularly, pump body 60 of pump assembly 15 is specifically configured so that the pump body will abruptly change state between (i) a substantially fully expanded configuration where side wall 65 of pump body 60 and inner chamber 70 of pump body 60 have a substantially circular cross-section (see FIG. 5) when the pressure differential between the pressure of the fluid within inner chamber 70 and atmospheric pressure is below a given threshold, and (ii) a substantially fully collapsed configuration where side wall 65 of pump body 60 bows inwardly (see FIG. 6) when the pressure differential between the pressure of the fluid within inner chamber 70 and atmospheric pressure exceeds a given threshold.

Figure 6:
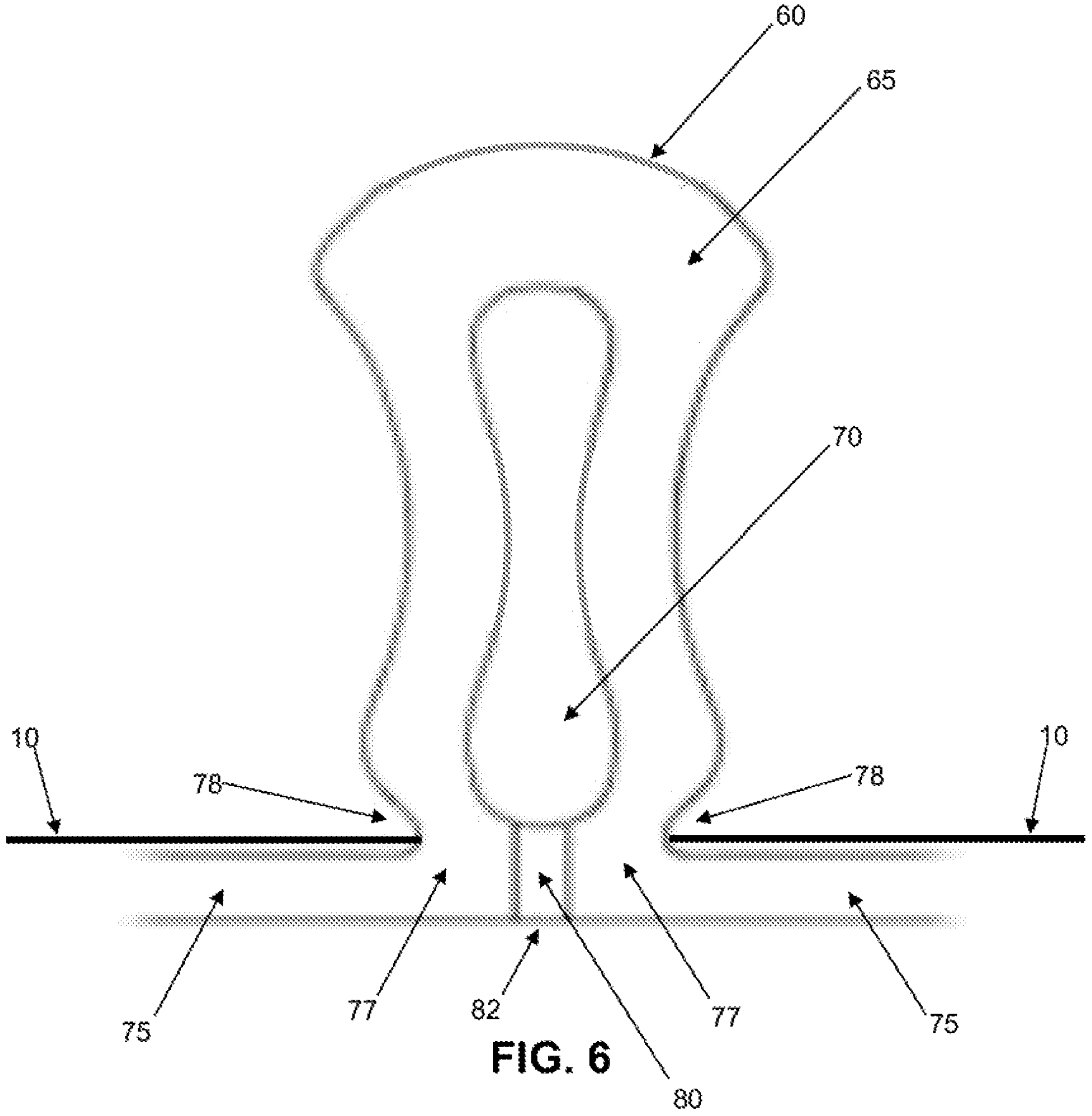

Specifically, when the pressure differential between the pressure of the fluid within inner chamber 70 and atmospheric pressure is below a given threshold, pump body 60 of pump assembly 15 will assume its substantially fully expanded configuration (FIG. 5), and when the pressure differential between the pressure of the fluid within inner chamber 70 and atmospheric pressure is above a given threshold, pump body 60 of pump assembly 15 will assume its substantially fully collapsed configuration (FIG. 6).

Figure 7:
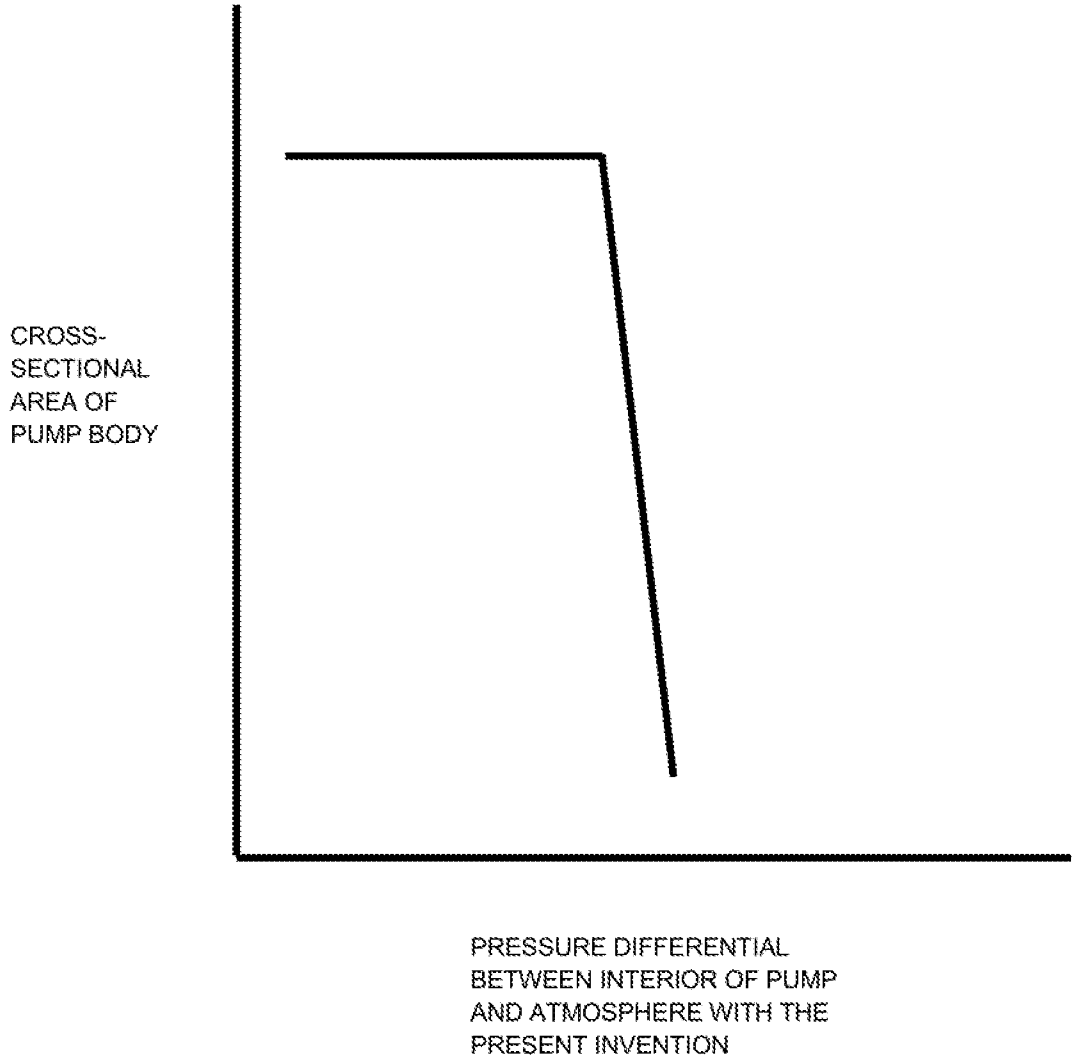
FIG. 7 is a schematic view showing how the pump body of the pump assembly of the NPWT bandage shown in FIGS. 1-4 abruptly changes state between its substantially fully expanded configuration and its substantially fully collapsed configuration.

Significantly, pump body 60 of pump assembly 15 is configured so that it will abruptly change state between its substantially fully expanded configuration (FIG. 5) and its substantially fully collapsed configuration (FIG. 6) when the pressure differential between the pressure of the fluid within inner chamber 70 and atmospheric pressure crosses the aforementioned given threshold. See FIG. 7, which is a graph showing the relationship between the diameter of side wall 65 of pump body 60 and the pressure differential between the pressure of a fluid within inner chamber 70 and atmospheric pressure. Thus, pump assembly 15 is specifically configured to essentially behave as a substantially "binary state" device—it is either substantially fully expanded (FIG. 5) or substantially fully collapsed (FIG. 6). In this respect it should be appreciated that, as used herein, the term "substantially "binary state" device" is intended to refer to a device which is inclined to assume either a substantially fully expanded condition or a substantially fully collapsed condition and, as used herein, the term "substantially "binary state" behavior" is intended to refer to the inclination of a device to assume either a substantially fully expanded condition or a substantially fully collapsed condition.

Note that the substantially "binary state" behavior of pump body 60 is a consequence of forming the pump body with a side wall 65 having a substantially circular cross-section, which gives the pump body an "over-the-center" deformation characteristic, i.e., the side wall of pump body 60 has a "failure" mode where it abruptly transitions from its substantially fully expanded configuration to its substantially fully collapsed configuration, and has a "restoration" mode where it abruptly transitions from its substantially fully collapsed configuration to its substantially fully expanded configuration. See FIG. 7. Note that by forming pump assembly 15 so that side wall 65 of pump body 60 and pump flange 75 merge at a neck 77 (FIG. 5), with neck 77 having a relatively small width relative to the full diameter of pump body 60, and with recesses 78 extending inwardly between membrane 10 and pump body 60, pump body 60 has a substantially circular cross-section over substantially its entire circumference, with pump body 60 free to radially compress/radially expand with minimal interference from pump flange 75, so that pump body 60 can exhibit substantially "binary state" behavior.

Figure 8:
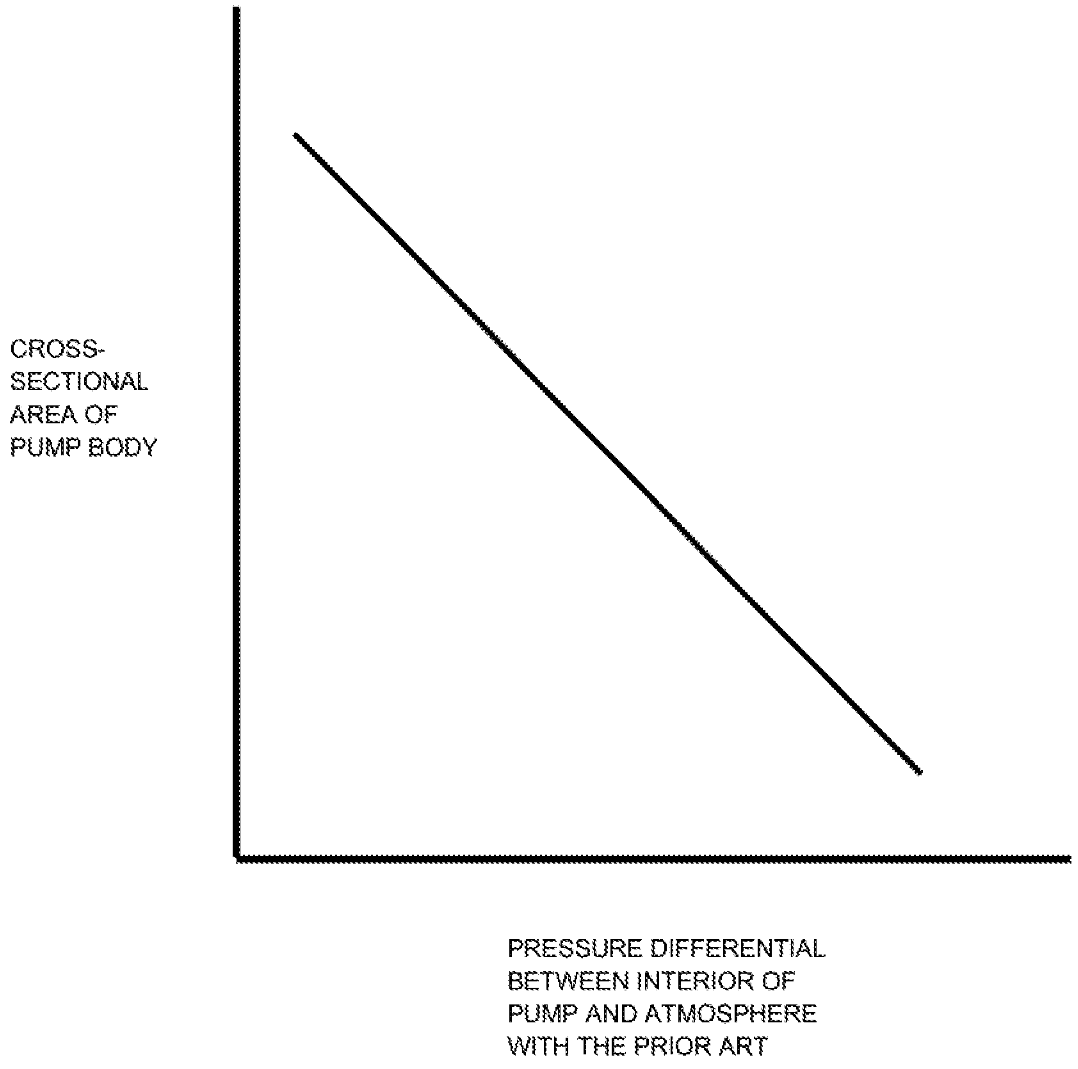
FIG. 8 is a schematic view showing how the pump bodies of the pump assemblies of prior art NPWT bandages gradually change state between their substantially fully expanded configuration and their substantially fully collapsed configuration.
Figure 9:
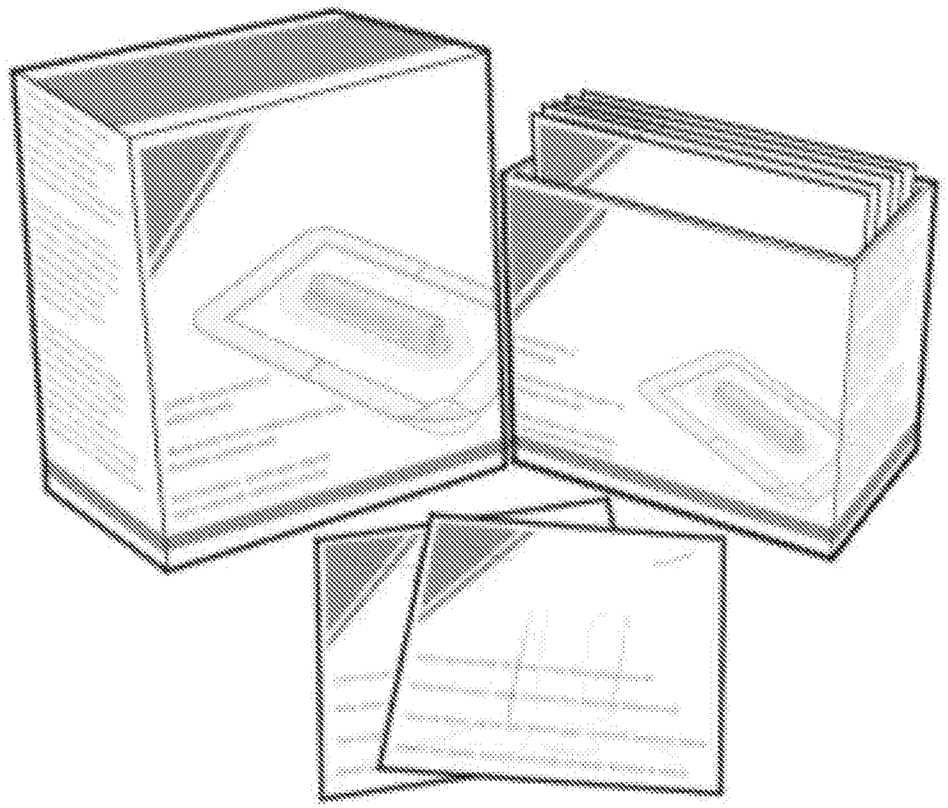
FIGS. 9-16 are schematic views showing exemplary use of the new and improved NPWT bandage shown in FIGS. 1-4 (note that in FIGS. 11 and 14-16, removable cap 100 (see below) is removed from the figures for clarity of illustration)
Figure 10:
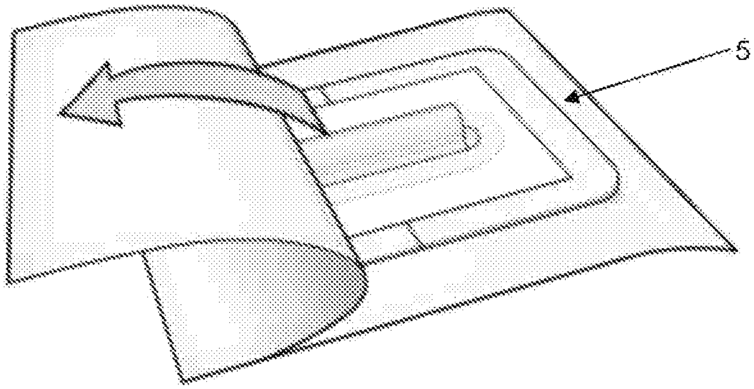

Note also that the prior art approaches of forming the pump body with dome-like or square pump configurations does not provide the pump body with an abrupt change of state—rather, these prior art dome-like or square pump configurations provide the pump body with a more gradual change of state between an expanded configuration and a collapsed configuration when the pressure differential between the pressure of the fluid within an inner chamber and atmospheric pressure changes. See FIG. 8, which is a graph showing the relationship between the diameter of the side wall of a pump body having a dome-like or square configuration and the pressure differential between the pressure of a fluid within an inner chamber of the pump body and atmospheric pressure.

As a result of deliberately configuring side wall 65 of pump body 60 of pump assembly 15 to exhibit this abrupt change of state, pump assembly 15 is able to provide improved pump efficiency, an automatic pressure indicator for indicating the level of negative pressure created, and an automatic pressure limiter for limiting the level of negative pressure created.

More particularly, by configuring pump body 60 of pump assembly 15 so that it will abruptly change state between its substantially fully expanded configuration and its substantially fully collapsed configuration when the pressure differential between the pressure of a fluid within inner chamber 70 and atmospheric pressure crosses a given threshold, pump assembly 15 effectively returns to its substantially fully expanded configuration as long as the pressure differential between the pressure of the fluid within inner chamber 70 and atmospheric pressure is below the given threshold. As a result, so long as the pressure differential between the fluid within inner chamber 70 and atmospheric pressure is below the given threshold, pump assembly 15 returns to its substantially fully expanded configuration between compressions (i.e., squeezes), and hence remains fully efficient as it applies a negative pressure to the wound chamber. This is in contrast to the performance of prior art devices where the pump body exhibits a gradual change of state between an expanded configuration and a collapsed configuration when the pressure differential between the pressure of a fluid within the inner chamber of the pump assembly changes, which makes the pump assembly progressively less efficient as it reduces the pressure within the wound chamber. This is because the pump body will progressively return less and less to its fully expanded configuration as negative pressure is created in the wound chamber, so that the pump assembly is able to evacuate less and less fluid with each squeeze of the pump body. In other words, with prior art devices, the pump assembly becomes less and less efficient as negative pressure is created in the wound chamber.

In a related manner, by configuring pump body 60 so that it will abruptly change state between its substantially fully expanded configuration and its substantially fully collapsed configuration when the pressure differential between the pressure of the fluid within inner chamber 70 and atmospheric pressure crosses a given threshold, pump assembly 15 is able to function as an automatic pressure indicator for indicating the level of negative pressure created, i.e., so long as pump body 60 of pump assembly 15 returns to its substantially fully expanded configuration between squeezes, it will be readily apparent to an observer that the pressure within inner chamber 70 (and hence the pressure within the wound chamber) will be less than a given level. This is in marked contrast to the performance of prior art devices where pump body 60 provides a gradual change of state between an expanded configuration and a collapsed configuration when the pressure differential between the pressure of a fluid within an inner chamber of the pump assembly changes, in which case the pump assembly is not able to function as an automatic pressure indicator for indicating the level of negative pressure created.

And also in a related manner, by configuring pump body 60 so that it will abruptly change state between its substantially fully expanded configuration and its substantially fully collapsed configuration when the pressure differential between the pressure of a fluid within inner chamber 70 and atmospheric pressure crosses a given threshold, pump assembly 15 is able to function as an automatic pressure limiter for limiting the level of negative pressure created since, as soon as pump body 60 assumes its substantially fully collapsed configuration, pump assembly 15 is no longer able to pump fluid from the wound chamber, essentially deactivating the pump assembly. This is in marked contrast to the performance of prior art devices where the pump body provides a gradual change of state between an expanded configuration and a collapsed configuration when the pressure differential between the pressure of a fluid within an inner chamber changes, since the pump assembly is not effectively deactivated at a given pressure differential.

It should be appreciated that the pressure differential required to transition pump body 60 between its substantially fully-expanded configuration and its substantially fully-collapsed configuration (i.e., the aforementioned "given threshold") may be "tuned" (i.e., tailored) to a particular level by varying one or more characteristics of pump body 60, e.g., by forming side wall 65 of pump body 60 out of a material having a particular durometer, by adjusting the thickness of side wall 65 of pump body 60, by adjusting the diameter of inner chamber 70 of pump body 60, etc.

In general, it has been found that excellent therapeutic results may be achieved when the pressure differential required to transition pump body 60 between its substantially fully-expanded configuration and its substantially fully-collapsed configuration (i.e., the aforementioned "given threshold") is between about 60 mm Hg and about 180 mm Hg. In other words, it has been found that excellent therapeutic results may be achieved where pump body 60 transitions between its substantially fully-expanded configuration (FIG. 5) and its substantially fully-collapsed configuration (FIG. 6) at a negative pressure of between about 60 mm Hg and about 180 mm Hg. It is believed that where pump body 60 transitions between its two states at a lower pressure (i.e., where pump body 60 transitions at a negative pressure lower than about 60 mm Hg), not enough suction is provided at the wound site to effectively draw contaminants and microbes away from the wound site and/or to effectively draw exudates away from the wound site and/or to promote beneficial biological responses at the wound site. It is also believed that where pump body 60 transitions between its two states at a higher pressure (i.e., where pump body 60 transitions at a negative pressure higher than about 180 mm Hg), the suction provided at the wound site may cause trauma to the tissue (e.g., blistering, capillary leakage, etc.).

In one preferred form of the invention, pump body 60 of pump assembly is configured so that it abruptly transitions between its substantially fully expanded configuration and its substantially fully collapsed configuration when the pressure differential between the pressure of the fluid within inner chamber 70 and atmospheric pressure exceeds 80 mm Hg. Thus, in this form of the invention, as long as the negative pressure within the wound chamber is less than 680 mm Hg (assuming atmospheric pressure is 760 mm Hg), pump assembly 15 returns to its substantially fully expanded configuration between squeezes of the pump body and maintains its pump efficiency as it applies suction to the wound chamber, and as soon as the negative pressure within the wound chamber exceeds 680 mm Hg (assuming atmospheric pressure is 760 mm Hg), pump assembly 15 will assume its substantially fully collapsed configuration, acting as an automatic pressure indicator to indicate that the level of negative pressure created at the wound site has exceeded 80 mm Hg and automatically deactivating pump assembly 15 so that the level of negative pressure created at the wound site cannot exceed 80 mm Hg.

Note that inasmuch as pump body 60 of pump assembly 15 has a substantially cylindrical configuration, NPWT bandage 5 has a low profile.

Note also that inasmuch as pump body 60 of pump assembly 15 is configured to be squeezed between the thumb and forefinger of a user, the compressive force being applied to pump body 60 is applied parallel to the surface of the skin, so that no trauma is applied to the wound during use (i.e., during pumping of pump assembly 15). This is in marked contrast to prior art NPWT bandages which employ a dome-like configuration and require the compressive force to be applied toward the wound.

Exemplary Use

In one preferred form of the invention, and looking now at FIGS. 9-16, NPWT bandage 5 is intended to be used as follows.

First, an NPWT bandage 5 is removed from its box. In one form of the invention, each individual NPWT bandage 5 is contained in a separate sterile package, with multiple sterile packages contained in a box. See FIG. 9.

Figure 11:
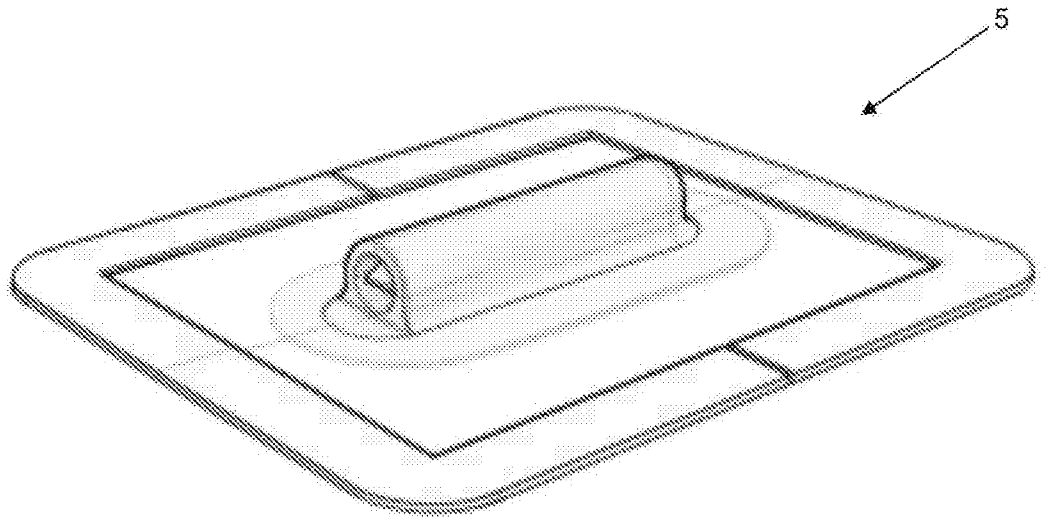
Figure 12:
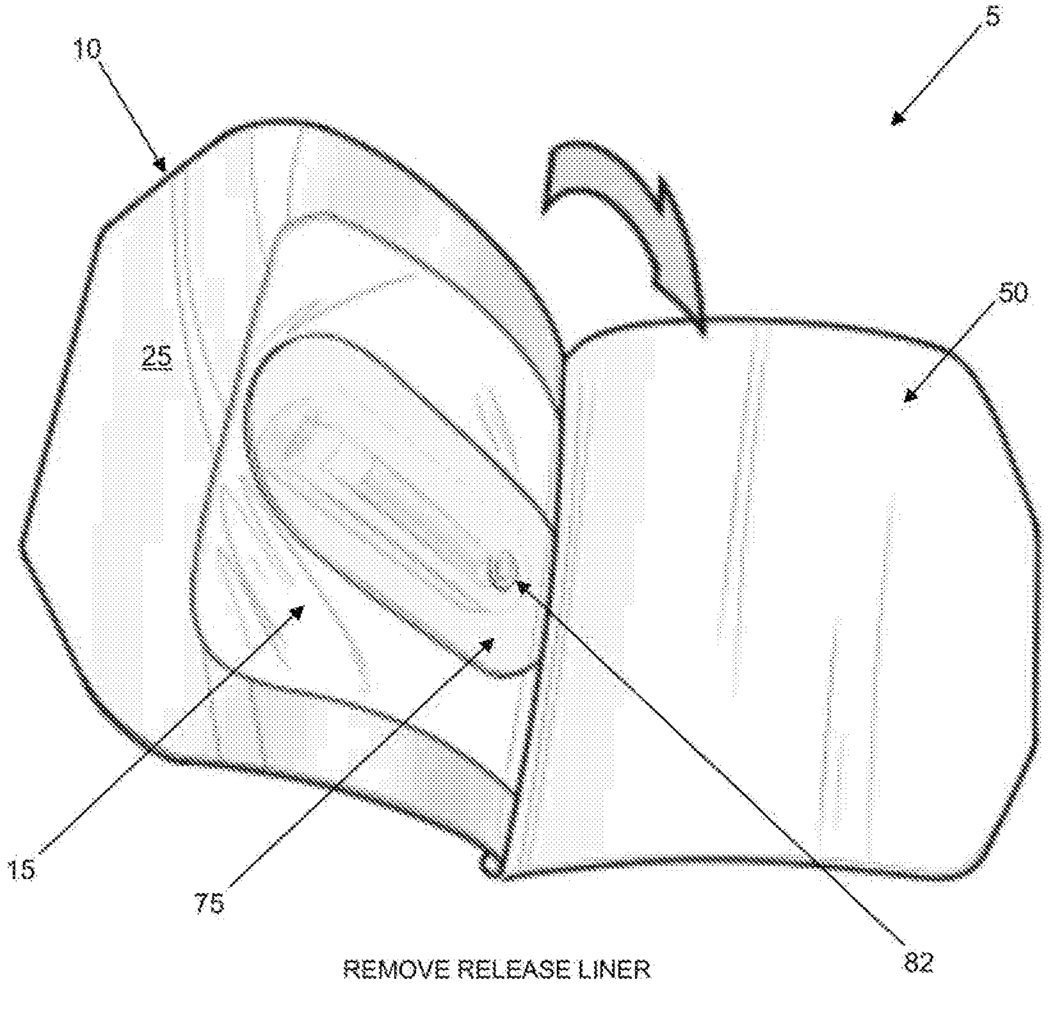
Figure 13:
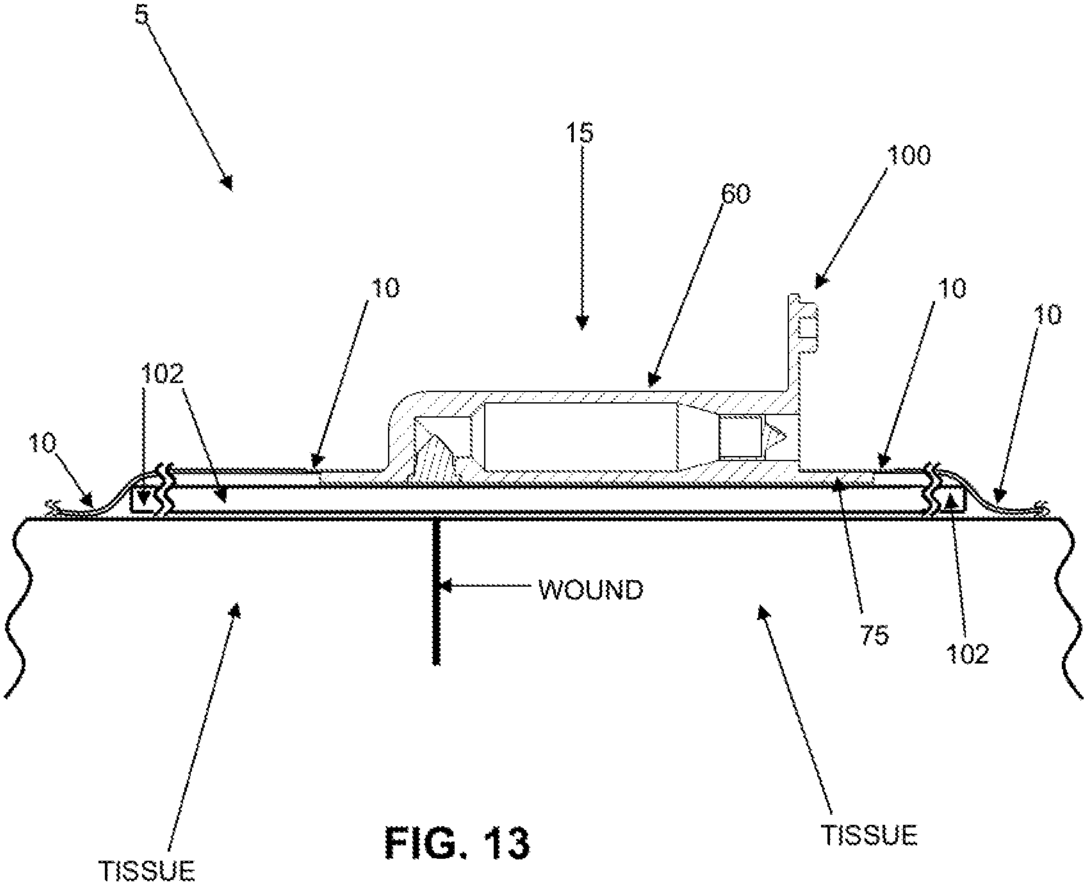
Figure 14:
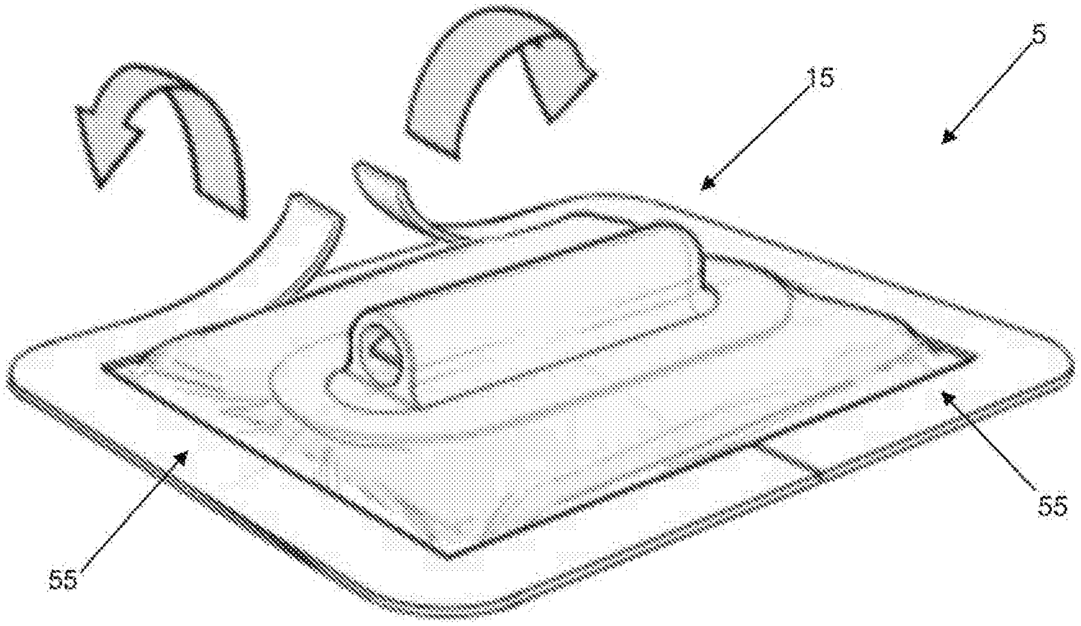
Figure 15:
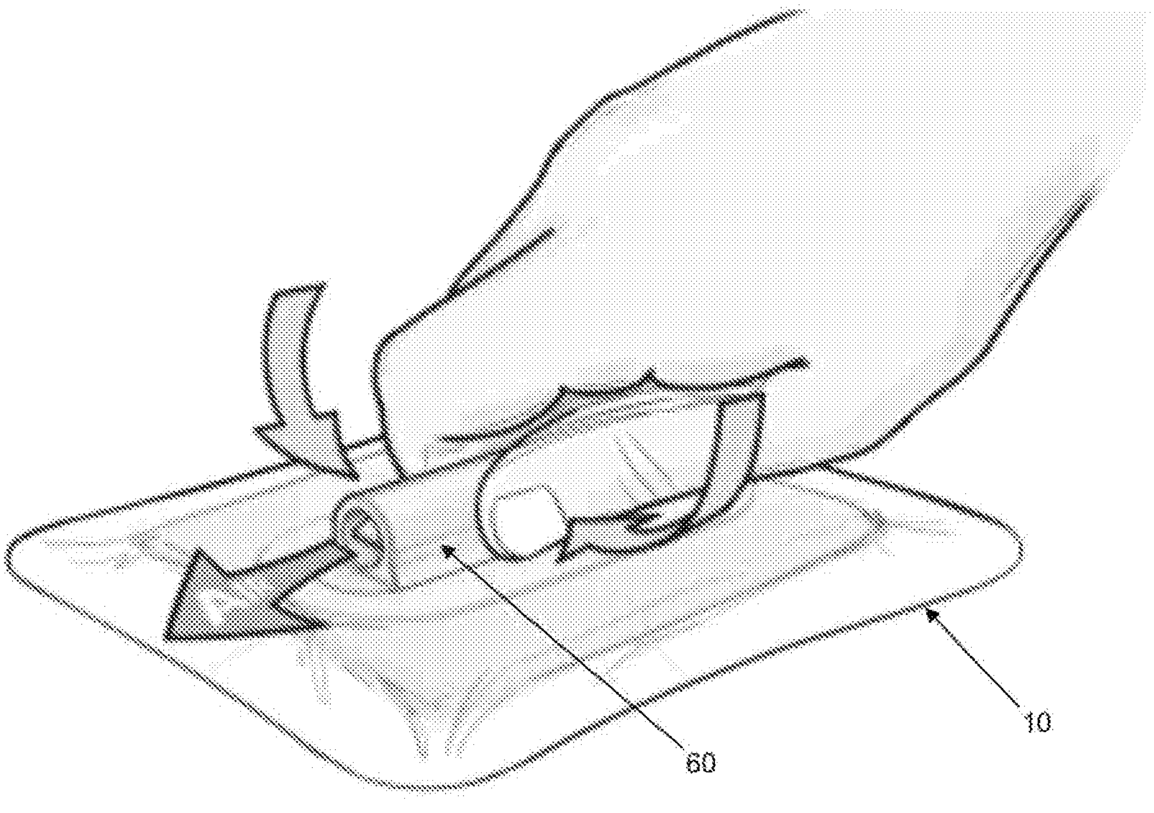
Figure 16:
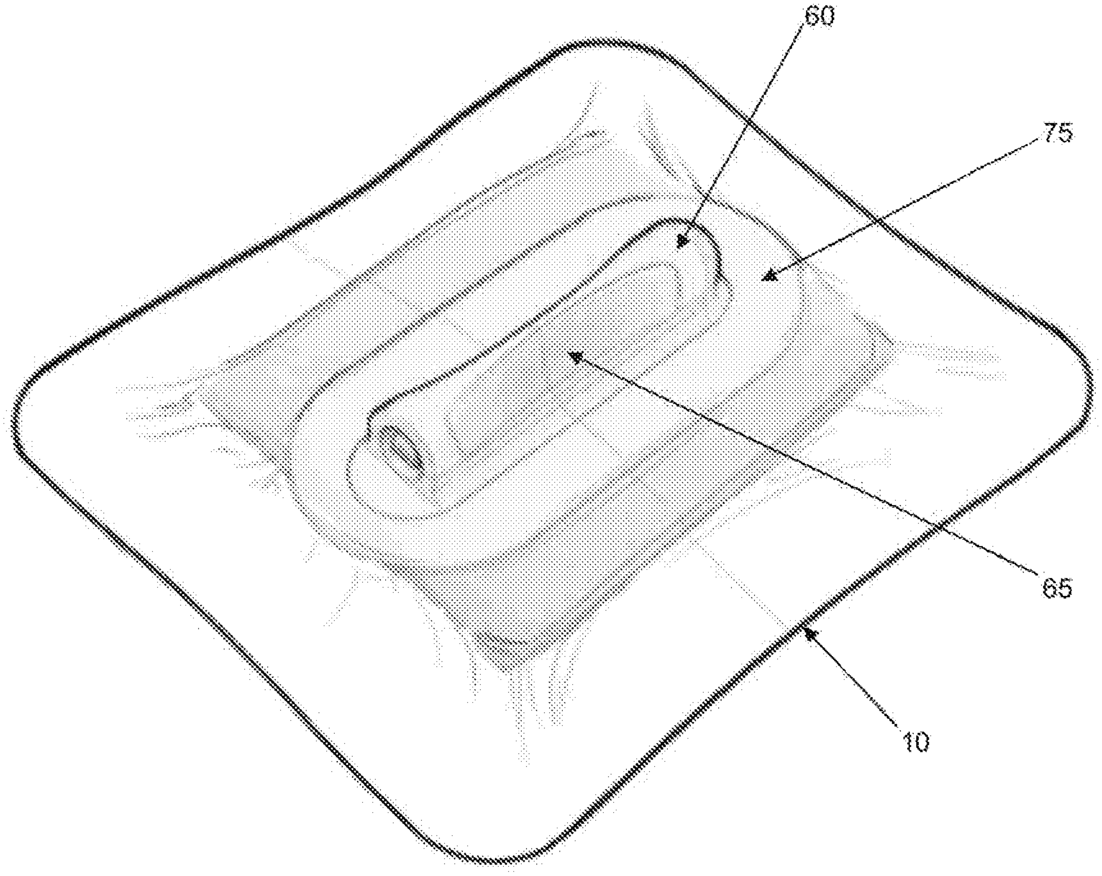
Figure 17:
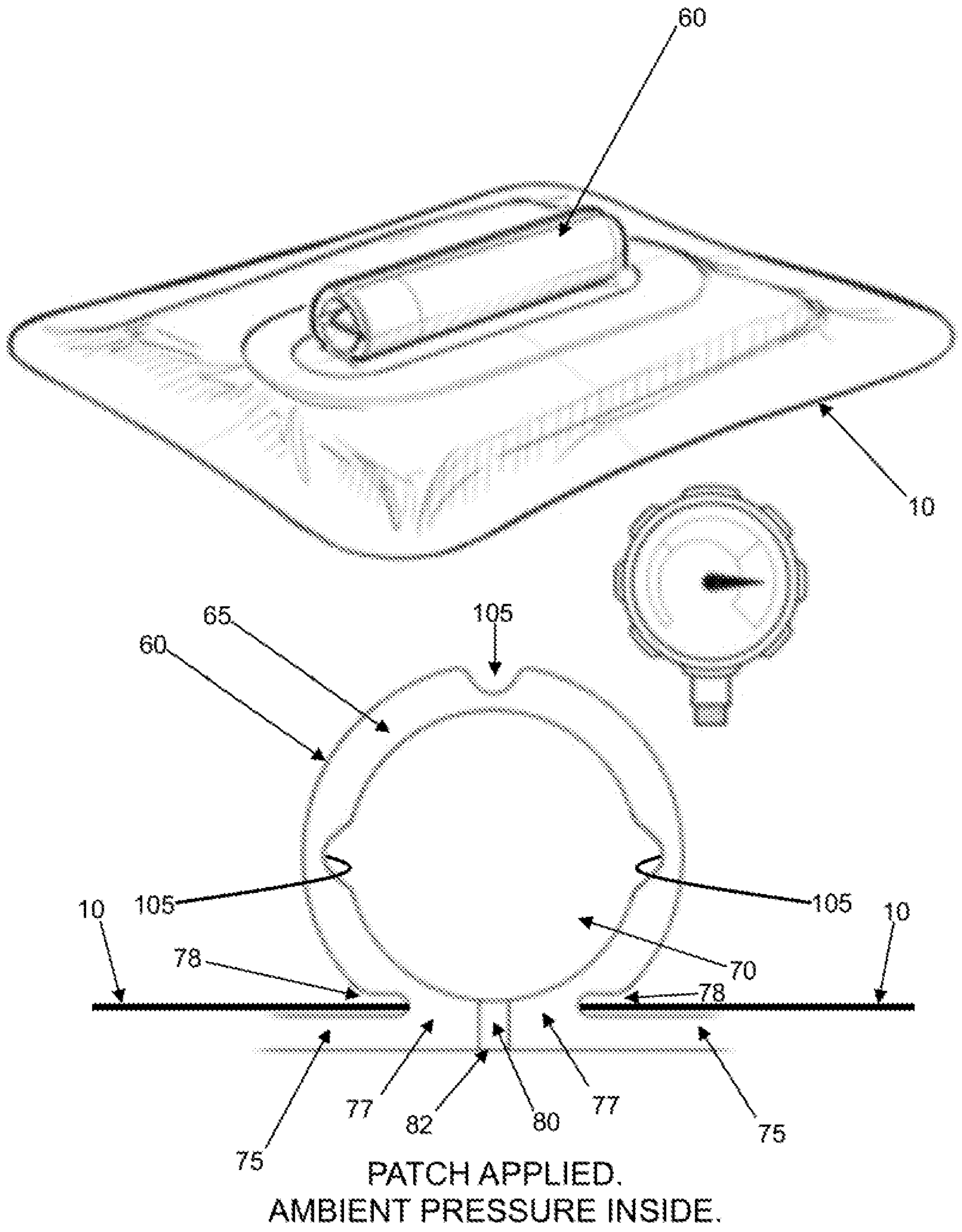
FIGS. 17-20 are schematic views showing another new and improved NPWT bandage formed in accordance with the present invention.
Figure 18:
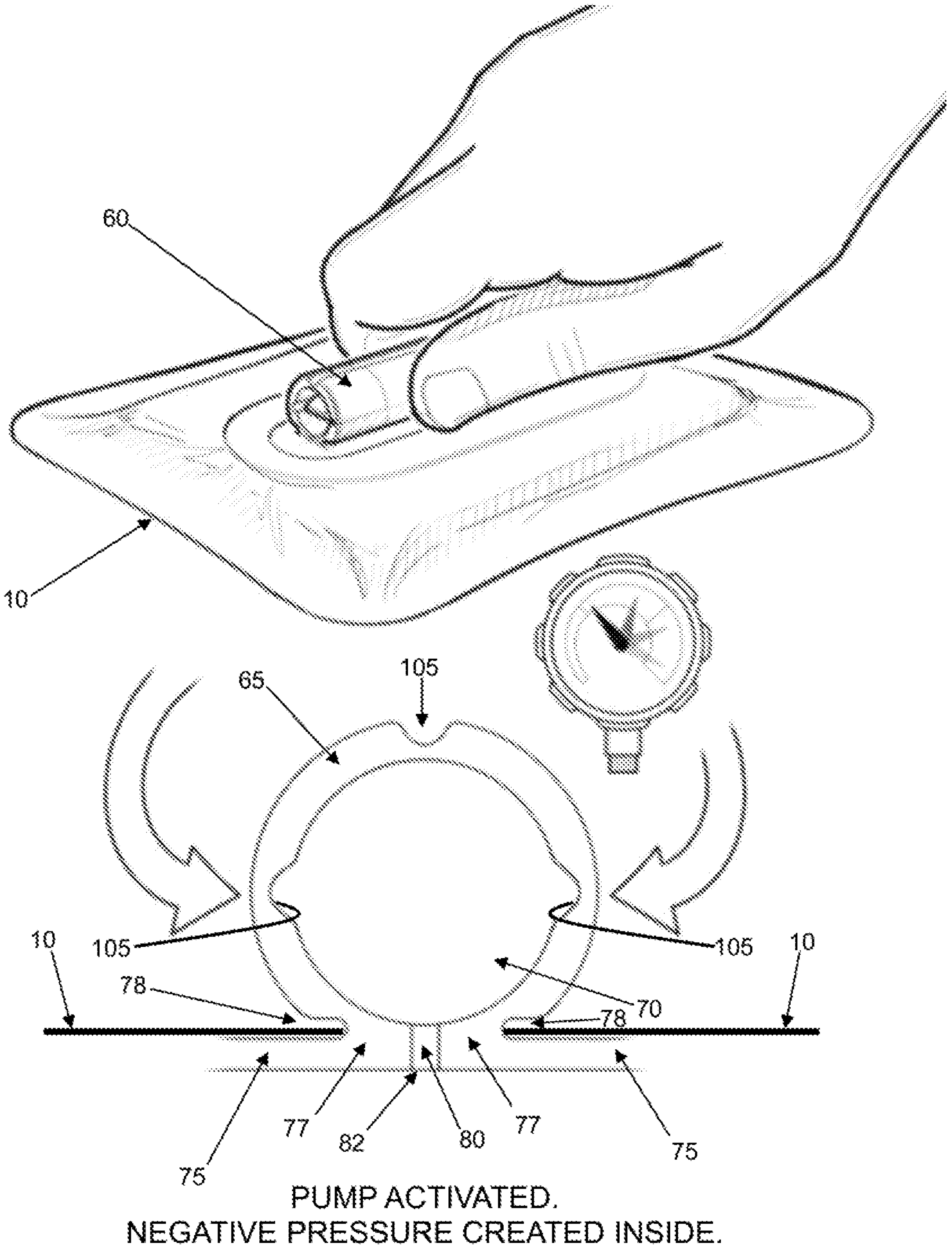
Figure 19:
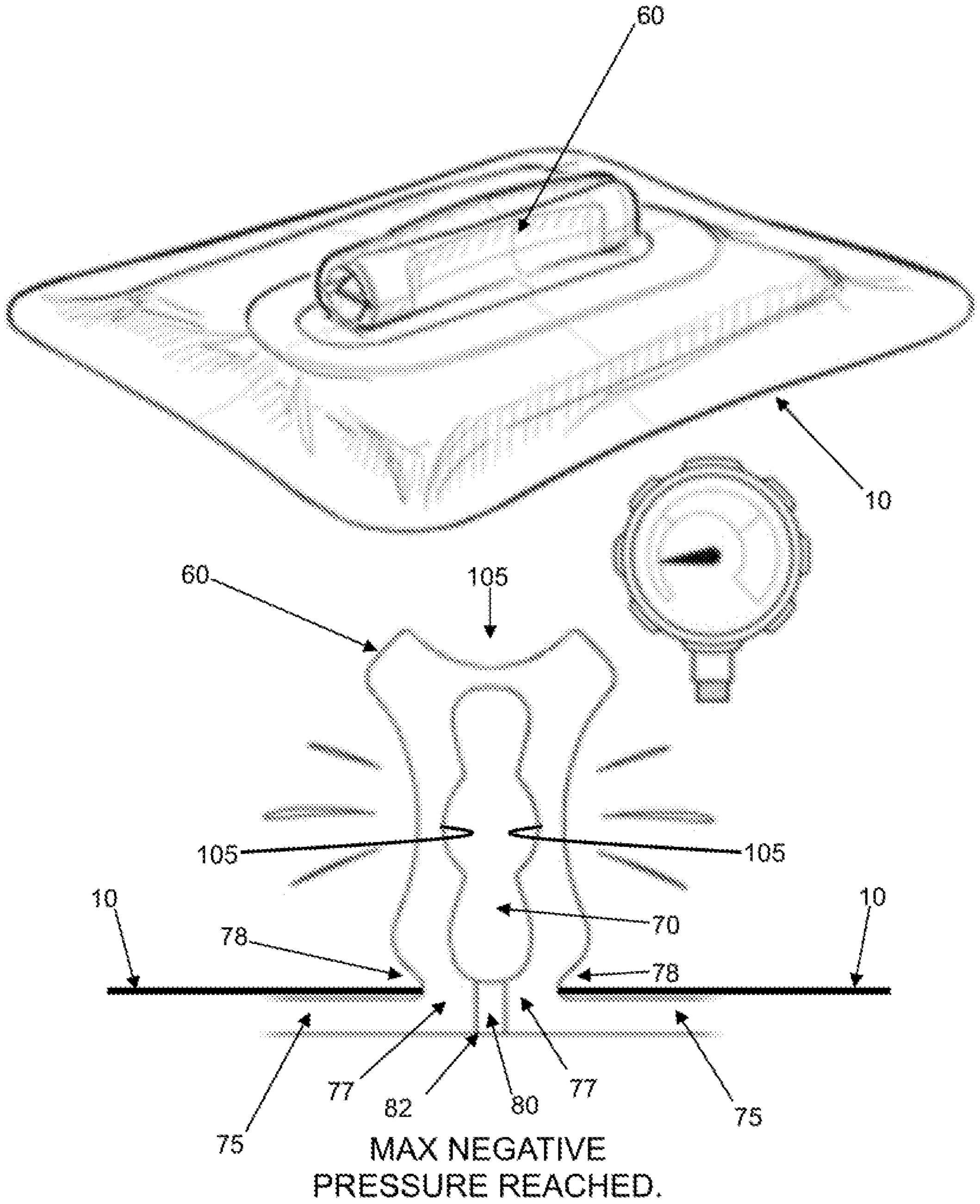

Next, an NPWT bandage 5 is removed from its sterile package (FIG. 10) so as to be ready for use (FIG. 11).

In order to apply NPWT bandage 5 to the wound site, release liner 50 is removed from wound-side surface 25 of membrane 10. See FIG. 12. Then NPWT bandage 5 is positioned against the skin of a patient so that wound-side surface 25 of membrane 10 is positioned against the wound, with adhesive 45 securing NPWT bandage 5 to the skin of the patient, thereby forming a substantially air-tight seal with the skin of the patient about the perimeter of the wound chamber. See FIG. 13.

Note that when NPWT bandage 5 is applied to the skin of the patient, wound-side port 82 of wound-side passageway 80 of pump assembly 15 is open to the wound chamber.

Note also that a layer of gauze (or other absorbent wound dressing) 102 may be placed on the wound site prior to placing NPWT bandage 5 on the skin of the patient, so that the layer of gauze (or other absorbent wound dressing) is interposed between the wound and wound-side passageway 80 of pump assembly 15. As a result, exudate emerging from the wound will be taken up by the gauze (or other absorbent wound dressing). Note that, if desired, the layer of gauze (or other absorbent wound dressing) 102 may be mounted to (i.e., secured to) the wound-side surface of membrane 10, e.g., such as at the time of manufacture, so that the layer of gauze (or other absorbent wound dressing) 102 is carried to the wound site by NPWT bandage 5 and is applied to the wound at the same time as the NPWT bandage 5.

Next, with NPWT bandage 5 secured to the skin of the patient, removable stiffener 55 is removed from atmosphere-side surface 30 of membrane 10. See FIG. 14.

At this point, NPWT bandage 5 may be used to apply negative pressure to the wound chamber. This is done by squeezing side wall 65 of pump body 60 between the thumb and forefinger of a user so as to compress pump body 60 into its substantially fully collapsed configuration, whereby to expel fluid (e.g., air, liquid, etc.) from inner chamber 70 of pump body 60 via atmosphere-side passageway 85 and atmosphere-side one-way valve 95. See FIG. 15. Note that fluid in inner chamber 70 of pump body 60 is prevented from exiting inner chamber 70 through wound-side passageway 80 due to the presence of wound-side one-way valve 90. Then side wall 65 of pump body 60 is released, allowing the resilient pump body 60 to return to its substantially fully expanded configuration, thereby creating a negative pressure within inner chamber 70 and wound-side passageway 80, such that fluid below wound-side surface 25 of membrane 10 (e.g., fluid within the wound chamber) is drawn into inner chamber 70 through wound-side passageway 80 and wound-side one-way valve 90. Note that air in the atmosphere is prevented from entering inner chamber 70 through atmosphere-side passageway 85 due to the presence of atmosphere-side one-way valve 95.

This process of squeezing and releasing side wall 65 of pump body 60 is repeated until pump body 60 of pump assembly 15 remains in its substantially fully collapsed configuration (i.e., side wall 65 of pump body 60 bows inwardly) even when side wall 65 of pump body 60 is not being manually compressed. See FIG. 16. When pump body 60 of pump assembly 15 remains in its substantially fully collapsed configuration even when side wall 65 of pump body 60 is not being manually compressed, an observer will know that the pressure differential between the pressure of the fluid within inner chamber 70 (and the wound chamber) and atmospheric pressure exceeds the desired threshold, indicating that the desired level of negative pressure has been achieved at the wound site. Note that when pump body 60 of pump assembly 15 remains in its substantially fully collapsed configuration even when side wall 65 of pump body 60 is not being manually compressed, pump assembly 15 will have been effectively deactivated, since it will be impossible to continue using the pump assembly with side wall 65 in its substantially fully collapsed configuration.

At this point removable cap 100 may be used to seal atmosphere-side port 87 of atmosphere-side passageway 85.

NPWT bandage 5 is left in place on the wound for an appropriate period of time (e.g., a few days) so as to shield the wound from contaminants and microbes during healing, draw exudates out of the wound, and promote beneficial biological responses at the wound site. In the event that leakage should cause the negative pressure created in the wound chamber to fall below the given threshold (which will be apparent to an observer by virtue of the fact that side wall 65 of pump body 60 will return to its substantially fully-expanded configuration), atmosphere-side port 87 of atmosphere-side passageway 85 may be unsealed (i.e., by removing removable cap 100) and then pump assembly 15 may be used in the manner discussed above to re-establish the desired negative pressure in the wound chamber (i.e., by repeatedly squeezing and releasing side wall 65 of pump body 60).

When appropriate, NPWT bandage 5 may be removed from the skin of the patient by simply peeling membrane 10 away from the skin of the patient.

Pump Body with Notches to Enhance the Substantially "Binary State" Behavior of the Pump Body As noted above, pump body 60 of pump assembly 15 is preferably specifically configured so that the pump body will abruptly change state between (i) a substantially fully expanded configuration where side wall 65 of pump body 60 and inner chamber 70 of pump body 60 have a substantially circular cross-section (see FIG. 5) when the pressure differential between the pressure of the fluid within inner chamber 70 and atmospheric pressure is below a given threshold, and (ii) a substantially fully collapsed configuration where side wall 65 of pump body 60 bows inwardly (see FIG. 6) when the pressure differential between the pressure of the fluid within inner chamber 70 and atmospheric pressure exceeds a given threshold.

As also noted above, this substantially "binary state" behavior of pump body 60 is achieved by forming the pump body with a substantially circular cross-section, which gives the body an "over-the-center" deformation characteristic, i.e., so that the side wall of pump body 60 has a "failure" mode where it abruptly transitions from a substantially fully expanded configuration to a substantially fully collapsed configuration, and has a "restoration" mode where it abruptly transitions from a substantially fully collapsed configuration to a substantially fully expanded configuration. See FIG. 7. As noted above, by forming pump assembly 15 so that side wall 65 of pump body 60 and pump flange 75 merge at a neck 77 (FIG. 5), with neck 77 having a relatively small width relative to the full diameter of pump body 60, and with recesses 78 extending inwardly between membrane 10 and pump body 60, pump body 60 has a substantially circular cross-section over substantially its entire circumference, with pump body 60 free to radially compress/radially expand with minimal interference from pump flange 75, so that pump body 60 can exhibit substantially "binary state" behavior.

If desired, pump body 60 can be modified so as to enhance the substantially "binary state" behavior of the pump body.

By way of example but not limitation, and looking now at FIGS. 17-20, notches 105 can be formed in pump body 60 (e.g., at the "9 o'clock", "12 o'clock" and "3 o'clock" positions) so as to enhance the substantially "binary state" behavior of the pump body by further inducing pump body 60 to assume only its substantially fully expanded configuration or its substantially fully collapsed configuration. Note that the more that pump body 60 exhibits true "binary state" behavior, the more that pump efficiency will improve and the better that pump assembly 15 will serve as an automatic pressure indicator and as an automatic pressure limiter.

Figure 20:
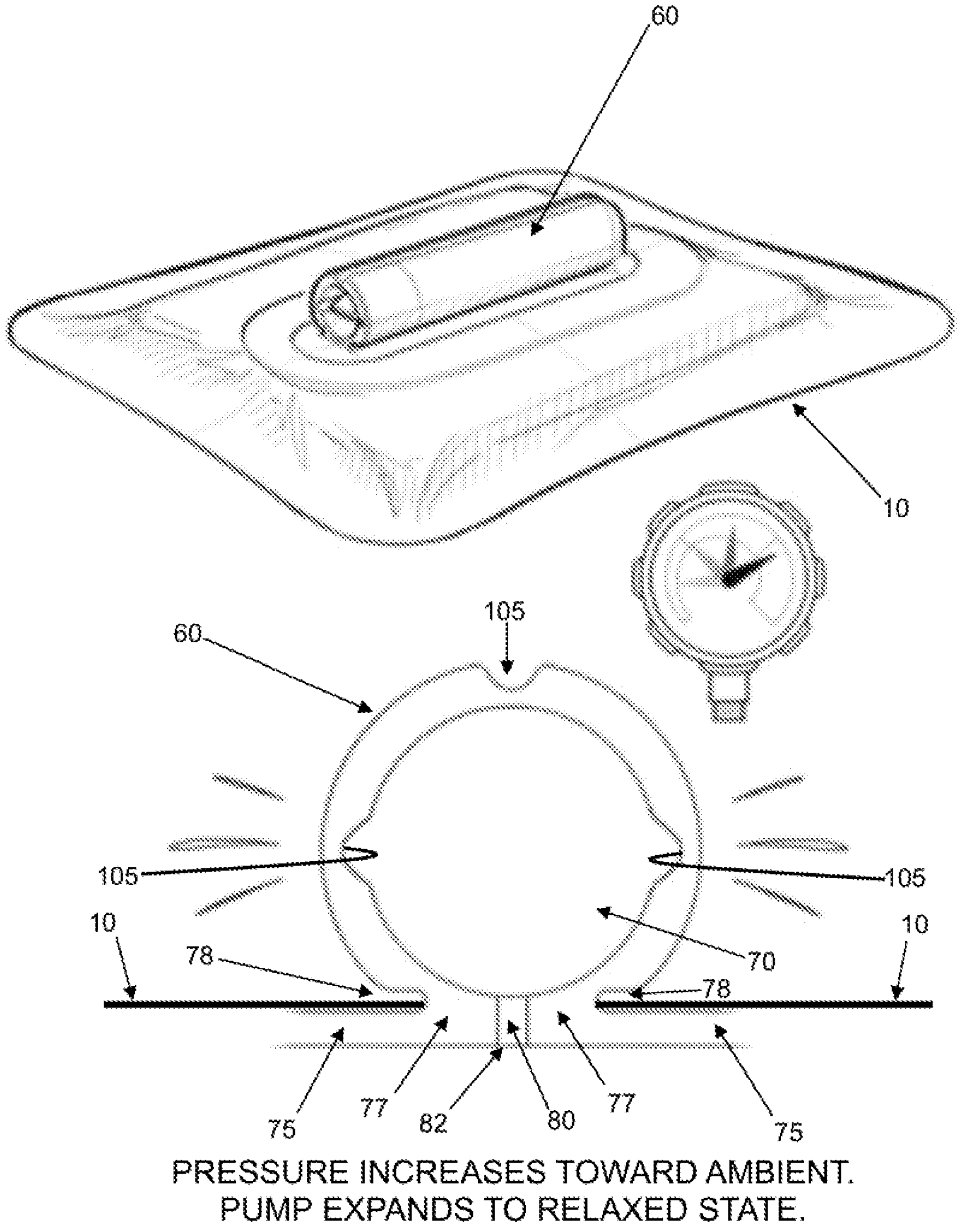
Figure 20A:
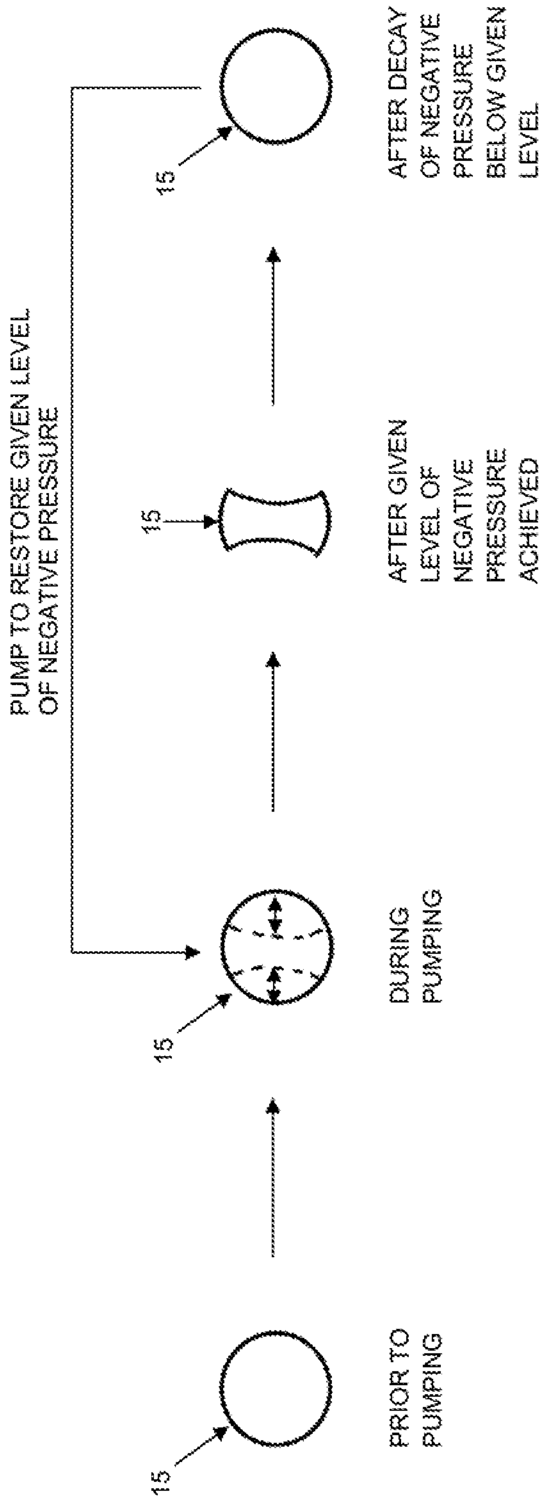
FIG. 20A is a schematic view showing how the configuration of the pump body changes during use (note that in FIG. 20A, only the outer boundary of the pump's side wall 65 is shown, and the pump's flange 75 and neck 77 are omitted, for clarity of illustration)
Figure 21:
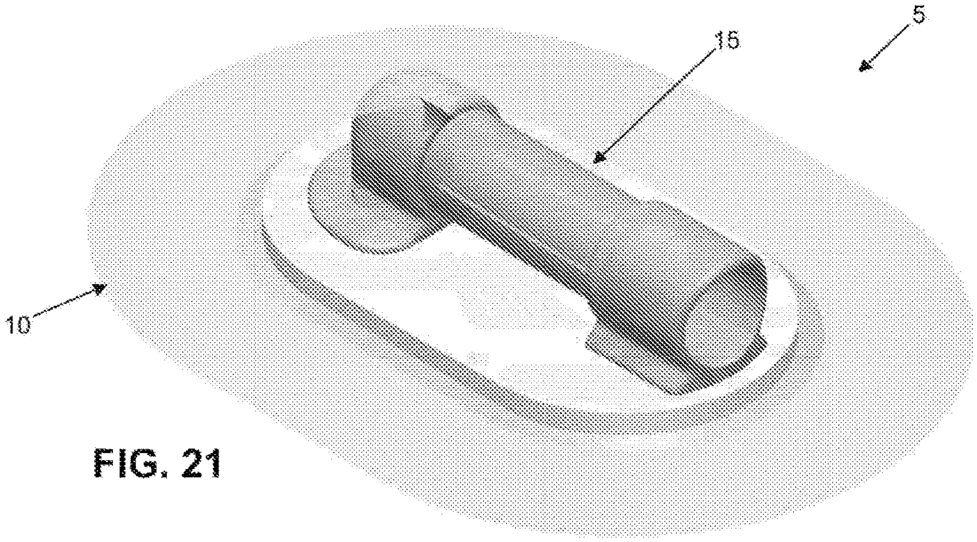
FIGS. 21-25 are schematic views showing another new and improved NPWT bandage formed in accordance with the present invention.
Figure 22:
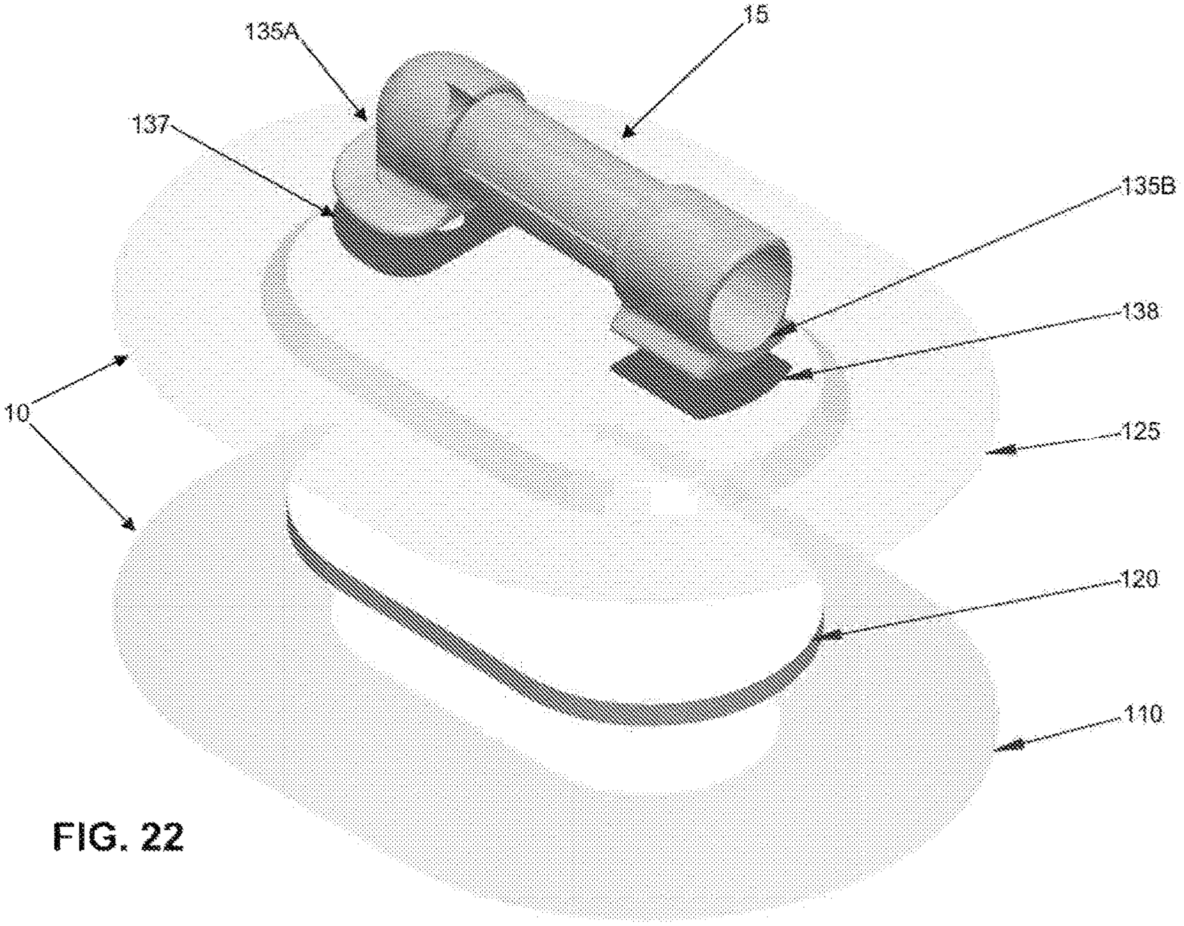
Figure 23:
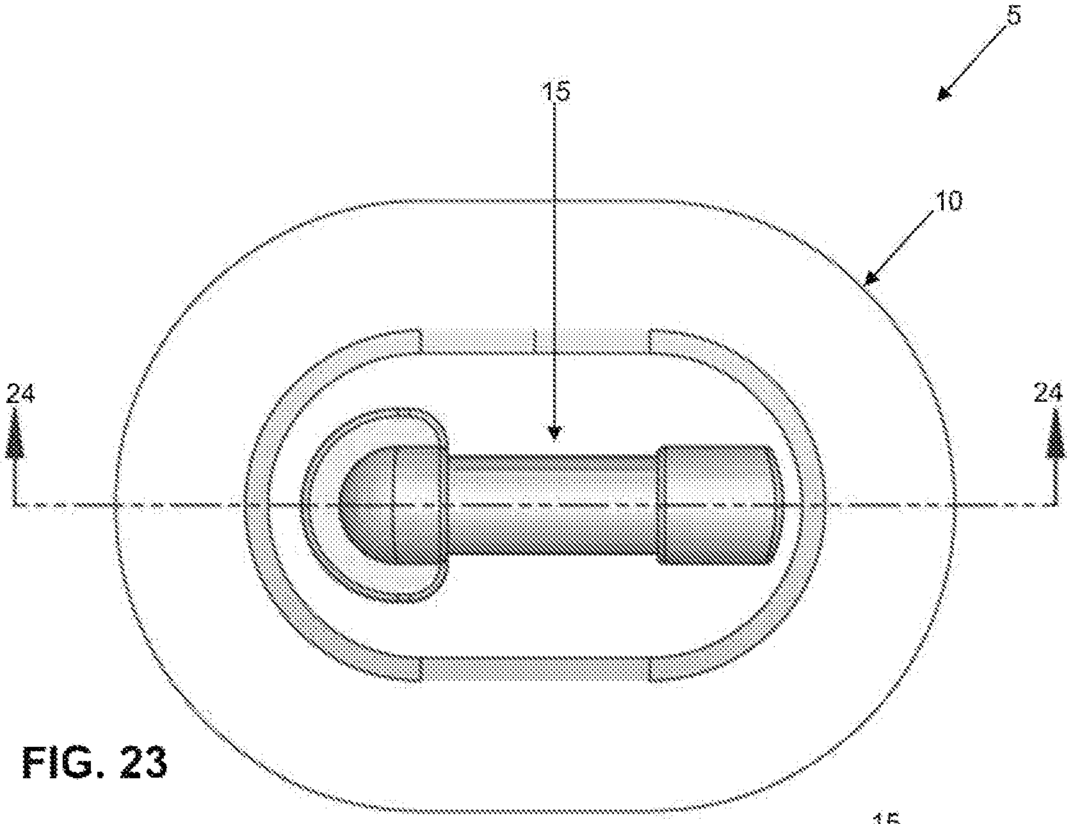
Figure 24:
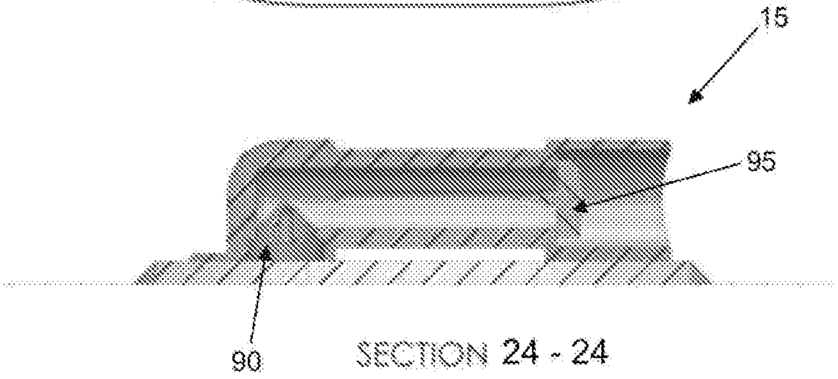
Figure 25:
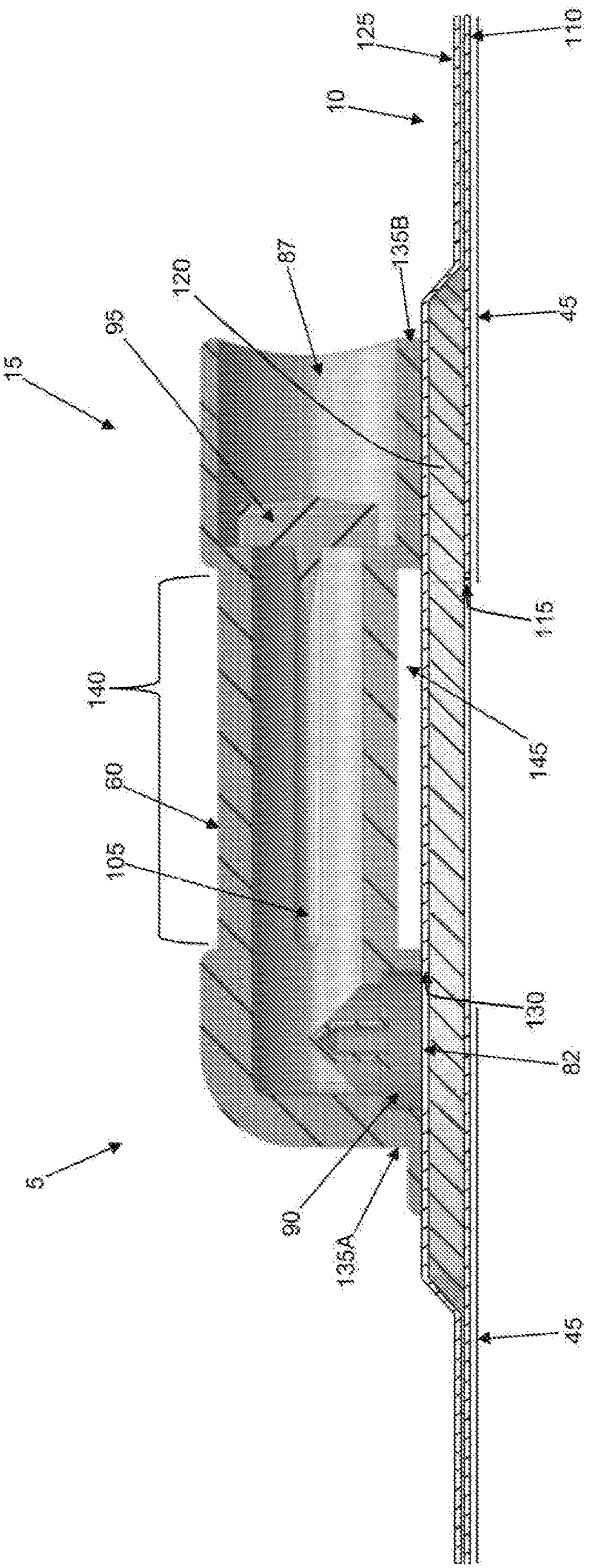

Thus it will be seen that, and looking now at FIG. 20A, pump body 60 generally has:

- a substantially fully expanded configuration prior to pumping;
- a collapsing and expanding configuration during pumping;
- a "vertically-oriented" substantially collapsed configuration after a given level of negative pressure has been achieved by pumping; and
- a substantially fully expanded configuration after the negative pressure has decayed below a given level.

Furthermore, the desired negative pressure can be re-established after transition to the substantially fully expanded configuration by renewed pumping.

NPWT Bandage Incorporating Gauze (or Other Absorbent Wound Dressing) and Utilizing an Improved Pump Assembly Looking next at FIGS. 21-25, there is shown another negative pressure wound therapy (NPWT) bandage 5 formed in accordance with the present invention. The NPWT bandage 5 shown in FIGS. 21-25 is substantially the same as the NPWT bandage 5 shown in FIGS. 1-16, and the NPWT bandage 5 shown in FIGS. 17-20, except that (i) in the construction shown in FIGS. 21-25, membrane 10 comprises multiple layers which incorporate gauze (or other absorbent wound dressing), and (ii) in the construction shown in FIGS. 21-25, pump assembly 15 has a modified construction and is secured to membrane 10 using a different approach.

More particularly, in this form of the invention, membrane 10 comprises a lower skin-contacting polyurethane layer 110 having a center opening 115, an intermediate foam (or gauze or other absorbent wound dressing) layer 120 for disposition over center opening 115 of lower skin-contacting polyurethane layer 110, and an upper polyurethane layer 125 for disposition over intermediate foam layer 120 and lower skin-contacting polyurethane layer 110. In the preferred form of the invention, upper polyurethane layer 125 is formed out of a substantially air-impermeable material. And, in the preferred form of the invention, upper polyurethane layer 125 and lower skin-contacting polyurethane layer 110 have the same size outer perimeter, so that upper polyurethane layer 125 does not contact the skin of the patient. The outer perimeters of upper polyurethane layer 125 and lower skin-contacting polyurethane layer 110 are secured to one another, capturing intermediate foam layer 120 therebetween. Intermediate foam layer 120 has an outer perimeter which is (i) larger than the perimeter of center opening 115 of lower skin-contacting polyurethane layer 110, and (ii) smaller than the outer perimeter of the outer perimeters of lower skin-contacting polyurethane layer 110 and upper polyurethane layer 125. In this way, when NPWT bandage 5 has its center opening 115 of lower skin-contacting polyurethane layer 110 positioned over a wound, fluid from the wound can pass through center opening 115 of lower skin-contacting polyurethane layer 110 to reach intermediate foam layer 120. It will be appreciated that adhesive 45 is positioned on the wound side surface of lower skin-contacting polyurethane layer 110 so that a substantially air-tight seal may be established by NPWT bandage 5 about the perimeter of a wound (i.e., so as to form the aforementioned wound chamber). An opening 130 is formed in upper polyurethane layer 125, and overlaps center opening 115 of lower skin-contacting polyurethane layer 110, so that wound-side passageway 80 of pump assembly 15 can access fluid (e.g., air, liquid, etc.) within the wound chamber (i.e., via opening 130 in upper polyurethane layer 125, the openings in intermediate foam layer 120, and center opening 115 of lower skin-contacting polyurethane layer 110) for evacuation during pumping of pump assembly 15.

The pump assembly 15 utilized in the NPWT bandage 5 of FIGS. 21-25 is generally similar to the pump assembly 15 described above, except that it comprises a pair of pedestals 135A, 135B for mounting pump assembly 15 to membrane 10. More particularly, pedestal 135A comprises one end of pump body 60 and is adhered (e.g., by an adhesive 137) to the upper surface of membrane 10 (i.e., to the upper surface of upper polyurethane layer 125) so that wound-side passageway 80 and wound-side one-way valve 90 are aligned with opening 130 in upper polyurethane layer 125 (and hence in fluid communication with the wound chamber). Pedestal 135B comprises the other end of pump body 60 and is adhered (e.g., by an adhesive 138) to the upper surface of membrane 10 (i.e., to the upper surface of upper polyurethane layer 125). The intervening portion 140 of pump body 60 sits suspended between pedestal 135A and pedestal 135B, elevated above upper polyurethane layer 125 of membrane 10, so that a space 145 is formed between intervening portion 140 of pump body 60 and upper polyurethane layer 135 of membrane 10. Inasmuch as intervening portion 140 of pump body 60 is not mounted directly to membrane 10, but is instead suspended above membrane 10 by means of pedestals 135A and 135B, intervening portion 140 of pump body 60 can be formed with a true circular cross-section, whereby to enhance the substantially "binary state" behavior of the NPWT bandage. It will be appreciated that pump body 60 may incorporate one or more of the aforementioned notches 105 so as to further enhance the substantially "binary state" behavior of the NPWT bandage.

NPWT Bandage with Negative Pressure Decay "Warning State" Indicator

It has also been discovered that, if desired, pump body 60 can be configured to provide a negative pressure decay "warning state" indicator.

More particularly, by controlling the number, configuration and disposition of notches 105, pump body 60 can provide a "warning state" indicator to indicate that a decay of the negative pressure has occurred, albeit not enough of a decay to cause the binary state transition of the pump body (i.e., from a substantially collapsed configuration to a substantially fully expanded configuration). By way of example but not limitation, by providing a pump body having notches 105 which are appropriate in number, configuration and disposition, the pump body can provide a "warning state" indicator (to indicate that there is a decay of the negative pressure below a given level, albeit not enough of a decay to cause a binary state transition of the pump body from substantially fully collapsed to substantially fully expanded) by transitioning the pump body from its "vertically-oriented" substantially collapsed configuration (which occurs after a given level of negative pressure has been achieved) to a "horizontally-oriented" substantially collapsed configuration (which occurs after there has been some decay of the negative pressure, albeit not enough of a decay to cause a binary state transition of the pump body back to a substantially fully expanded configuration).

Figure 27:
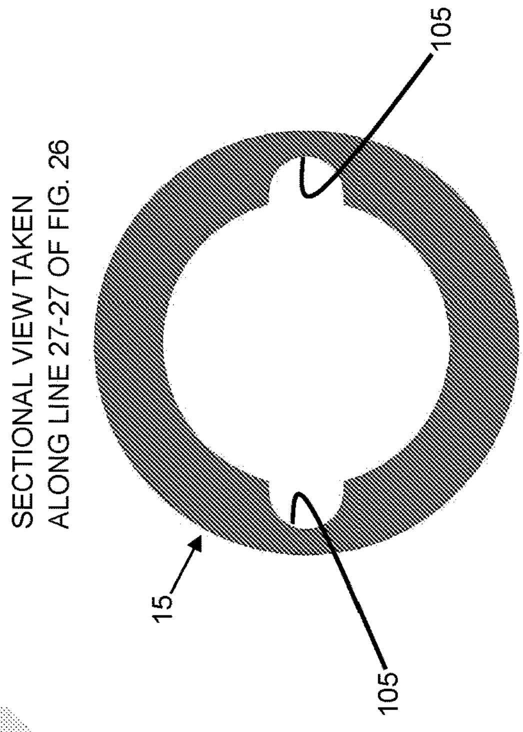
FIGS. 26 and 27 are schematic views showing another new and improved NPWT bandage formed in accordance with the present invention, wherein the pump body is constructed so that it also provides a negative pressure decay “warning state” indicator.
Figure 26:
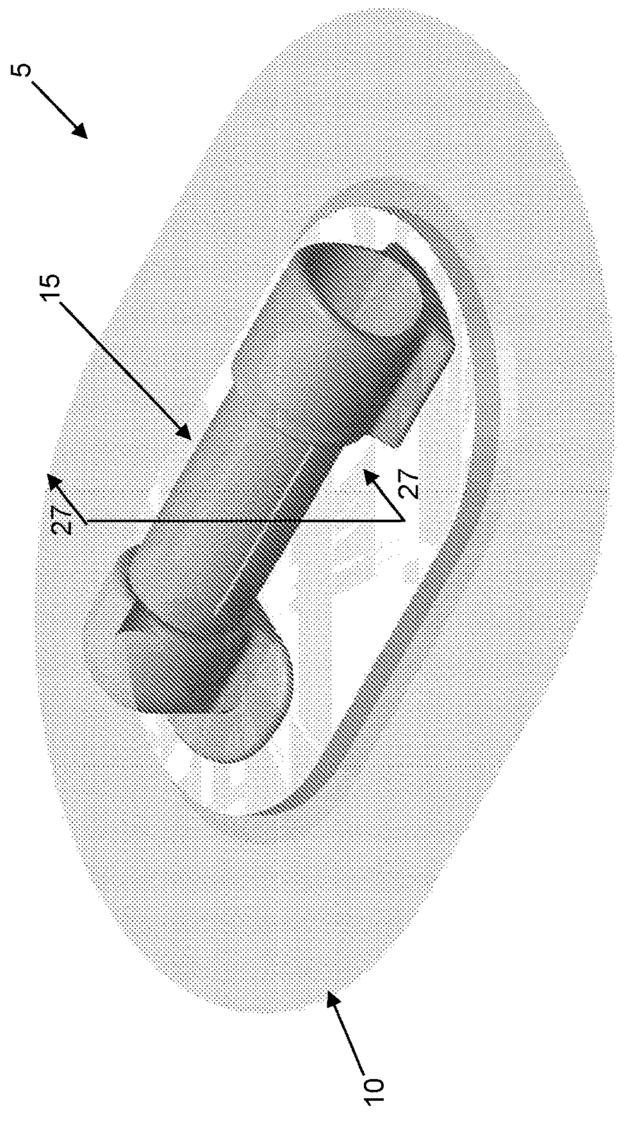

FIGS. 26 and 27 show an exemplary construction wherein a pump body, having notches 105 which are appropriate in number, configuration and disposition, can provide a "warning state" indicator (to indicate that there is a decay of the negative pressure below a given level, albeit not enough of a decay to cause a binary state transition of the pump body to a fully expanded configuration) by transitioning the pump body from its "vertically-oriented" substantially collapsed configuration (which occurs after a given level of negative pressure has been achieved) to a "horizontally-oriented" substantially collapsed configuration (which occurs after there has been some decay of the negative pressure, albeit not enough of a decay to cause a binary state transition of the pump body back to a substantially fully expanded configuration).

Figure 28:
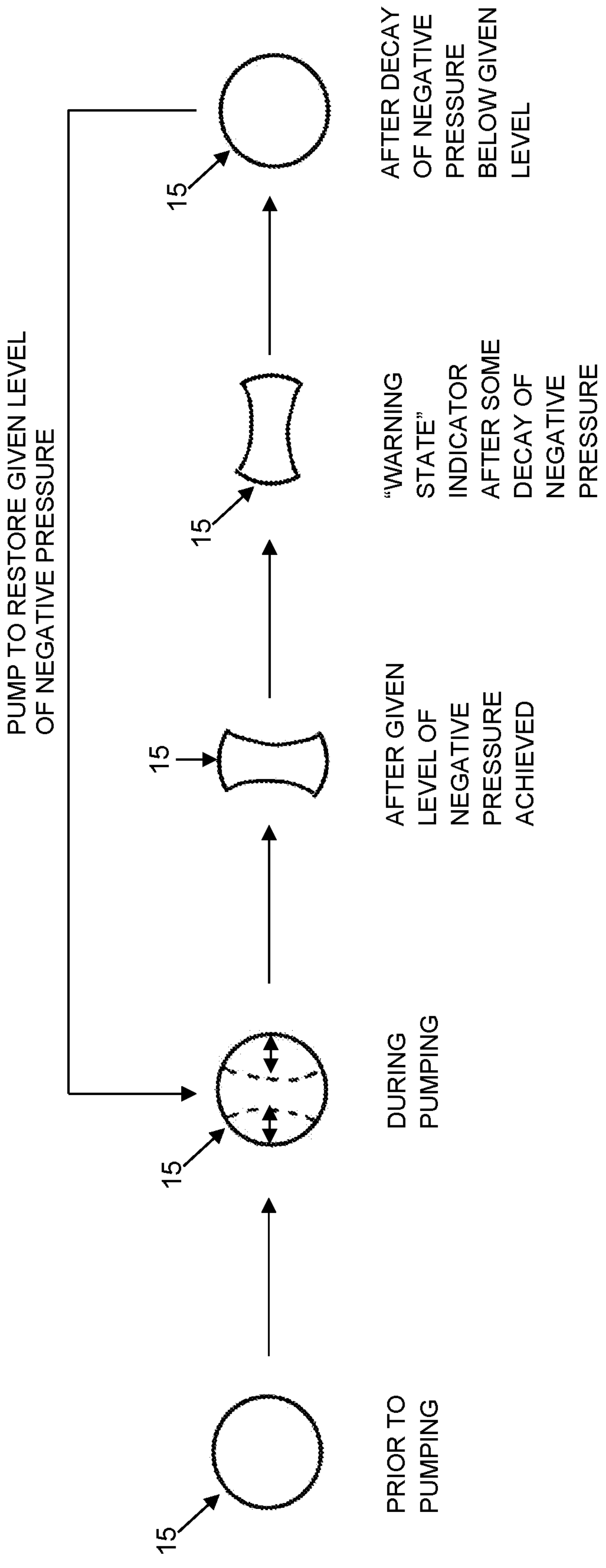
FIG. 28 is a schematic view showing how the configuration of the pump body comprising a negative pressure decay “warning state” indicator changes during use (note that in FIG. 28, only the outer boundary of the pump's side wall is shown, for clarity of illustration)

Thus it will be seen that, in this form of the invention, and looking now at FIG. 28, pump body 60 generally has:

- a substantially fully expanded configuration prior to pumping;
- a collapsing and expanding configuration during pumping;
- a "vertically-oriented" substantially collapsed configuration after a given level of negative pressure has been achieved by pumping;
- a "horizontally-oriented" substantially collapsed configuration after a given level of negative pressure has been achieved but there is a decay of the negative pressure, albeit not enough of a decay to cause a binary state transition of the pump body to a substantially fully expanded configuration; and
- a substantially fully expanded configuration after the negative pressure has decayed below a given level.

Furthermore, the desired negative pressure can be re-established after transition to the substantially fully expanded configuration by renewed pumping.

NPWT Bandage with Canister for Collecting Exudates

In some situations a wound may produce significant levels of exudates. In these situations, it may be desirable for the negative pressure wound therapy (NPWT) bandage to include a canister for collecting the exudates.

Figure 29:
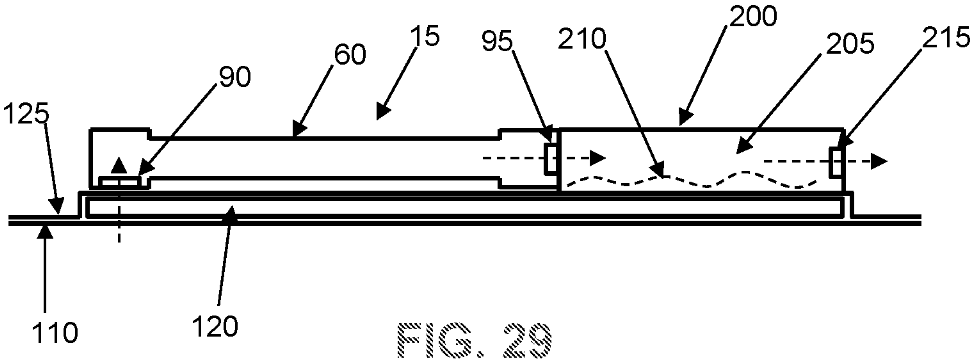
FIG. 29 is a schematic view showing another new and improved NPWT bandage formed in accordance with the present invention.

Thus, for example, and looking now at FIG. 29, there is shown a negative pressure wound therapy (NPWT) bandage 5 which includes a canister 200 for collecting exudates. In this form of the invention, atmosphere-side one-way valve 95 of pump assembly 15 outputs to the interior 205 of canister 200 so that exudates 210 collect in canister 200. In one form of the invention, canister 200 includes an opening which is covered by a membrane 215, wherein membrane 215 is gas permeable, but not fluid permeable, such that gases may escape from canister 200 but liquids will be trapped within canister 200.

Figure 30:
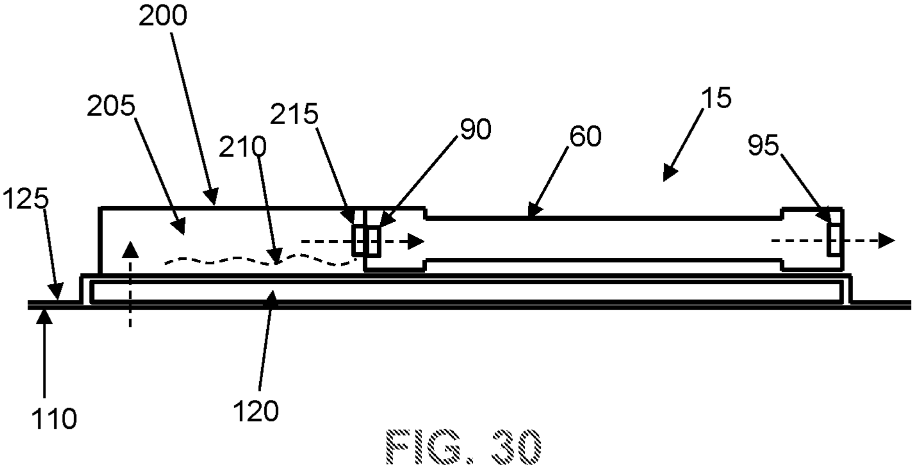
FIG. 30 is a schematic view showing another new and improved NPWT bandage formed in accordance with the present invention.

In another form of the invention, and looking now at FIG. 30, canister 200 may be disposed between the wound chamber and wound-side one-way valve 90 of pump assembly 15. More particularly, in this form of the invention, interior 205 of canister 200 is in fluid communication with the wound chamber and is in fluid communication with wound-side one-way valve 90 of pump assembly 15, such that pumping pump assembly 15 will create a negative pressure within canister 200 and hence within the wound chamber. Preferably canister 200 includes the aforementioned membrane 215 (which is gas permeable but not liquid permeable) adjacent to wound-side one-way valve 90 of pump assembly 15, such that gases may escape from canister 200, but liquids will be trapped within canister 200 and not pass into pump assembly 15.

Figure 31:
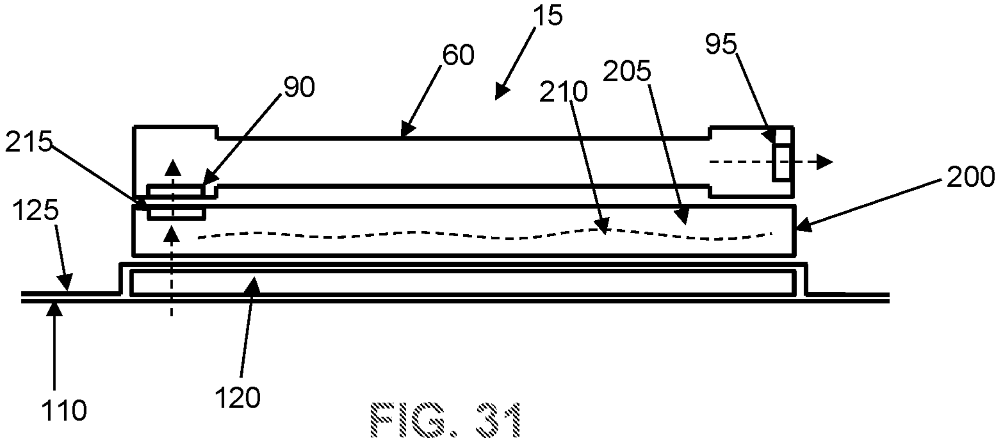
FIG. 31 is a schematic view showing another new and improved NPWT bandage formed in accordance with the present invention.

In still another form of the invention, and looking now at FIG. 31, canister 200 is disposed between the wound chamber and wound-side one-way valve 90 of pump assembly 15, in a manner similar to the construction of FIG. 30, except that pump assembly 15 is mounted atop canister 200.

It should be appreciated that canister 200 may be formed integral with pump body 60, or it may be formed separately from pump body 60 and simply be fluidly connected to pump body 60, but in any case canister 200 is preferably mounted to some portion of negative pressure wound therapy (NPWT) bandage 5 so that canister 200 moves in conjunction with the remainder of the bandage.

Furthermore, if desired, canister 200 may contain (or have one or more of its internal surfaces coated with) an absorbent or superabsorbent material to absorb liquid exudates evacuated from the wound chamber. By way of example but not limitation, canister 200 may contain (or have one or more of its internal surfaces coated with) absorbent or superabsorbent crystals or hydrocolloids or gel-forming matter.

Canister 200 may be used with any of the pump assemblies disclosed herein. By way of example but not limitation, canister 200 may be used with pump assembly 15 shown in FIGS. 1-4, pump assembly 15 shown in FIGS. 17-20A, pump assembly 15 shown in FIGS. 21-25, pump assembly 15 shown in FIGS. 26-28, etc.

NPWT Bandage with Luer Lock for Suction Attachment

In some situations it may be desirable to make negative pressure wound therapy (NPWT) bandage 5 in a large size, so that it can cover a large wound chamber. This can be accomplished by increasing the size of membrane (or sheet) 10. However, it may not be desirable to increase the size of pump assembly 15, since it is typically desirable for the pump assembly to maintain a low, non-intrusive profile. But increasing the size of membrane (or sheet) 10 while maintaining the size of pump assembly 15 can be clinically undesirable, since then many more pump compressions may be required in order to evacuate the large wound chamber to the correct negative pressure level. Stated another way, increasing the size of membrane (or sheet) 10 while maintaining the size of pump assembly 15 has the effect of increasing the number of pump compressions required to establish the correct negative pressure level in the wound chamber. Thus, clinical considerations for the size of the pump assembly, and clinical considerations for the number of pump compressions to be used to establish the correct negative pressure level in the wound chamber, may limit, in a practical sense, the size of membrane (or sheet) 10.

Figure 32:
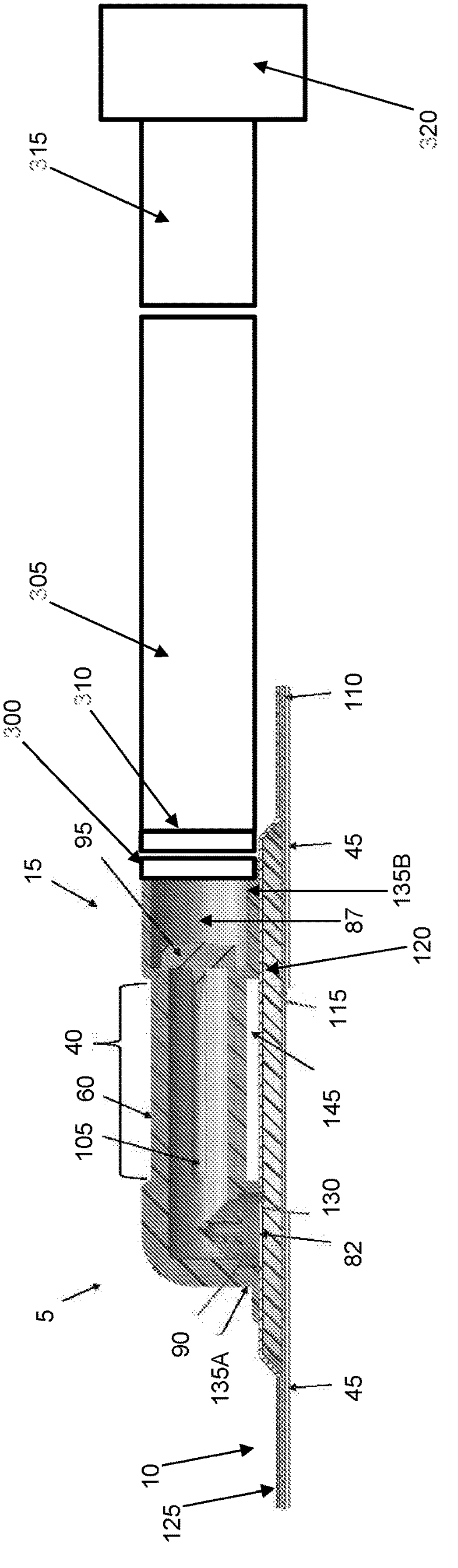
FIG. 32 is a schematic view showing another new and improved NPWT bandage formed in accordance with the present invention.

In order to address this, negative pressure wound therapy (NPWT) bandage 5 may be configured for connection to a source of suction, such that a suction source can be applied to NPWT bandage 5 so as to establish the correct negative pressure level in the wound chamber without requiring compression of pump body 60. By way of example but not limitation, and looking now at FIG. 32, NPWT bandage 5 may comprise one half 300 of a luer lock, and a suction line 305 may comprise the second half 310 of a luer lock, such that suction line 305 can be fluidly connected to atmosphere-side port 87 of pump body 60. When suction line 305 has its other end 315 connected to a functioning source of suction 320, suction source 320 can apply suction to pump body 60. This suction is then automatically applied to the wound chamber, such that suction source 320 can establish negative pressure in the wound chamber.

Significantly, when the correct level of negative pressure is established in the wound chamber, the walls of pump body 60 will collapse in the manner previously described. Thus, even where suction source 320 is used to create negative pressure in the wound chamber, NPWT bandage 5 still acts as a visual indicator of when the proper level of negative pressure has been established in the wound chamber, since pump assembly 15 transitions from its substantially fully expanded configuration to its substantially fully collapsed configuration when the proper level of negative pressure has been established in the wound chamber.

After the proper level of negative pressure has been established in the wound chamber using suction source 320, suction line 305 can then be disconnected from NPWT bandage 5.

Thereafter, if the negative pressure level in the wound chamber should decay, pump assembly 15 can be used to re-establish the correct negative pressure level in the wound chamber, either by compressing pump body 60 or by re-connecting NPWT bandage 5 to suction source 320.

In the preferred form of the invention discussed above, NPWT bandage 5 comprises one half of a luer lock, and suction line 305 comprises the second half of a luer lock. However, the present invention is not restricted to the use of a luer lock connection—other types of fluid connectors may be used to connect suction line 305 to pump assembly 15.

As discussed above, NPWT bandage 5 serves as a visual indicator of when the proper level of negative pressure has been established in the wound chamber, i.e., by transitioning from its substantially fully expanded configuration to its substantially fully collapsed configuration.

Figure 33:
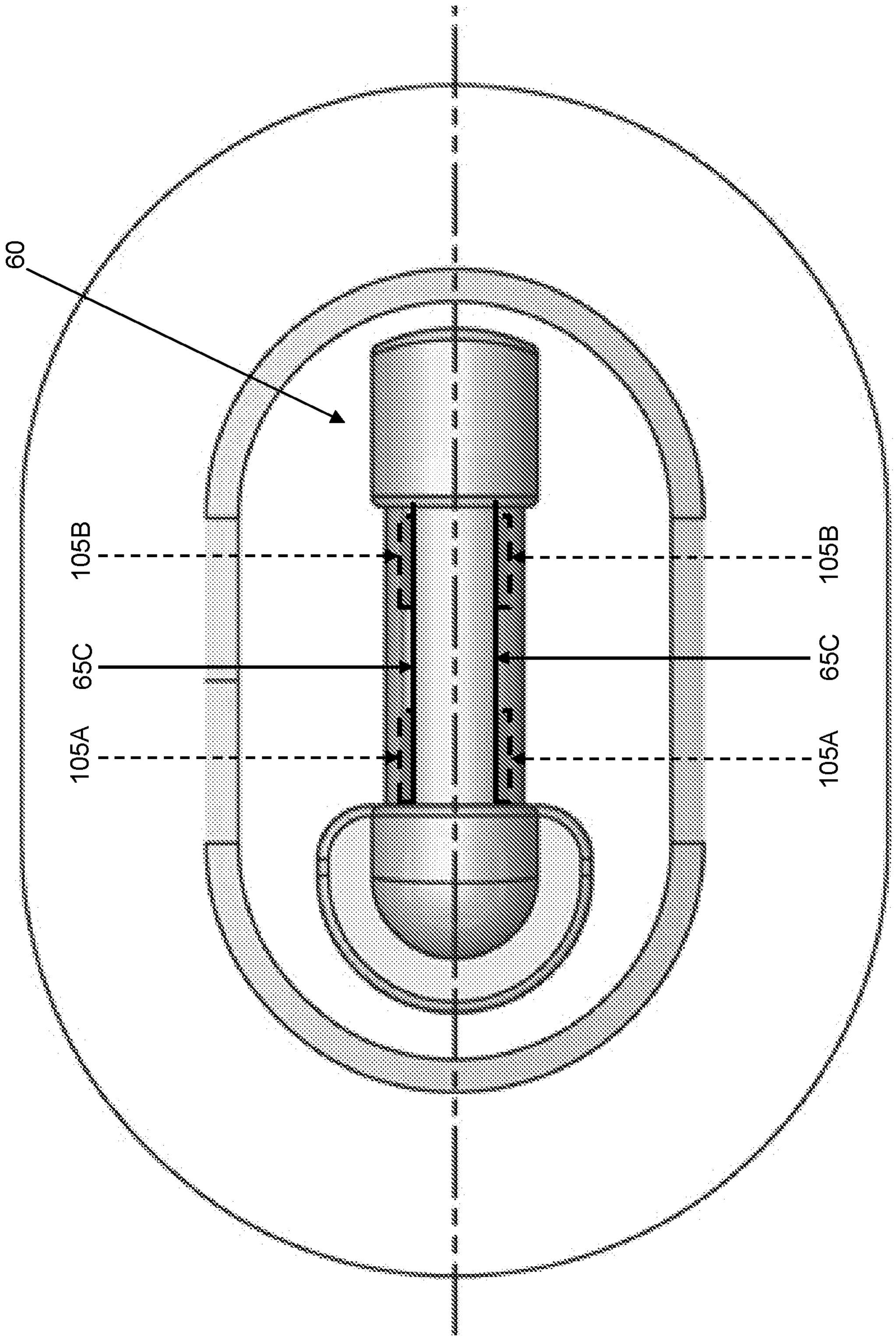
FIGS. 33 and 34 are schematic views showing another new and improved NPWT bandage formed in accordance with the present invention.
Figure 34:
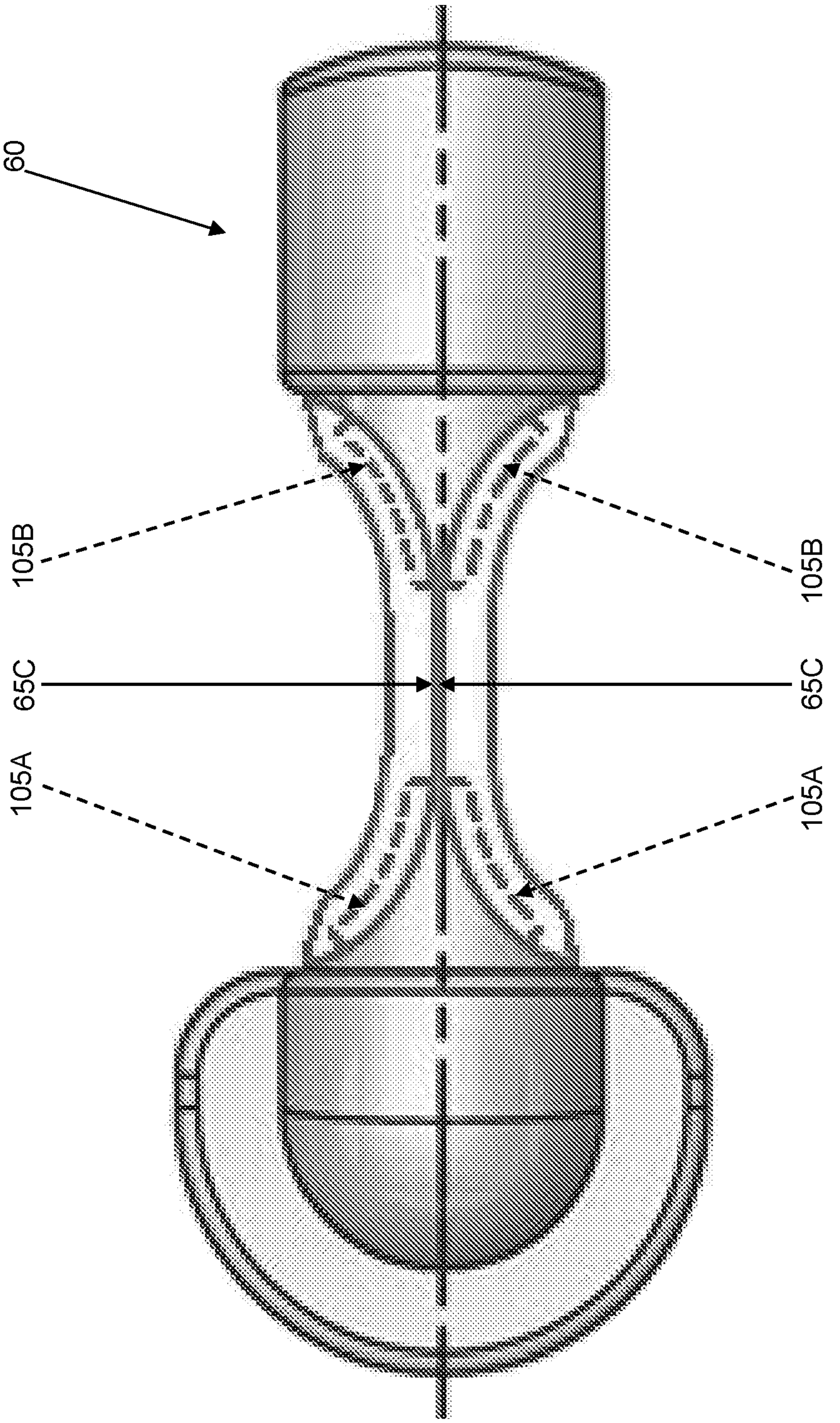

Significantly, and in accordance with another feature of the present invention, by modifying the configuration of notches 105 of pump body 60, NPWT bandage 5 can also function as a pressure limiter, so as to prevent suction source 320 from establishing too high a level of negative pressure in the wound chamber. This is done by forming each of the notches 105 as two interrupted notches 105A, 105B, with a full-thickness side wall portion 65C being disposed between the two interrupted notches 105A, 105B. See FIG. 33. As a result of this construction, when the correct level of negative pressure has been established in the wound chamber, so that pump body 60 transitions from its substantially fully expanded configuration to its substantially fully collapsed configuration, diametrically-opposing full-thickness side wall portions 65C of pump body 60 move radially inwardly and engage one another, thereby sealing inner chamber 70 of pump body 60. See FIG. 34. This prevents suction source 320 from applying any further suction to the wound chamber. In this way, NPWT bandage 5 can also function as a pressure limiter, so as to prevent suction source 320 from establishing too high a level of negative pressure in the wound chamber.

Luer lock 300 may be used with any of the pump assemblies disclosed herein. By way of example but not limitation, luer lock 300 may be used with pump assembly 15 shown in FIGS. 1-4, pump assembly 15 shown in FIGS. 17-20A, pump assembly 15 shown in FIGS. 21-25, pump assembly 15 shown in FIGS. 26-28, pump assembly 15 shown in FIGS. 29-31, etc.

NPWT Bandage Wherein the Wound Chamber Comprises a Lateral Extension, and Wherein the Pump Assembly is in Fluid Communication with the Lateral Extension, so that the Pump Assembly is Laterally Offset from the Wound while Remaining in Fluid Communication with the Wound In some situations, it may be desirable to have the pump assembly laterally offset from the wound while remaining in fluid communication with the wound. More particularly, difficult anatomical regions with more complex geometries present challenges for a negative pressure wound therapy (NPWT) bandage having a pump assembly disposed directly over the wound which is being treated. By providing a NPWT bandage wherein the wound chamber comprises a lateral extension, and wherein the pump assembly is in fluid communication with the lateral extension, the pump assembly may be laterally offset from the wound while remaining in fluid communication with the wound.

By way of example but not limitation, with such a construction, where the NPWT bandage is to be used to treat a wound in the groin area, the NPWT bandage may be positioned on the patient's anatomy so that the primary portion of the wound chamber overlies the wound and the lateral extension of the wound chamber extends along the curve of the thigh so that the pump assembly may be positioned at the top of the upper leg, which is a more stable, and topographically less complicated, anatomical region for supporting the pump assembly.

By way of further example but not limitation, where the NPWT bandage is being used to treat a wound on the patient's back, the NPWT bandage may be positioned on the patient's anatomy so that the primary portion of the wound chamber overlies the wound on the patient's back and the lateral extension of the wound chamber extends along the curve of the patient's torso so that the pump assembly may be positioned on the front of the patient, where it may be easily accessed by the patient.

The NPWT bandage may be provided with a variety of different wound chamber configurations and pump dispositions, as appropriate for different applications.

Looking now at FIGS. 35-38, there is shown a negative pressure wound therapy (NPWT) bandage 5, wherein the wound chamber comprises a lateral extension, and wherein the pump assembly is in fluid communication with the lateral extension, such that the pump assembly may be laterally offset from the wound while remaining in fluid communication with the wound.

More particularly, the NPWT bandage 5 shown in FIGS. 35-38 comprises a membrane 10 and a pump assembly 15. Membrane 10 comprises a first portion 405 for disposition over a wound and a second portion 410 for extending laterally away from the wound and for supporting pump assembly 15 at an anatomical position that is spaced from the wound.

With this form of the invention, membrane 10 is generally similar to membrane 10 of the constructions shown in FIGS. 21-34 in that membrane 10 comprises a lower skin-contacting polyurethane layer 110, an intermediate foam layer 120 for disposition over lower skin-contacting polyurethane layer 110, and an upper polyurethane layer 125 for disposition over intermediate foam layer 120 and lower skin-contacting polyurethane layer 110. In the preferred form of the invention, upper polyurethane layer 125 is formed out of a substantially air-impermeable material. The outer perimeters of upper polyurethane layer 125 and lower skin-contacting polyurethane layer 110 are secured to one another, capturing intermediate foam layer 120 therebetween.

However, in this construction (i.e., the construction shown in FIGS. 35-38), center opening 115 is formed in first portion 405 of lower skin-contacting polyurethane layer 110 of membrane 10, and opening 130 is formed in second portion 410 of upper polyurethane layer 125 of membrane 10. Intermediate foam layer 120 is fluid communication with center opening 115 of first portion 405 and with opening 130 of second portion 410. In this way, when NPWT bandage 5 is adhered to anatomy with its center opening 115 positioned over a wound, membrane 10 forms a wound chamber which is generally defined by the configuration of the intermediate foam layer 120. This wound chamber generally comprises (i) a primary portion which overlies center opening 115 of first portion 405, and (ii) a lateral extension which extends from the primary portion of the wound chamber to pump assembly 15.

Pump assembly 15 is mounted to upper polyurethane layer 125 so that wound-side passageway 80 of pump assembly 15 can access fluid (e.g., air, liquid, etc.) within the lateral extension of the wound chamber, and hence access fluid within the primary portion of the wound chamber (i.e., via the porous cells of intermediate foam layer 120), whereby to draw fluid away from the wound site.

In an exemplary use of the NPWT bandage 5 of FIGS. 35-38, the NPWT bandage is positioned on the patient's anatomy so that the primary portion of the wound chamber overlies the wound, and the lateral extension of the wound chamber extends along the patient's anatomy so that the pump assembly may be laterally offset from the wound, e.g., positioned at another location which is a more stable, and/or topographically less complicated, and/or more easily accessible for the patient. NPWT bandage 5 may then be used to apply negative pressure to the wound chamber so that fluid (e.g., air, liquid, etc.) can pass from the wound, through center opening 115 into the primary portion of the wound chamber, through the lateral extension of the wound chamber (e.g., through the porous cells of intermediate foam layer 120) and into pump assembly 15 via opening 130 in second portion 410 of upper polyurethane layer 125 of membrane 10.

The NPWT bandage 5 of FIGS. 35-38 may also be used at other complicated, or mobile, wound locations, including but not limited to, the foot (diabetic foot ulcers, etc.), a joint such as the ankle, knee, shoulder, or hip (after joint surgeries, ligament repair, arthroscopic procedures, joint replacements, etc.), the arm (lower or upper), the neck, the head, the spine or back (pump assembly 15 can be placed on the front of the body while the primary portion of the wound chamber is positioned over the wound), etc. In each of these wound locations, and others, the anatomical location of the wound can provide a challenge for a wound dressing having an integrated pinch pump assembly, because of the configuration of the anatomy, or the mobility of the anatomical location, or the radius of curvature at the anatomical location, or the location of the wound (which may not be easy for the patient to directly visualize or manually reach), etc. Significantly, an NPWT bandage formed in accordance with the present invention, wherein the wound chamber comprises a lateral extension, and wherein the pump assembly is in fluid communication with the lateral extension, so that the pump assembly is laterally offset from the wound while remaining in fluid communication with the wound, provides the ability to locate the pinch pump assembly at an easily accessible, and physically stable, anatomical location while still preserving air/fluid communication with the wound.

This novel NPWT bandage may comprise any number of geometries, including but not limited to:

1—a wound chamber having a lateral extension of various lengths (e.g., short, long, etc.), wherein the lateral extension is in line with the center of the dressing, with the pinch pump assembly being oriented at any angle to the centerline of the dressing; and 2—a wound chamber having a lateral extension of various lengths (e.g., short, long, etc.), wherein the lateral extension is located off the centerline of the dressing.

By way of example but not limitation, FIGS. 39-42 show an alternative construction for a negative pressure wound therapy (NPWT) bandage 5, wherein the lateral extension of the wound chamber has a different length than that shown in FIGS. 35-38.

By way of further example but not limitation, FIGS. 43-46 show an alternative construction for a negative pressure wound therapy (NPWT) bandage 5, wherein the pinch pump assembly extends transverse to the axis of the lateral extension of the wound chamber.

Figure 46:
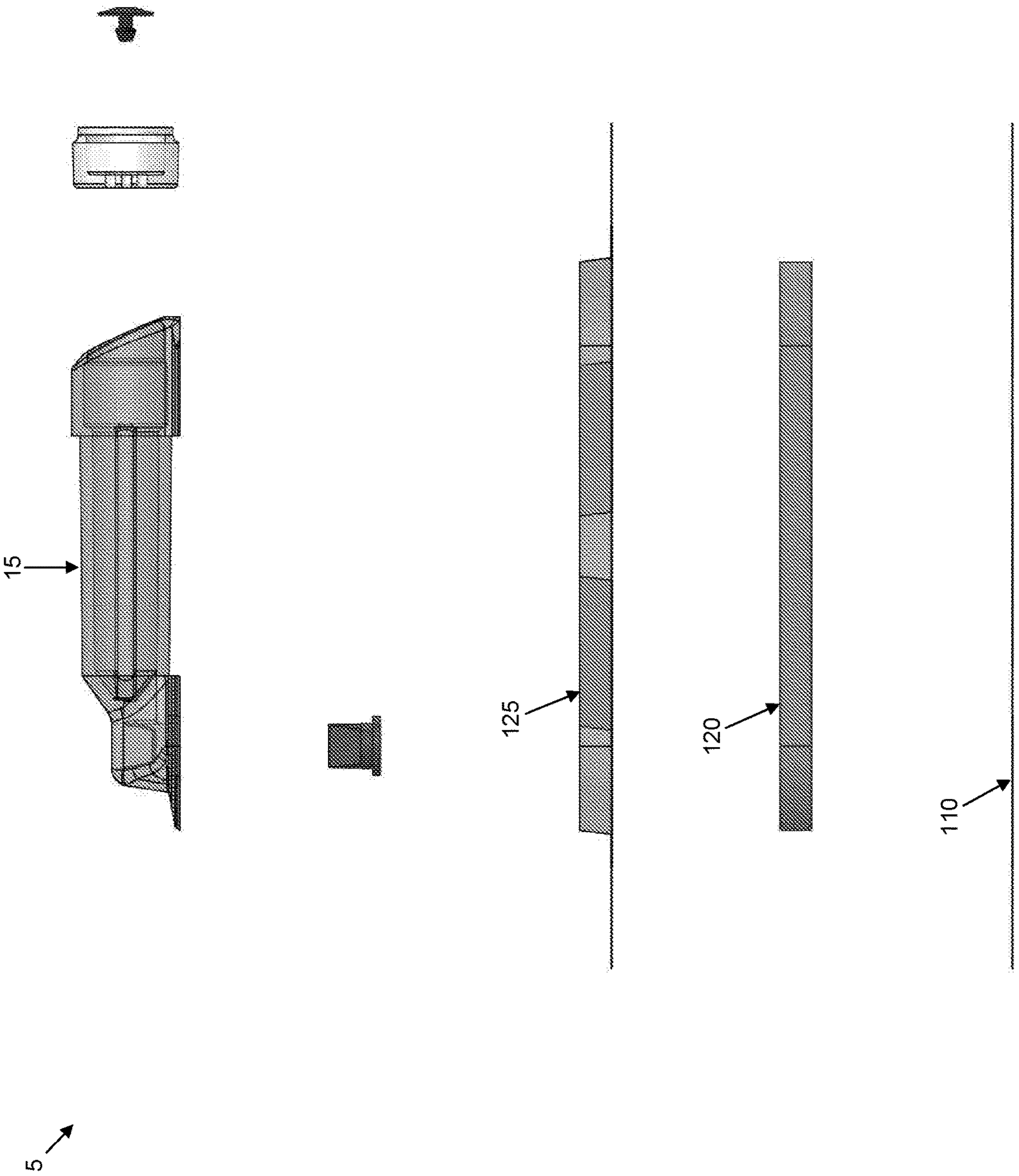
Figure 46A:
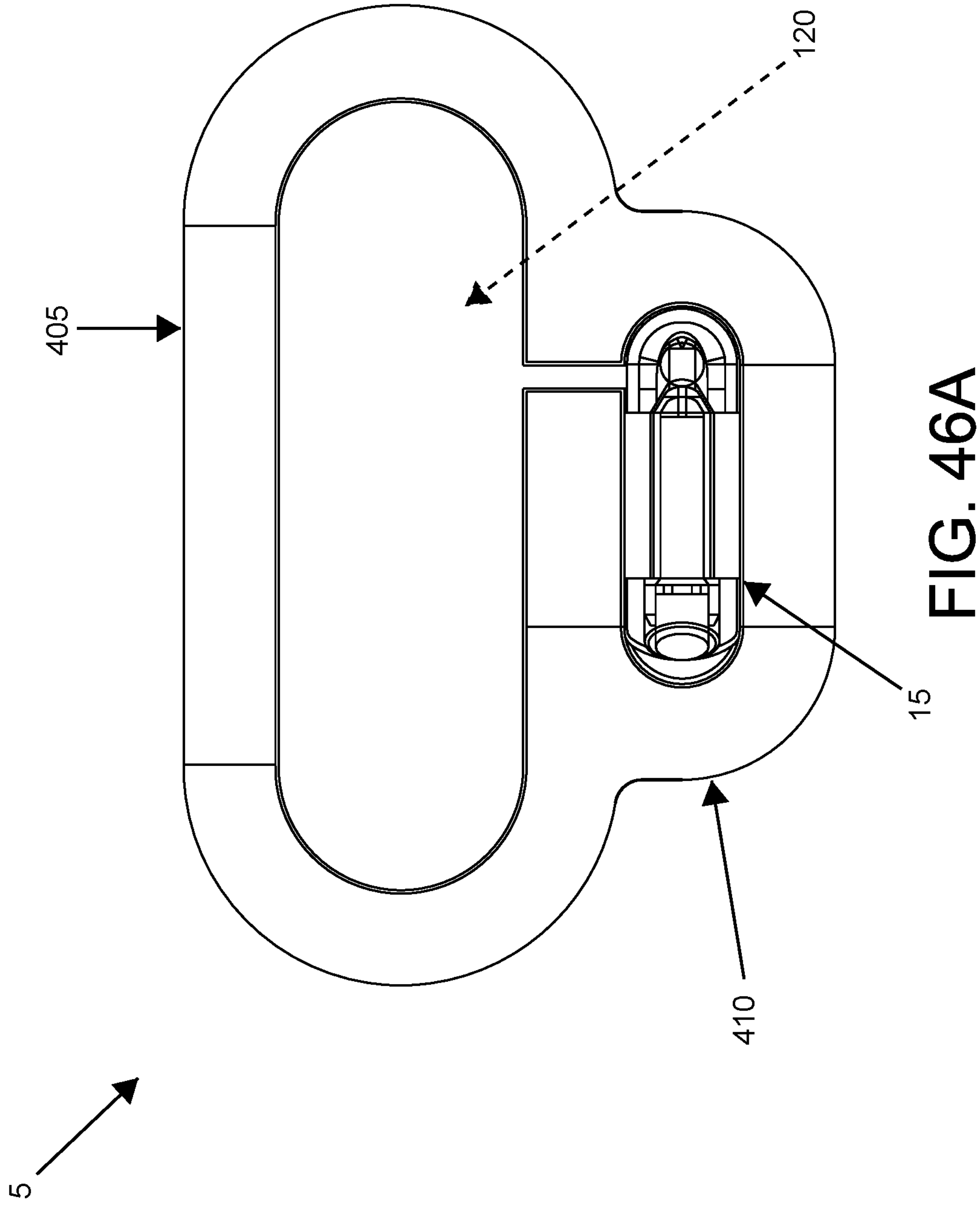
FIG. 46A is a schematic view showing another new and improved NPWT bandage formed in accordance with the present invention, wherein the wound chamber comprises a lateral extension, and wherein the pump assembly is in fluid communication with the lateral extension, so that the pump assembly is laterally offset from the wound while remaining in fluid communication with the wound.

By way of still further example but not limitation, and looking now at FIG. 46A, the second portion 410 of the wound chamber may extend parallel to, but be offset from, first portion 405 of the wound chamber (as opposed to being disposed adjacent to one end of first portion 405 of the wound chamber, such as is shown in the constructions of FIGS. 35-38, 39-42 and 43-46). Pump assembly 15 is mounted to second portion 410 so as to be in fluid communication with the wound chamber (in the same manner described for the constructions of FIGS. 35-38, 39-42 and 43-46), however, in the construction shown in FIG. 46A, pump assembly extends substantially parallel to first portion 405 of the wound chamber. Note that with the construction of FIG. 46A, the footprint of negative pressure wound therapy (NPWT) bandage 5 may be more of a “square” (in the sense that the length and width of the bandage are more equal) than an “elongated rectangle” (in the sense that the length of the bandage is substantially greater than the width of the bandage) such as is shown in the constructions of FIGS. 35-38, 39-42 and 43-46.

If desired, notches 105 formed in pump body 60 of the pump assembly shown in FIGS. 17-20 and/or notches 105 formed in pump body 60 of the pump assembly shown in FIGS. 26-28 may also be formed into the respective pump bodies of the NPWT bandages 5 shown in FIGS. 35-38, FIGS. 39-42 and FIGS. 43-46. Furthermore, if desired, canister 200 may be used with the pump assemblies of the NPWT bandages 5 shown in FIGS. 35-38, FIGS. 39-42 and FIGS. 43-46. And, if desired, luer lock 300 may be used with the pump assemblies of the NPWT bandages 5 shown in FIGS. 35-38, FIGS. 39-42 and FIGS. 43-46.

Negative Pressure Wound Therapy (NPWT) Bandage for Covering a Wound, Wherein the Bandage Comprises a Transparent Top Layer which Captures a Layer of Foam Against the Wound, Wherein the Foam Layer is Provided with a Series of Windows which (i) Allow Direct Visualization of the Wound, and (ii) Provide a Metric Along the Length of the Bandage to Indicate Whether the Bandage Needs to be Replaced, and Further Wherein the Foam Layer Comprises Perimeter Serrations which Allow the Bandage to Conform to a Curved Wound The foregoing description discloses a variety of negative pressure wound therapy (NPWT) bandages which cover a wound and apply negative pressure to the wound so as to help prevent infection in the wound. The NPWT bandages disclosed in the foregoing description generally comprise (i) a membrane 10 for disposition over a wound, and (ii) an on-board pump assembly 15 for applying, and maintaining, negative pressure at the wound site.

As shown in the constructions of FIGS. 21-46, membrane 10 generally comprises (i) a lower skin-contacting polyurethane layer 110 having an opening 115 for disposition over the wound, (ii) an intermediate foam layer 120 for disposition over opening 115 in lower skin-contacting polyurethane layer 110 so as to be in contact with the wound, and (iii) an upper polyurethane layer 125 for disposition over intermediate foam layer 120 and lower skin-contacting polyurethane layer 110, wherein the outer perimeters of upper polyurethane layer 125 and lower skin-contacting polyurethane layer 110 are secured to one another, capturing intermediate foam layer 120 therebetween, and further wherein lower skin-contacting polyurethane layer 110 is provided with an adhesive for adhering membrane 10 to the skin of a patient.

Pump assembly 15 can be centered over the wound (see pump assembly shown in the embodiments of FIGS. 1-25) or can be laterally offset from the wound (see pump assembly 15 shown in the embodiments of FIGS. 35-46).

Exudate is frequently released from the wound site, particularly in view of the negative pressure being applied to the wound. In many cases it can be desirable to obtain an indication of the amount of exudate which is being produced by the wound, since high exudate production may require the bandages to be changed more frequently (e.g., because the bandages may become saturated with exudate, or because the exudate may reach the pump, which can diminish pump function and/or cause exudate to be expelled from the pump).

To this end, a new bandage for use with wounds of the type likely to release exudate is now provided. More particularly, and looking now at FIGS. 47, 48 and 49, there is shown a bandage 500 for disposition over a wound likely to release exudate. Bandage 500 is similar to the NPWT bandages disclosed in the foregoing description, except that upper polyurethane layer 125 of membrane 10 is replaced with an upper layer 505, and intermediate foam layer 120 of membrane 10 is replaced with foam layer 510.

More particularly, upper layer 505 of bandage 500 is formed out of a transparent material (e.g., a film). The transparent upper layer 505 of the bandage allows an observer to see through the upper layer of the bandage and to observe foam layer 510 (which absorbs the exudate) covering the wound.

Foam layer 510 (see FIGS. 47-55) is provided with a series of windows 515 extending through the foam layer. Windows 515 allow direct visualization of the wound and provide a metric along the length of the bandage to indicate whether the bandage needs to be replaced. Note that in FIGS. 50 and 53-55, only foam layer 510 of bandage 500 is shown for clarity of explanation.

Figure 51:
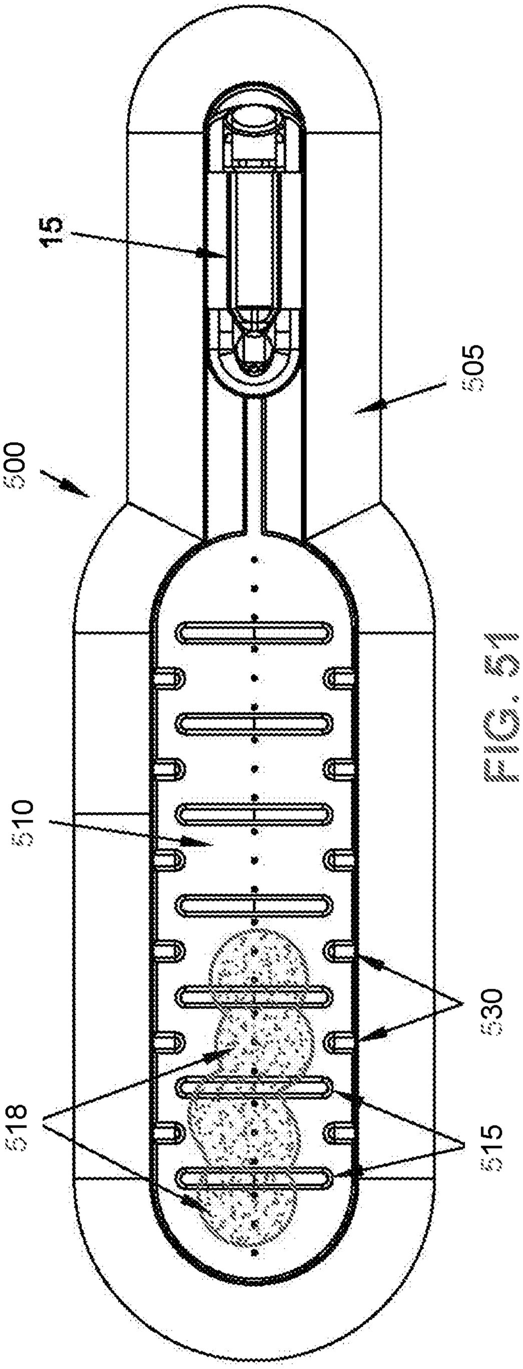
FIGS. 51 and 52 are schematic views showing various levels of exudate in the foam layer of the bandage of FIG. 47.
Figure 52:
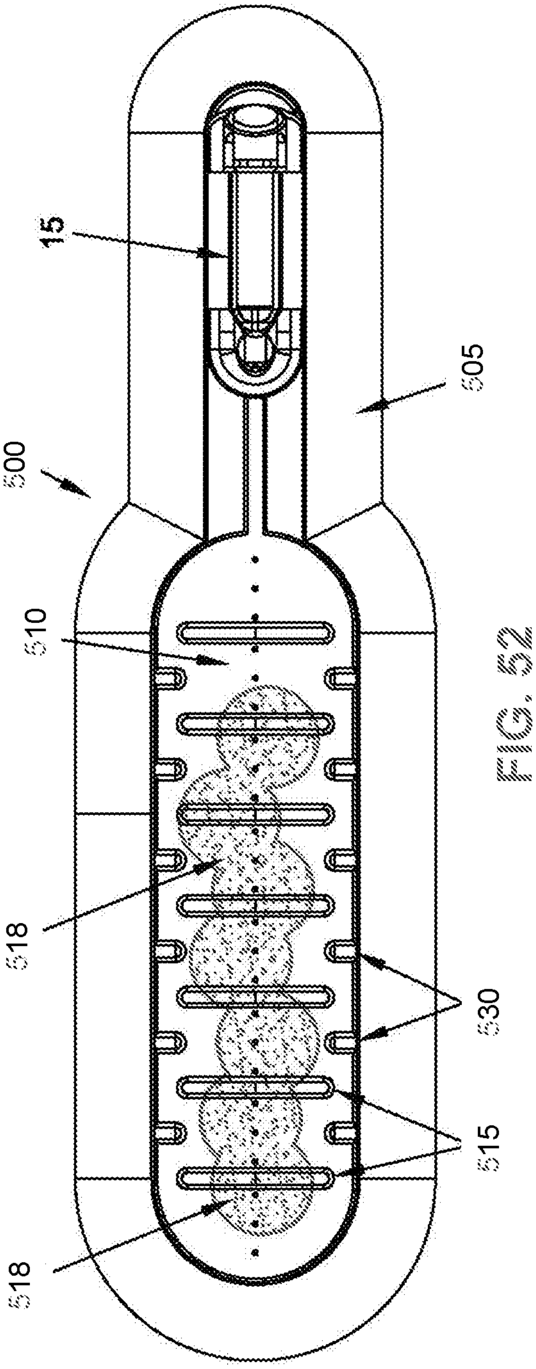

More particularly, and looking now at FIGS. 51 and 52, visualization of foam layer 510 through transparent upper layer 505 allows an observer to visualize whether a large amount of exudate has migrated into the foam layer from the wound (the exudate is typically yellowish so it is easily seen against the base color of the foam, which is preferably white, light gray, etc.), and windows 515 provide a metric which extends along the length of the bandage (e.g., each of the windows is a "marker line" along the "ruler" of the bandage). The quantity of exudate emitted by the wound is reflected by the amount of the foam which shows the presence of exudate (this can be quantified by viewing the portions of foam layer 510 which show exudate and counting the number of windows adjacent to the areas of foam layer 510 showing exudate). When the number of windows adjacent to the areas of foam layer 510 showing exudate reaches a certain number along the length of foam layer 510, the observer will have a sense of the quantity of exudate leaving the wound and can decide whether to change the bandage. By way of example but not limitation, if the amount of saturation of foam layer 510 is less than 50% (as shown in FIG. 51, which shows that the number of windows adjacent to the areas of foam layer 510 showing exudate 518 is three out of seven windows), then the bandage may remain on the wound; if, however, the amount of saturation of foam layer 510 is greater than 50% (as shown in FIG. 52, which shows that the number of windows adjacent to the areas of foam layer 510 showing exudate 518 is four or more windows), then the bandage may be changed. By way of further example but not limitation, when the area of foam layer 510 surrounding the window nearest the pump exhibits the presence of exudate, the decision may be made to change the bandage so as to keep the exudate from reaching the pump.

Figure 53:
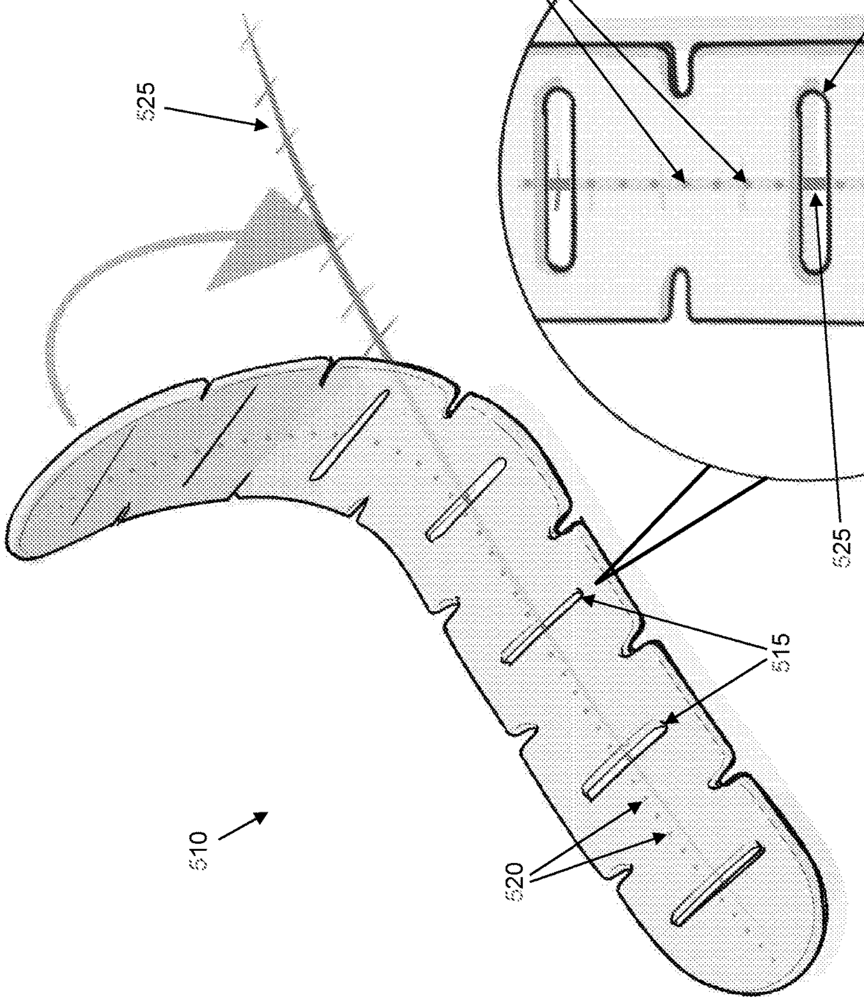
FIGS. 53 and 54 are schematic views showing how the windows in the foam layer allow medical personnel to align the bandage along a wound line.
Figure 54:
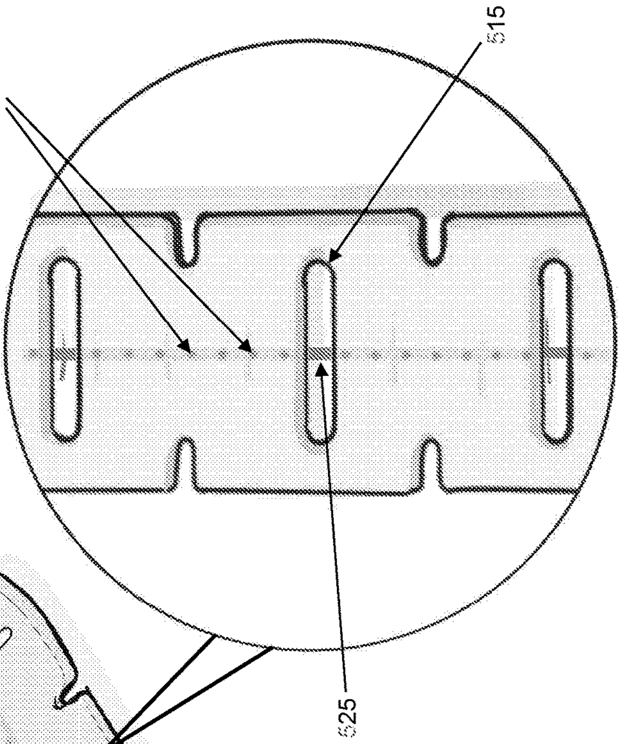

In a preferred embodiment, bandage 500 may be provided with markings 520 along the length of the bandage. Markings 520 may be formed on transparent upper layer 505 and/or foam layer 510 (see FIGS. 50-55). As seen in FIGS. 53 and 54, markings 520 may be used in combination with windows 515 in foam layer 510 to allow medical personnel to align bandage 500 along a wound line 525 when applying the bandage to the wound.

Figure 55:
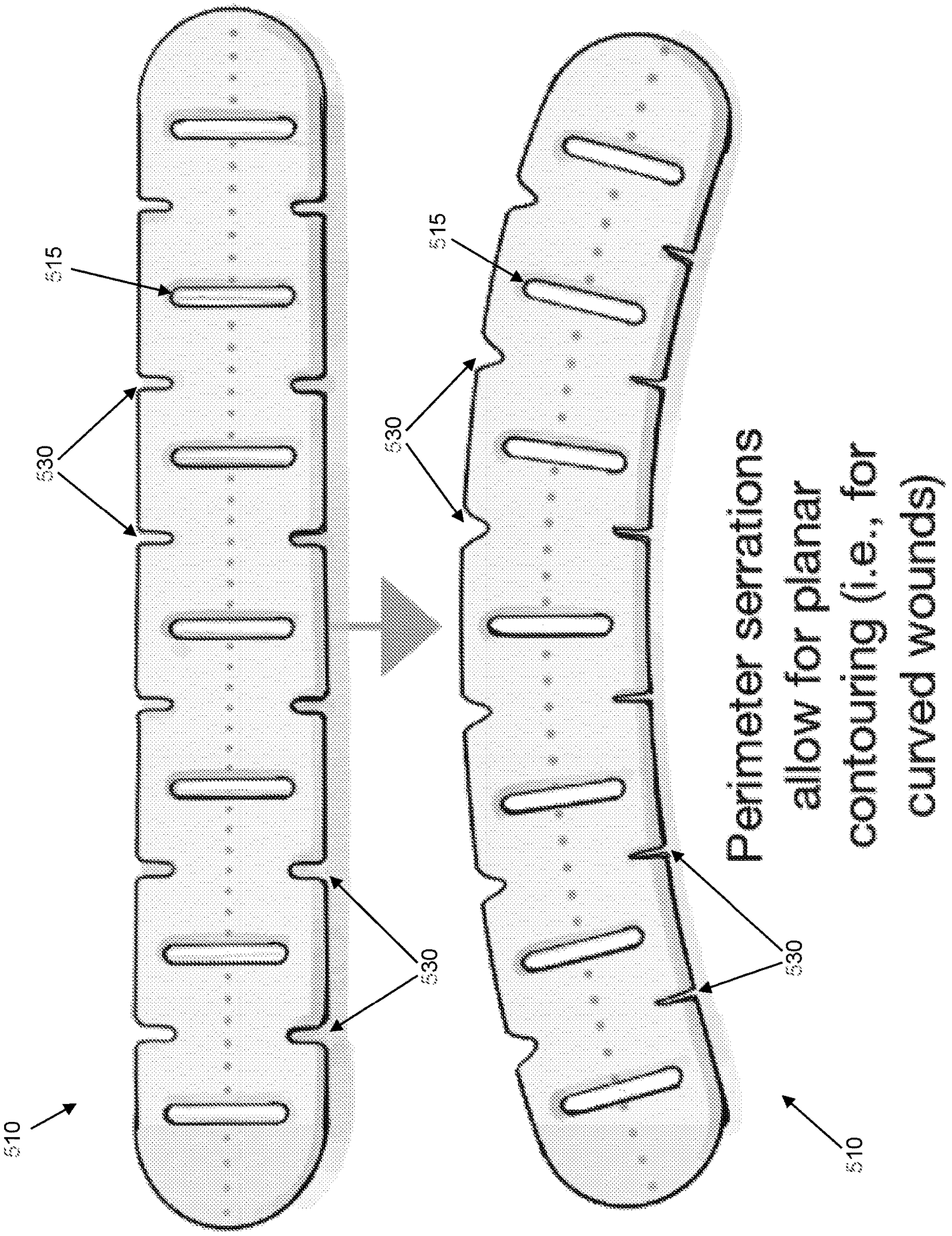
FIG. 55 is a schematic view showing perimeter serrations formed in the foam layer which allow the bandage to be curved so as to follow the path of a curved wound.

If desired, the perimeter of foam layer 510 may be formed with scalloped edges or perimeter serrations 530 (see FIGS. 47-55). As seen in FIG. 55, scalloped edges or perimeter serrations 530 enable bandage 500 to be curved somewhat when being applied to the skin surface so that bandage 500 may be positioned over a non-linear incision. To this end, it is important to note that the portion of bandage 500 that is positioned over a wound must not be curved too much, as too much curvature of the bandage may cause wrinkling of the bandage, which can cause the seal around the wound chamber to fail. The extent of curvature of the bandage that can be accommodated without disrupting the function of the bandage depends on a number of factors, including but not limited to the size and geometry (width and depth) of perimeter serrations 530 in foam layer 510, the ability of the upper layer 505 to deform, the ability of lower skin-contacting polyurethane layer 110 to deform, etc. If desired, perimeter serrations may also be formed in upper layer 505 and/or in lower skin-contacting polyurethane layer 110 so as increase the degree of curvature that the bandage can accommodate (e.g., decrease "wrinkling" of upper layer 505 and lower skin-contacting polyurethane layer 110 when the bandage is positioned over a non-linear incision, so as to increase the degree of curvature that the bandage can accommodate without compromising the air-tight seal made with the skin).

Figure 35:
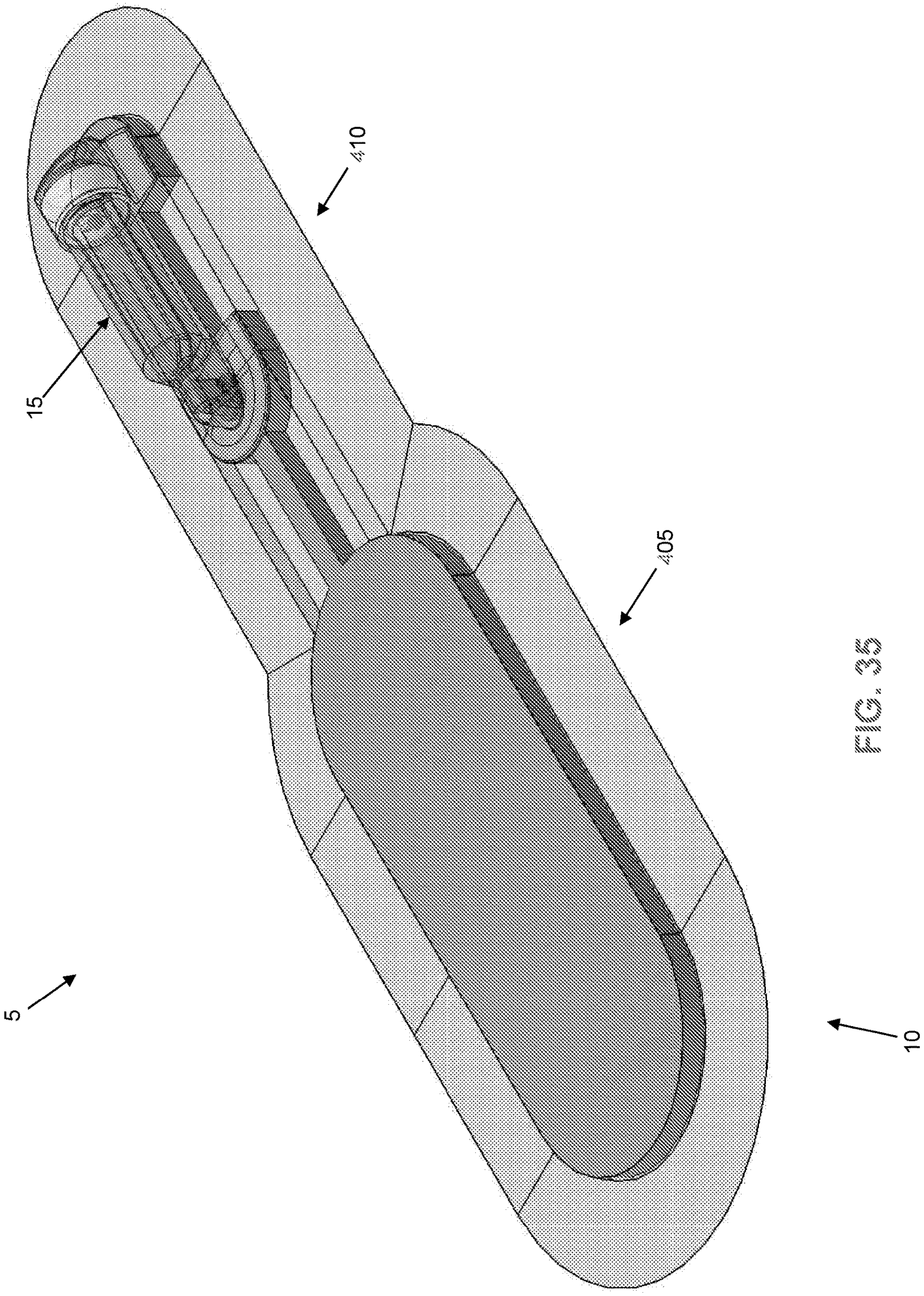
FIGS. 35-38 are schematic views showing another new and improved NPWT bandage formed in accordance with the present invention, wherein the wound chamber comprises a lateral extension, and wherein the pump assembly is in fluid communication with the lateral extension, so that the pump assembly is laterally offset from the wound while remaining in fluid communication with the wound.
Figure 36:
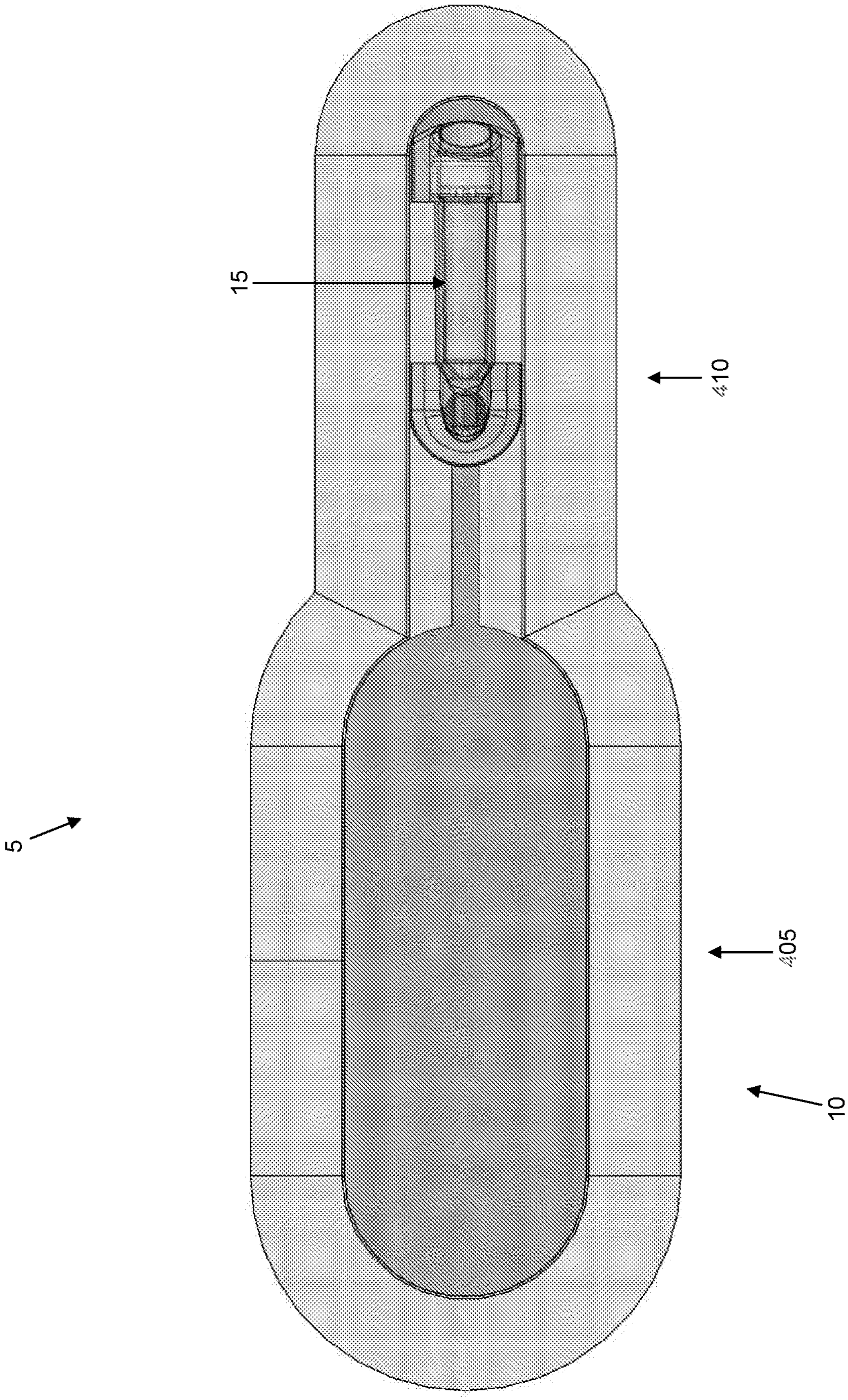
Figure 37:
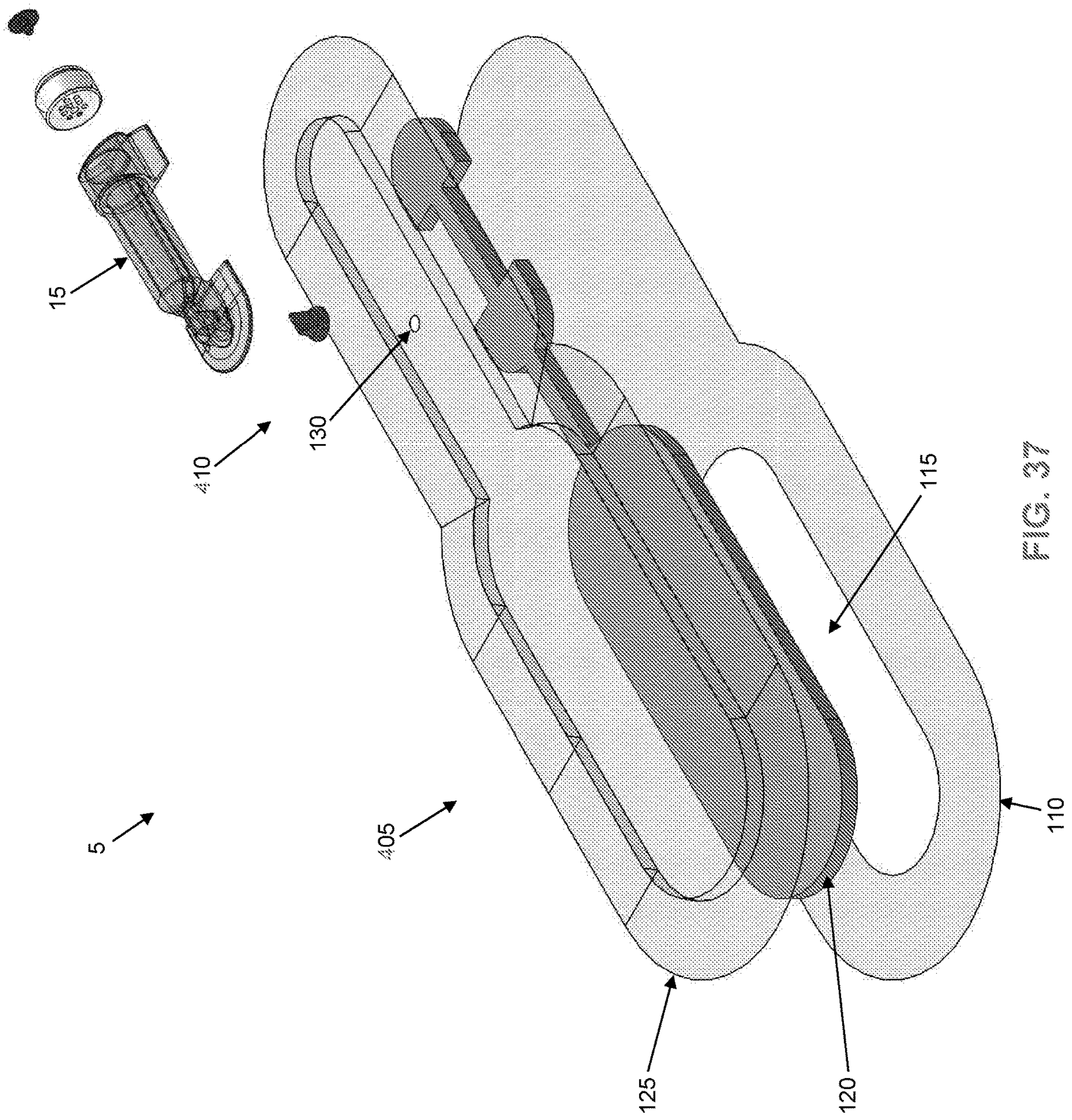
Figure 38:
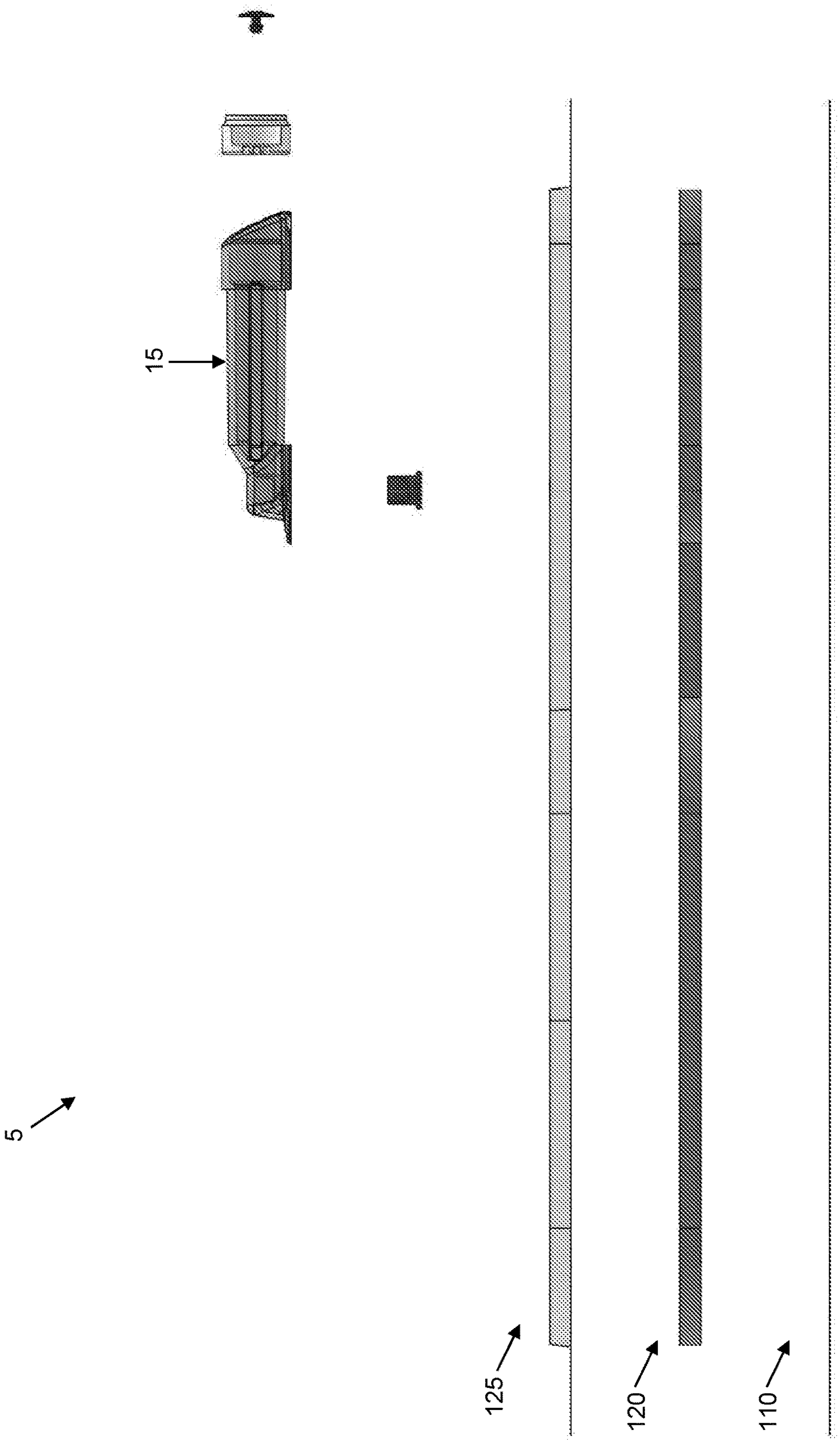
Figure 39:
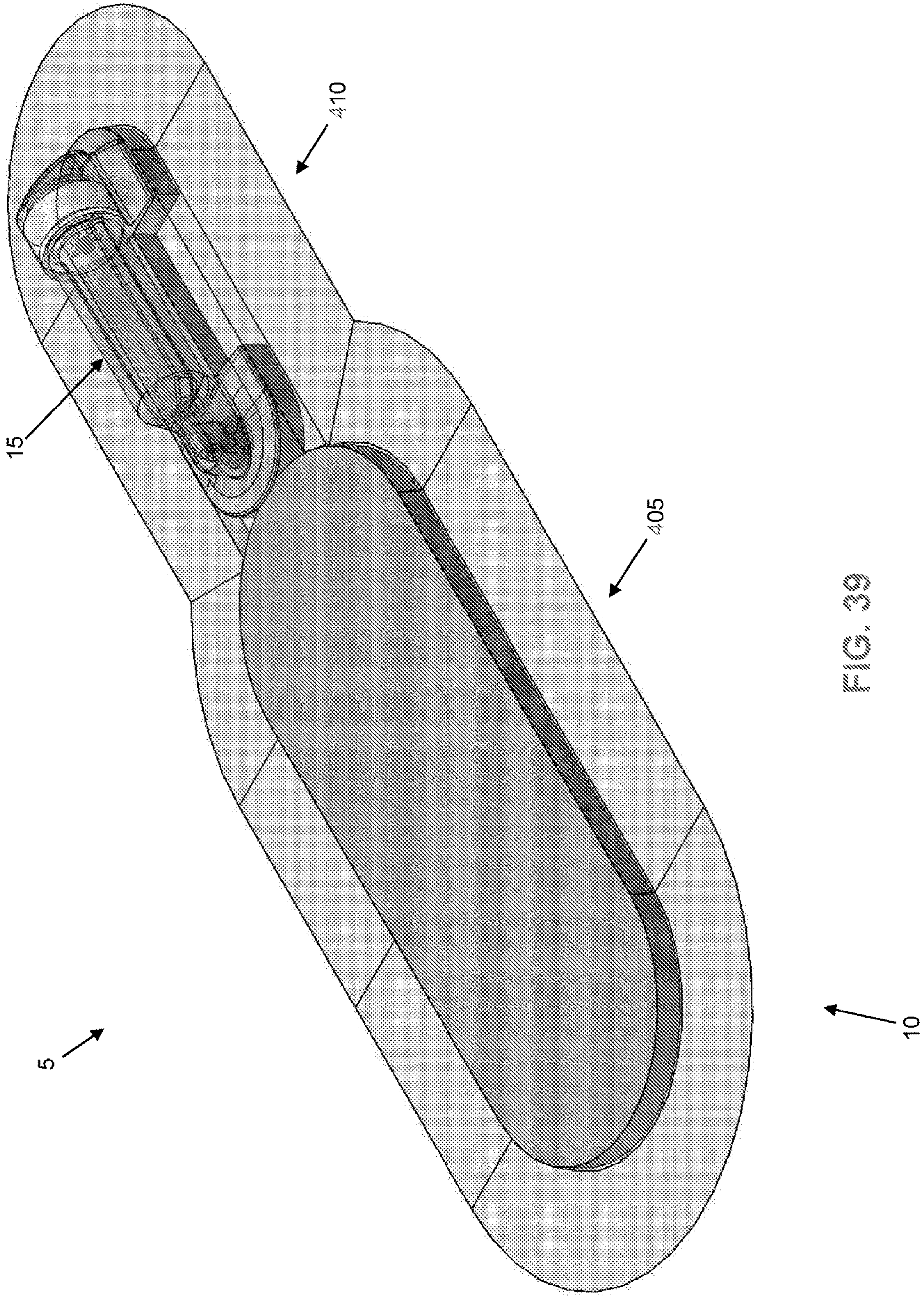
FIGS. 39-42 are schematic views showing another new and improved NPWT bandage formed in accordance with the present invention, wherein the wound chamber comprises a lateral extension, and wherein the pump assembly is in fluid communication with the lateral extension, so that the pump assembly is laterally offset from the wound while remaining in fluid communication with the wound.
Figure 40:
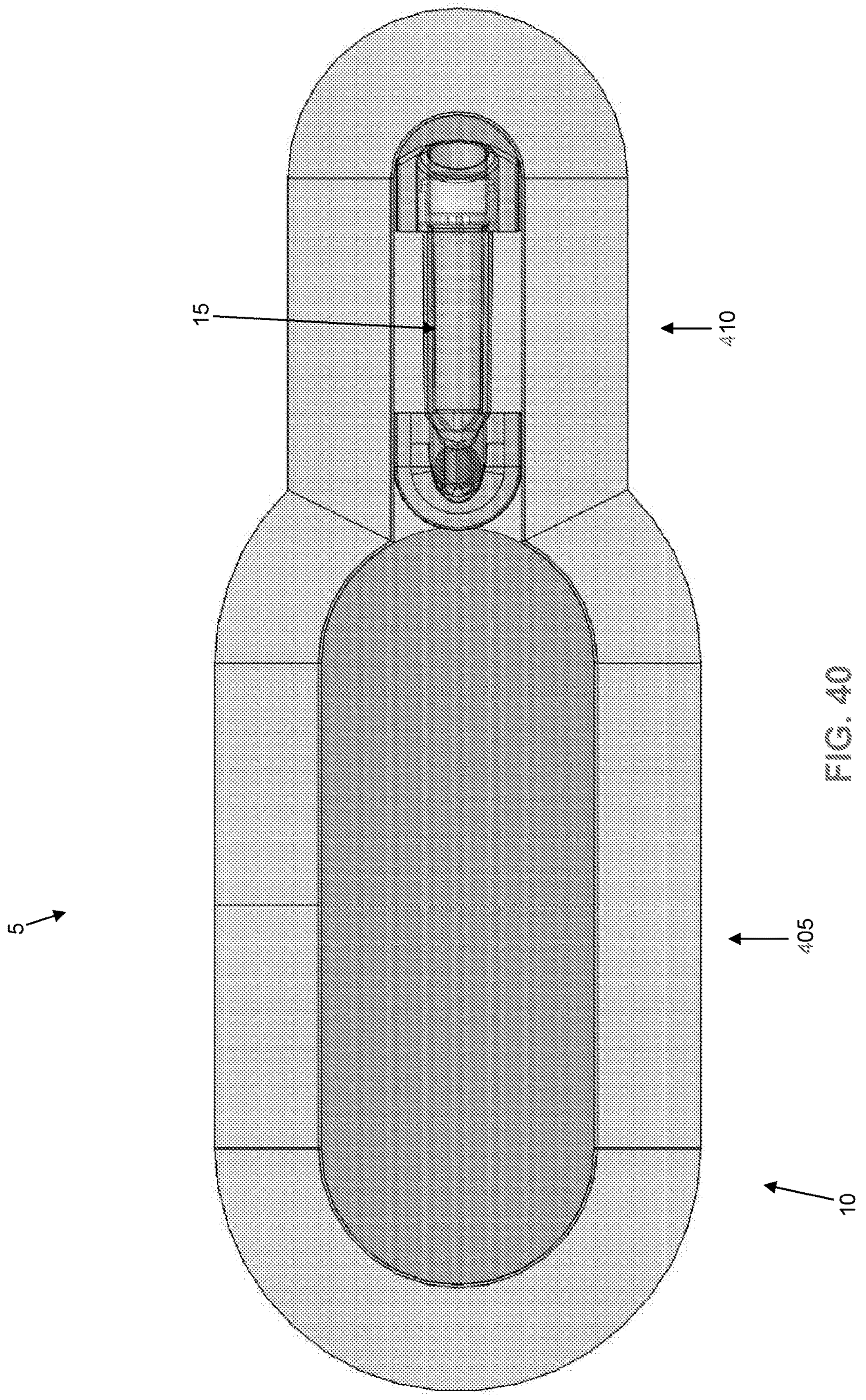
Figure 41:
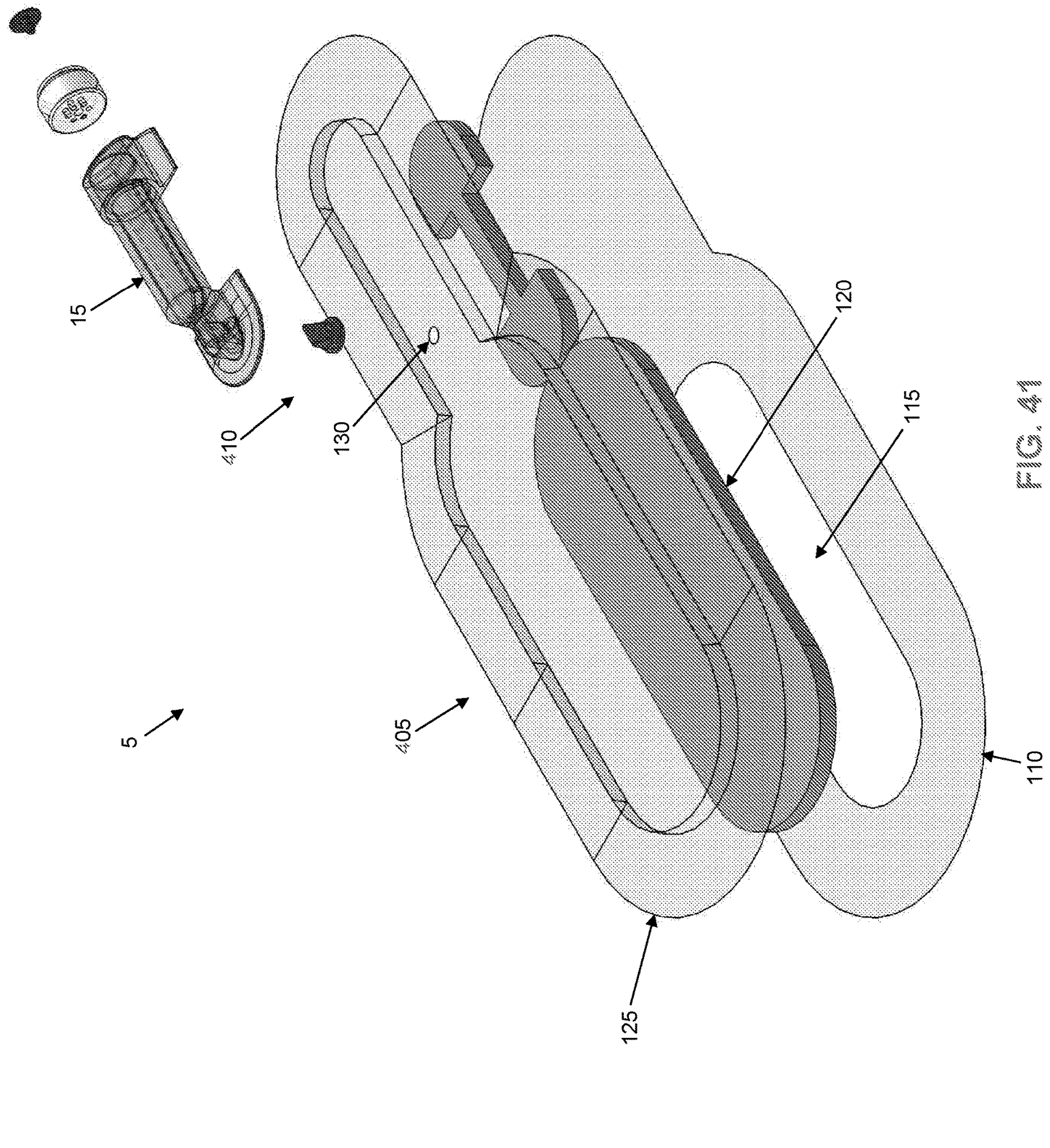
Figure 42:
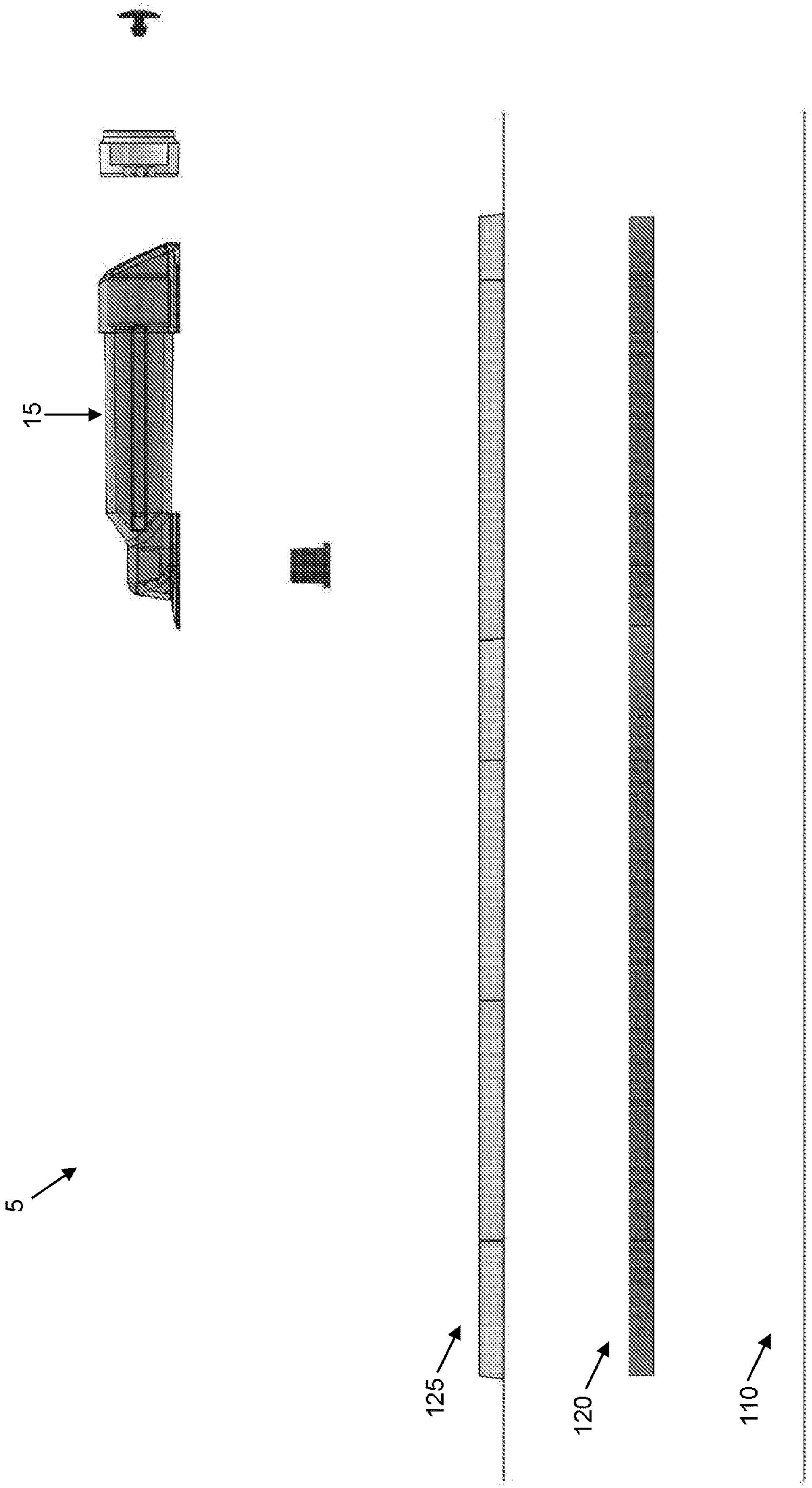
Figure 43:
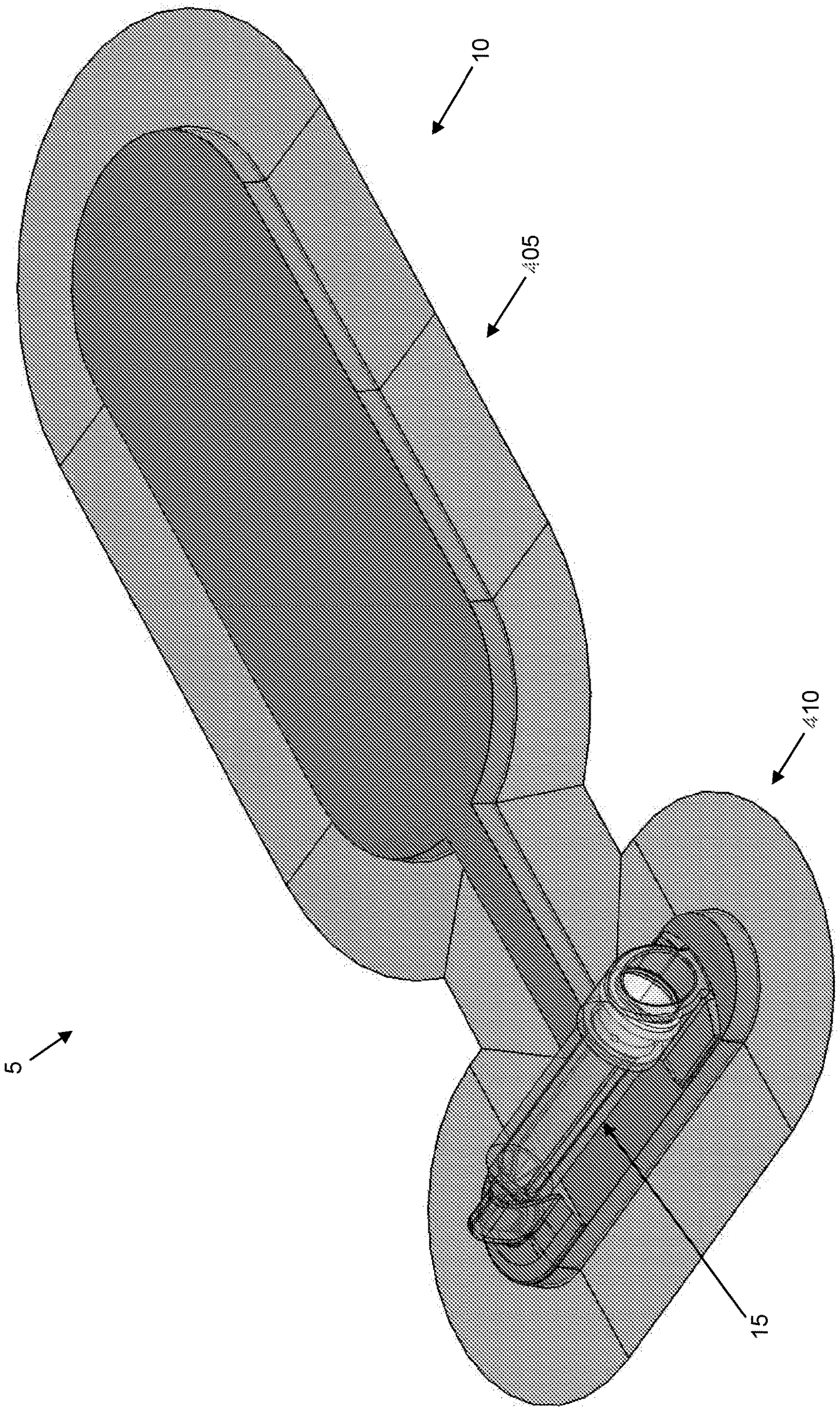
FIGS. 43-46 are schematic views showing another new and improved NPWT bandage formed in accordance with the present invention, wherein the wound chamber comprises a lateral extension, and wherein the pump assembly is in fluid communication with the lateral extension, so that the pump assembly is laterally offset from the wound while remaining in fluid communication with the wound.
Figure 44:
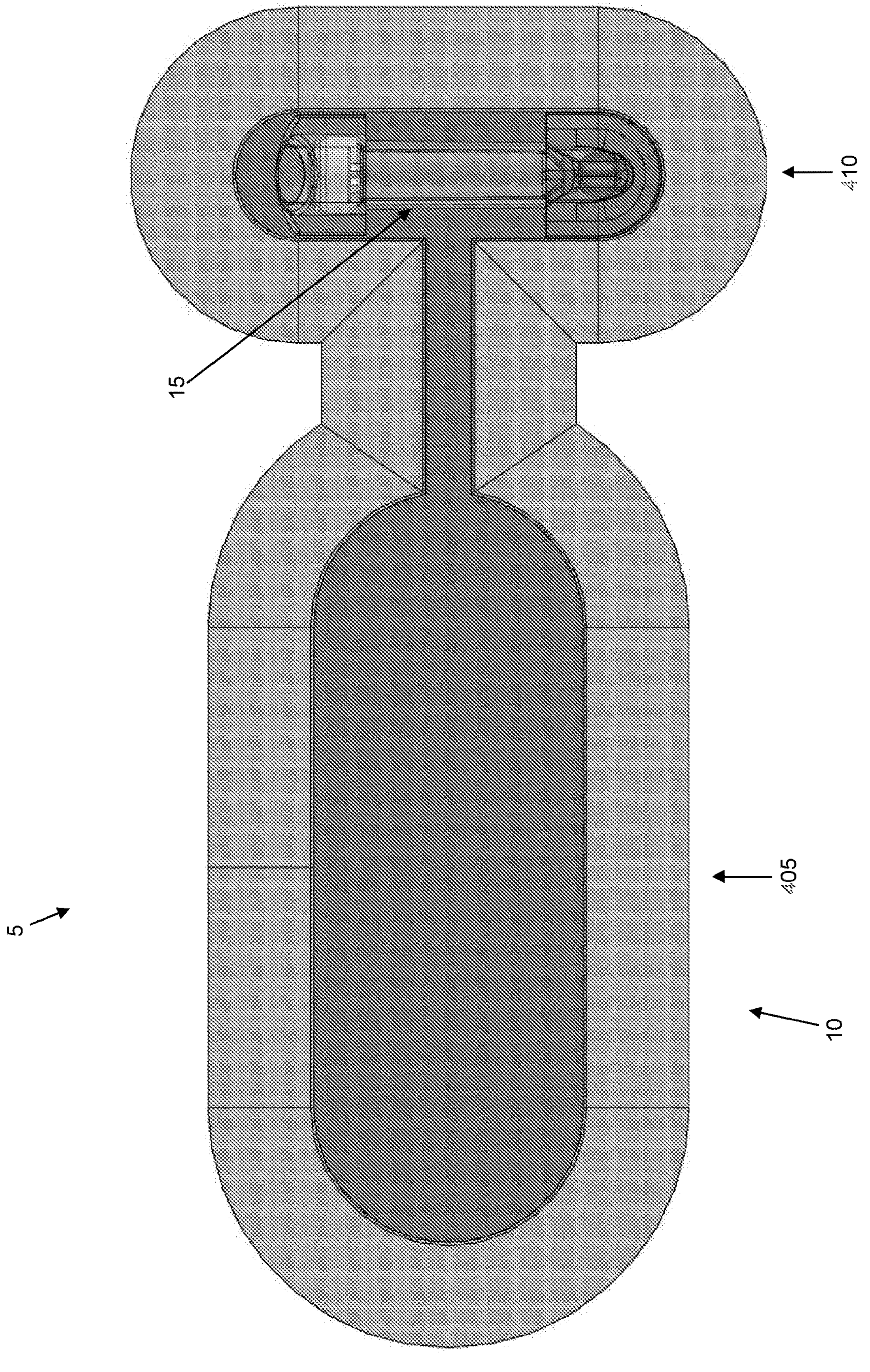
Figure 45:
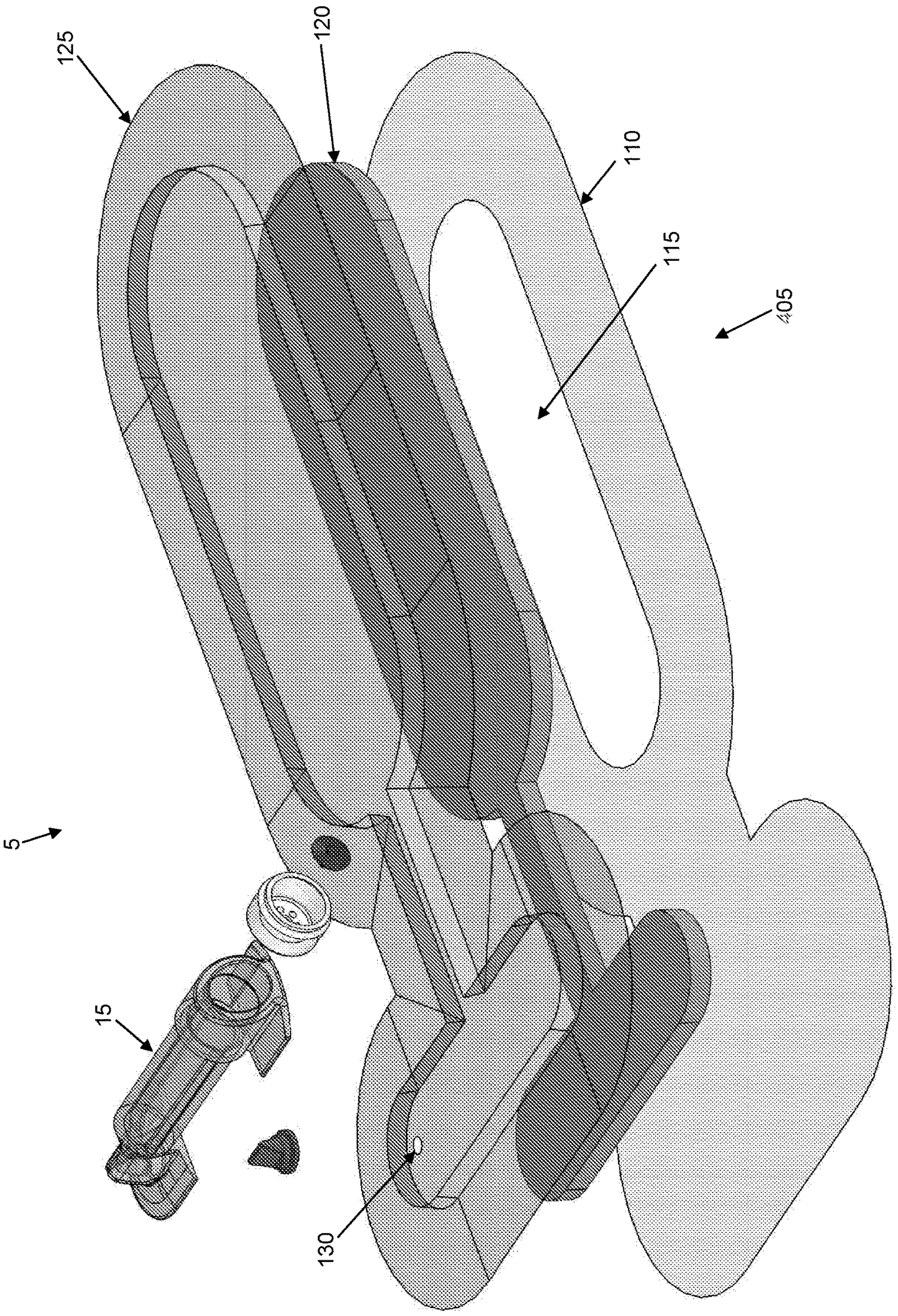
Figure 48:
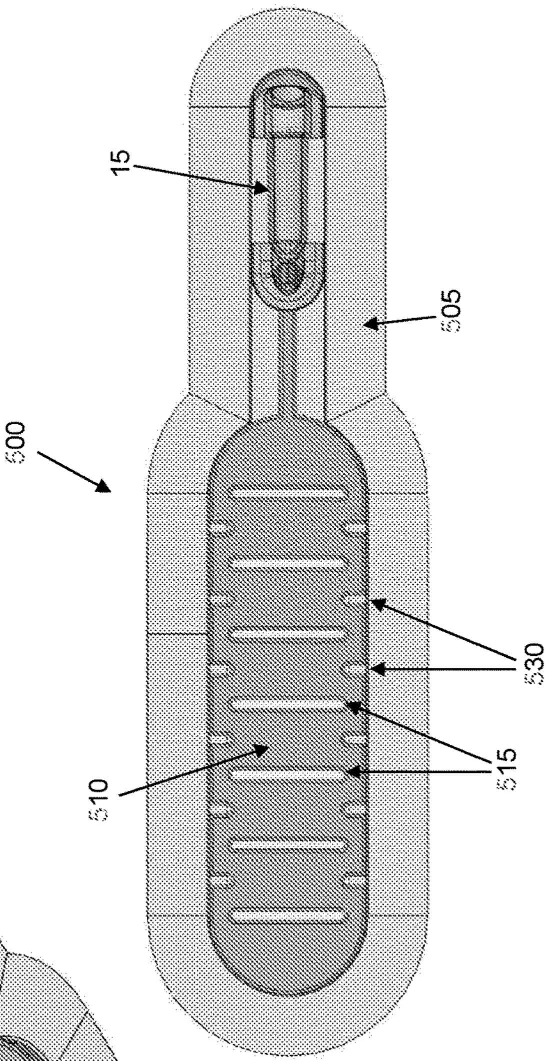
FIGS. 47, 48 and 49 are schematic views showing another new and improved NPWT bandage formed in accordance with the present invention, wherein the bandage comprises a transparent top layer which captures a layer of foam against the wound, wherein the foam layer is provided with a series of windows which (i) allow direct visualization of the wound, and (ii) provide a metric along the length of the bandage to indicate whether the bandage needs to be replaced, and further wherein the foam layer also comprises perimeter serrations which allow the bandage to conform to a curved wound—in this form of the invention, the NPWT bandage comprises an on-board pump which is laterally offset from the wound.
Figure 47:
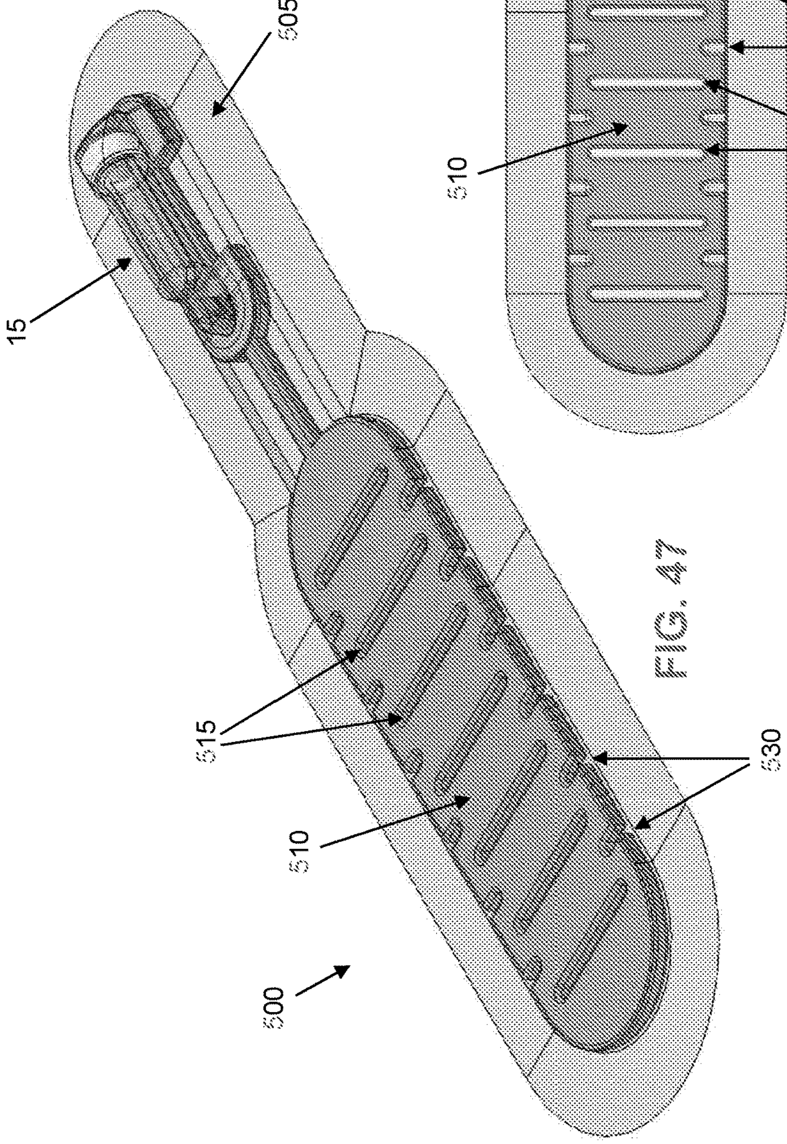
Figure 49:
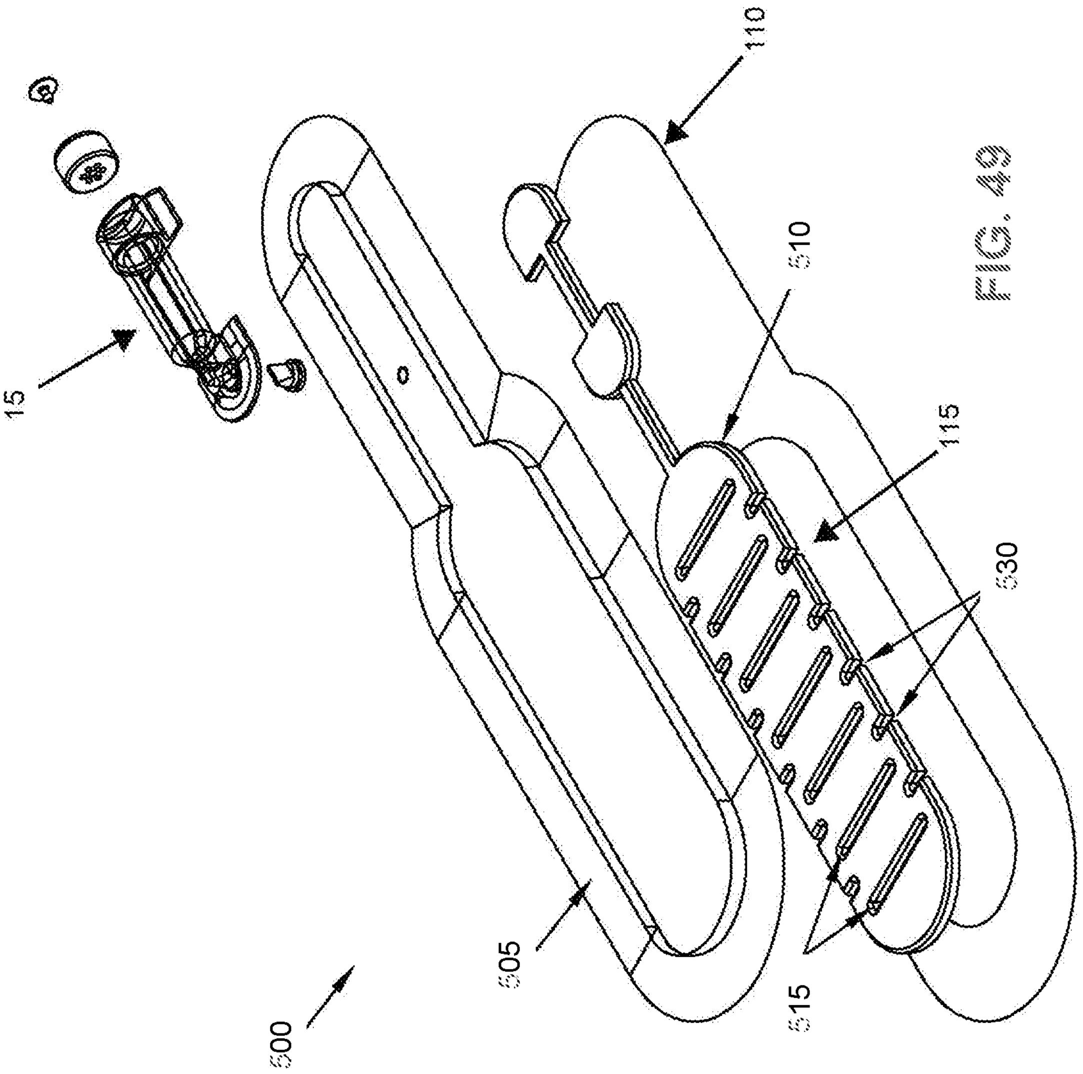
Figure 50:
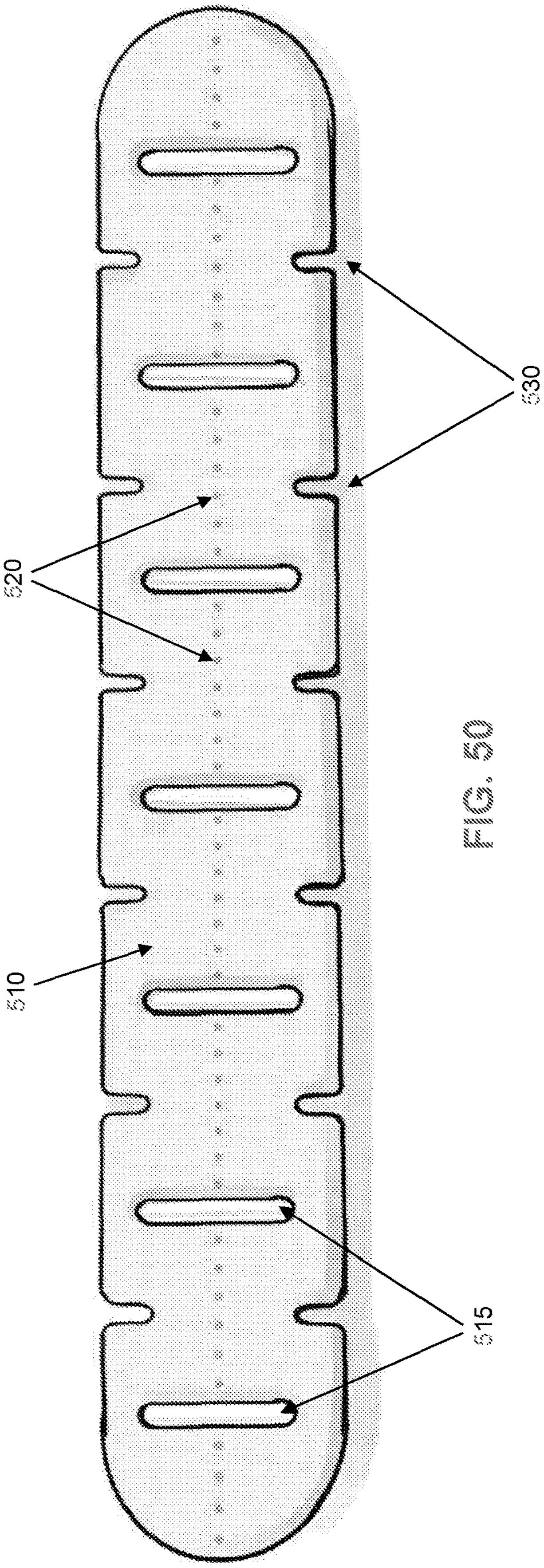
FIG. 50 is a schematic view showing further details of the foam layer of FIGS. 47, 48 and 49.

In one form of the invention, and as shown in FIGS. 47, 48 and 49, bandage 500 is preferably a negative pressure wound therapy (NPWT) bandage with an on-board pump assembly 15, with pump assembly 15 being laterally offset from bandage 500 in this configuration, which configuration is substantially the same configuration of the NPWT bandage shown in FIGS. 35-37. However, if desired, the aforementioned transparent upper layer 505, windows 515, markings 520 and perimeter serrations 530 may be provided with other NPWT bandages having a laterally offset pump assembly, e.g., such as the NPWT bandage shown in FIGS. 39-42, and/or the NPWT bandage shown in FIGS. 43-46.

Figure 57:
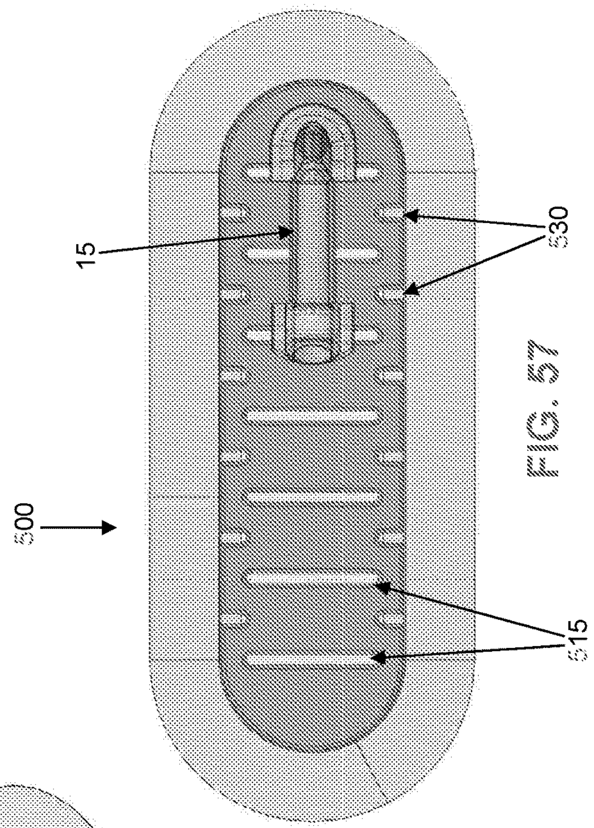
FIGS. 56 and 57 are schematic views showing how the NPWT bandage of FIGS. 47, 48 and 49 may be modified so as to position the on-board pump over a portion of the foam.
Figure 56:
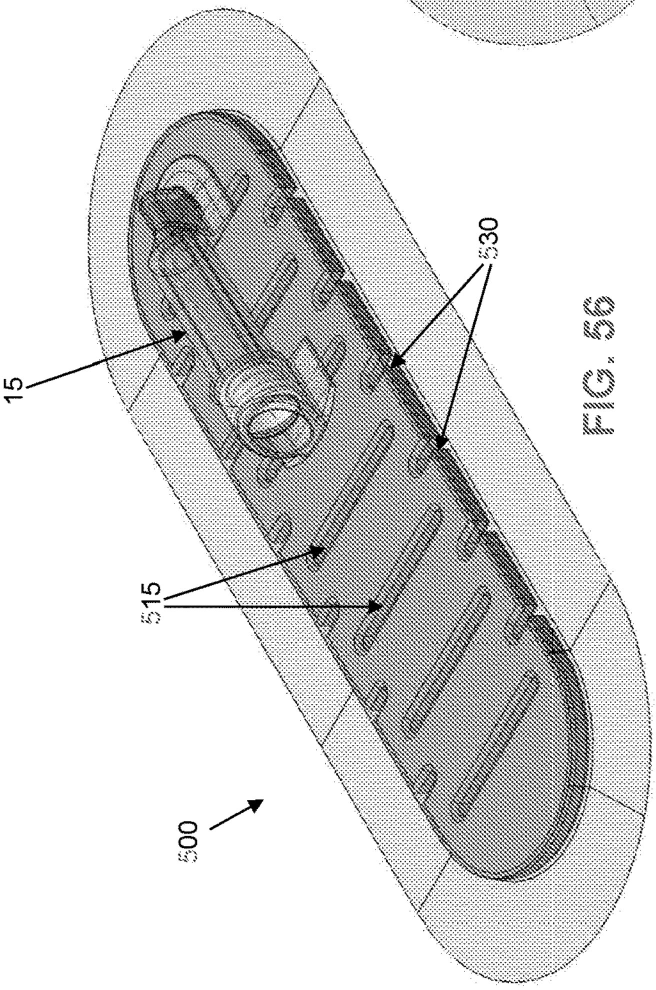

In another form of the invention, and as shown in FIGS. 56 and 57, bandage 500 is a negative pressure wound therapy (NPWT) bandage with an on-board pump assembly 15, with pump assembly 15 being positioned over a portion of upper layer 505 and foam layer 510.

In still another form of the invention, bandage 500 is configured to connect to a pump located remote from the bandage, or to another source of suction (e.g., wall suction).

Figure 59:
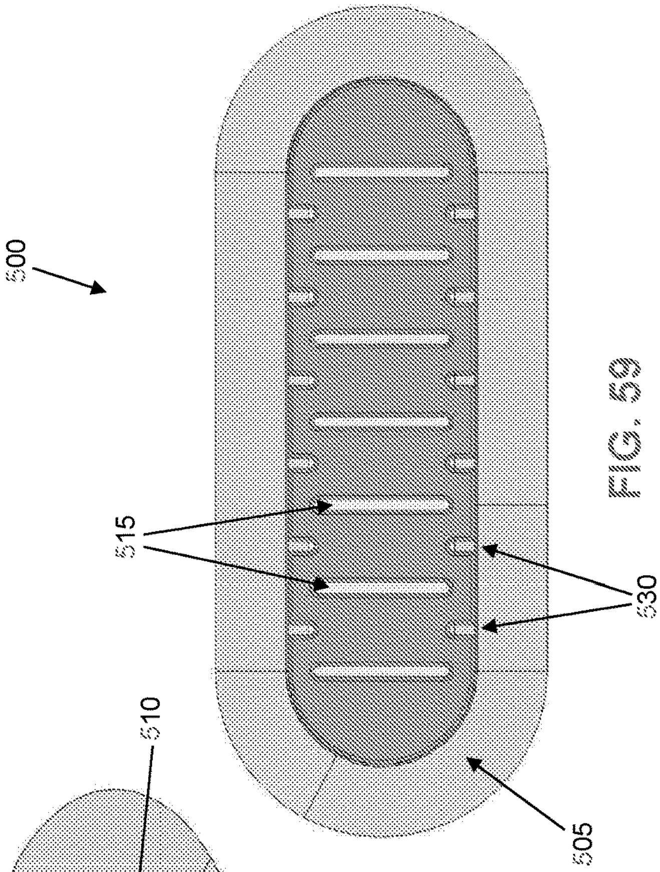
FIGS. 58, 59 and 60 are schematic views showing how the NPWT bandage of FIGS. 56 and 57 may be modified to remove the on-board pump, whereby to provide a general purpose bandage which comprises a transparent top layer which captures a layer of foam against the wound, wherein the foam layer is provided with a series of windows which (i) allow direct visualization of the wound, and (ii) provide a metric along the length of the bandage to indicate whether the bandage needs to be replaced, and further wherein the foam layer also comprises perimeter serrations which allow the bandage to conform to a curved wound.
Figure 58:
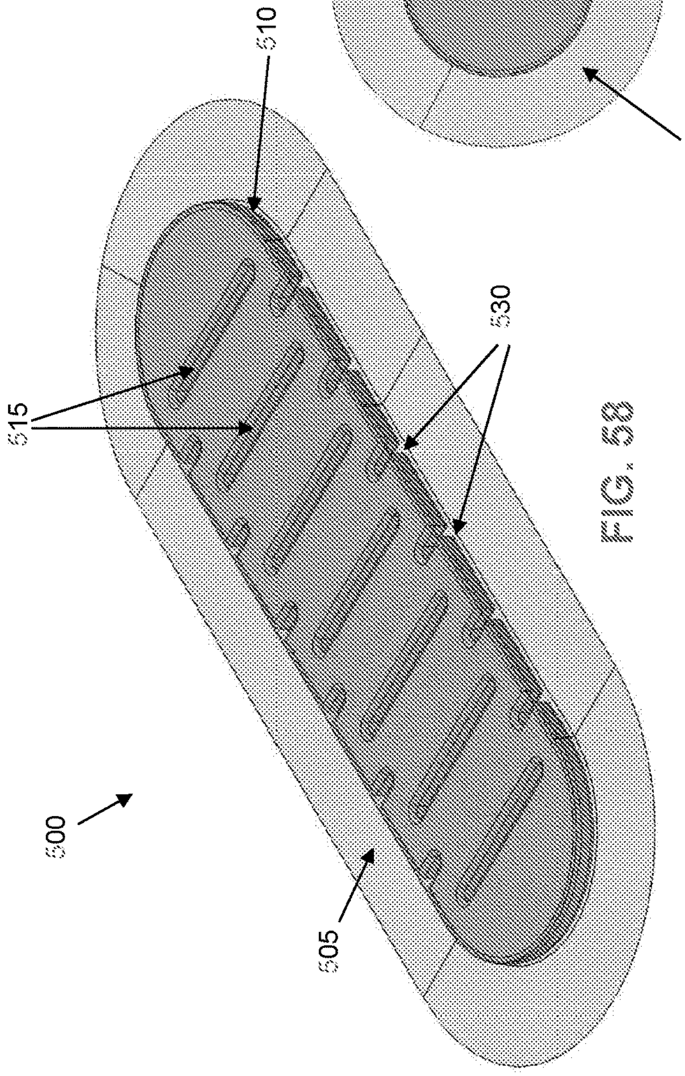

The novel bandage may also be used without applying negative pressure to the wound. By way of example but not limitation, and as shown in FIGS. 58 and 59, bandage 500 may omit an on-board pump and/or omit connection to a pump located remote from the bandage, or to another source of suction (e.g., wall suction). In this form of the invention, bandage 500 can essentially be used as a general purpose bandage.

Figure 60:
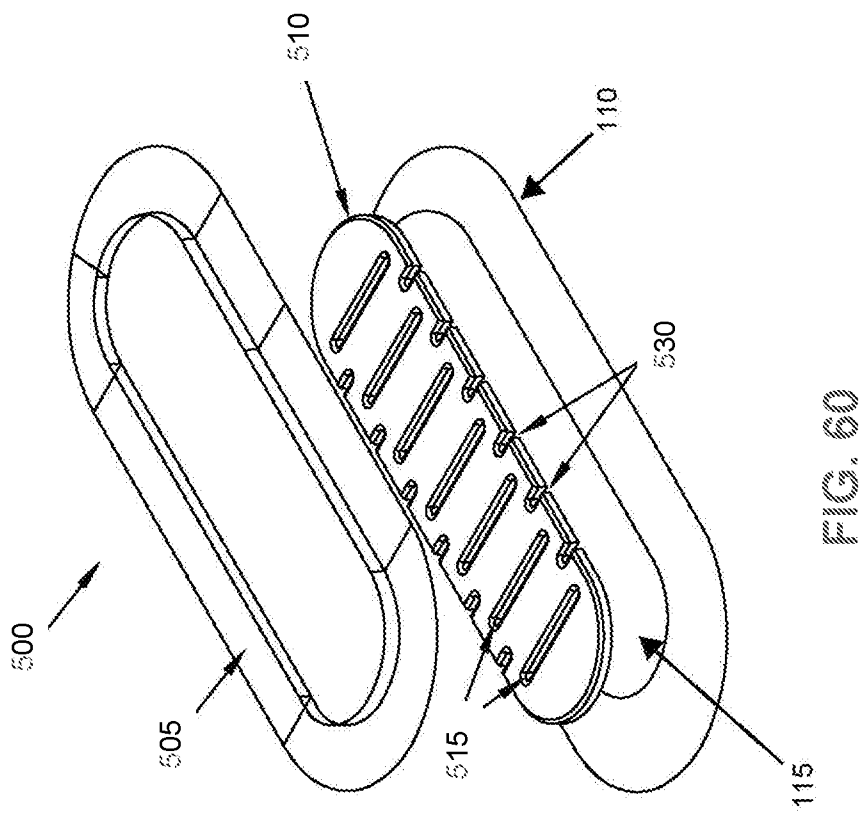

In other forms of the invention, lower skin-contacting polyurethane layer 110 of bandage 500 may be omitted, and upper layer 505 may be provided with (i) an adhesive for mounting foam layer 510 to upper layer 505, and (ii) an adhesive for adhering upper layer 505 to the skin of a patient. By way of example but not limitation, the construction of FIGS. 47-55 may omit lower skin-contacting polyurethane layer 110 of bandage 500, or the construction of FIGS. 56 and 57 may omit lower skin-contacting polyurethane layer 110 of bandage 500, or the construction of FIGS. 58, 59 and 60 may omit lower skin-contacting polyurethane layer 110 of bandage 500.

Furthermore, it should be noted that lower skin-contacting polyurethane layer 110 may also be omitted from any of the NPWT bandages shown in FIGS. 21-46, with upper polyurethane layer 125 being provided with (i) an adhesive for mounting intermediate foam layer 120 to upper polyurethane layer 125, and (ii) an adhesive for adhering upper polyurethane layer 125 to the skin of a patient.

If desired, notches 105 formed in pump body 60 of the pump assembly shown in FIGS. 17-20 and/or notches 105 formed in pump body 60 of the pump assembly shown in FIGS. 26-28 may also be formed into the respective pump bodies of the bandage 500 shown in FIGS. 47-49 and the bandage 500 shown in FIGS. 56 and 57. Furthermore, if desired, canister 200 may be used with the pump assemblies of the bandage 500 shown in FIGS. 47-49 and the bandage 500 shown in FIGS. 56 and 57. And, if desired, luer lock 300 may be used with the pump assemblies of the bandage 500 shown in FIGS. 47-49 and the bandage 500 shown in FIGS. 56 and 57.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A negative pressure wound therapy (NPWT) bandage for applying negative pressure to a wound, the NPWT bandage comprising:

a membrane configured for disposition over a wound so as to form a wound chamber between the membrane and the wound, the membrane comprising a wound-side surface, an atmosphere-side surface, and an opening extending through the membrane from the wound-side surface to the atmosphere-side surface;

a pump assembly mounted to the membrane by a pair of pedestals, the pump assembly comprising:

a pump body comprising a wall structure disposed about a pump chamber, wherein at least a portion of the wall structure is resilient;

a wound-side passageway extending through the wall structure and communicating with the wound chamber through the opening in the membrane; and an atmosphere-side passageway extending through the wall structure and connecting the pump chamber to the atmosphere;

wherein when the negative air pressure within the wound chamber is below a predetermined threshold, the pump body is in an expanded configuration, and when the negative air pressure within the wound chamber is above the predetermined threshold, the pump body is in fully collapsed configuration; and a suction source configured to be (i) connected to the pump assembly to increase the negative air pressure in the wound chamber of the pump body when the pump body is in the expanded configuration, and (ii) automatically and operatively disconnected from the pump assembly when the negative air pressure in the wound chamber exceeds the predetermined threshold and causes the pump body to automatically transition from the expanded configuration to the fully collapsed configuration, wherein the pump body comprises a plurality of notches formed in the wall structure of the pump body as interrupted notches separated by full-thickness wall portions, wherein each full-thickness wall portion is disposed between two adjacent interrupted notches, and wherein, when the pump body transitions from the expanded configuration to the fully collapsed configuration, at least two of the full-thickness wall portions of the wall structure of the pump body move radially inwardly to engage each other to automatically seal the pump chamber and prevent the suction source from increasing the negative air pressure in the wound chamber.

2. The NPWT bandage of claim 1, wherein the predetermined threshold is between 60 mm Hg and 180 mm Hg.

3. The NPWT bandage of claim 1, wherein when the negative pressure within the wound chamber is falling, but has not fallen enough to go below the predetermined threshold and cause a transformation of the pump body into the expanded configuration, the full-thickness wall portions of the wall structure of the pump body bow inwardly.

4. The NPWT bandage of claim 1, wherein the pump body is suspended between the pair of pedestals and spaced from the membrane.

5. The NPWT bandage of claim 1: wherein the pump body has a substantially circular cross-section;

wherein the pump body is mounted to the membrane by the pair of pedestals joined to the pump body at the "6 o'clock position", with the pump body being suspended between the pair of pedestals and spaced from the membrane;

wherein notches are formed in the wall structure of the pump body at the "9 o'clock position" and the "3 o'clock position";

wherein, when the pump body is in the fully collapsed configuration, the side walls of the wall structure of the pump body bow inwardly at the "9 o'clock position" and the "3 o'clock position"; and wherein, when the negative pressure within the wound chamber is falling, but has not fallen enough to go below the predetermined threshold and cause a transformation of the pump body into the fully expanded configuration, top and bottom walls of the wall structure of the pump body bow inwardly at the "12 o'clock position" and the "6 o'clock position".

6. The NPWT bandage of claim 1, wherein the pump assembly further comprises a removable cap for fluidically sealing the atmosphere-side passageway of the pump assembly when the suction source has been disconnected from the pump assembly.

7. The NPWT bandage of claim 1, wherein the suction source is fluidically connected to the atmosphere-side passageway of the pump assembly with a Luer lock.

8. The NPWT bandage of claim 1, wherein the pump body comprises a substantially cylindrical configuration.

9. The NPWT bandage of claim 8, wherein when the pump body is in the expanded configuration, the pump body comprises a substantially circular cross-section.

10. The NPWT bandage of claim 8, wherein when the pump body is in the fully collapsed configuration, the wall structure of the pump body bows inwardly.

11. The NPWT bandage of claim 1 wherein the wall structure of the pump body bows inwardly to seal the pump chamber when the pump body is in the fully collapsed configuration.

12. A negative pressure wound therapy (NPWT) bandage for applying negative pressure to a wound, the NPWT bandage comprising:

a membrane configured for disposition over a wound so as to form a wound chamber between the membrane and the wound, wherein the membrane comprises a wound-side surface, an atmosphere-side surface, and an opening extending through the membrane from the wound-side surface to the atmosphere-side surface;

a pump assembly carried by the membrane, the pump assembly comprising:

a pump body comprising a wall structure disposed about a pump chamber, wherein at least a portion of the wall structure is resilient, a wound-side passageway extending through the wall structure and communicating with the wound chamber through the opening in the membrane, and an atmosphere-side passageway extending through the wall structure and connecting the pump chamber to an external atmosphere; and a suction source configured to be connected to the pump assembly for establishing negative air pressure within the wound chamber, wherein when the negative air pressure within the wound chamber is below a predetermined threshold, the pump body is automatically in an expanded configuration, and when the negative air pressure within the wound chamber is above the predetermined threshold, the pump body is automatically in a fully collapsed configuration, wherein, when the pump body is in the expanded configuration, the suction source increases the negative air pressure within the wound chamber, wherein the pump body is configured to automatically transition from the expanded configuration to the fully collapsed configuration so as to operatively disconnect the pump assembly from the suction source when the negative air pressure within the wound chamber exceeds the predetermined threshold, wherein the pump body has a substantially circular cross-section and is mounted to the membrane by a pair of pedestals joined to the pump body at the "6 o'clock position," with the pump body being suspended between the pair of pedestals and spaced from the membrane, wherein the pump body comprises a plurality of notches formed in the wall structure at the "9 o'clock position" and the "3 o'clock position," the plurality of notches comprising two interrupted notches separated by a full-thickness wall portion at the "9 o'clock position" and two interrupted notches separated by a full-thickness wall portion at the "3 o'clock position", and wherein, when the pump body is in the fully collapsed configuration, diametrically-opposing portions of the wall structure of the pump body bow inwardly into engagement with each other to automatically seal the pump chamber and prevent the suction source from increasing the negative air pressure in the wound chamber.

13. A negative pressure wound therapy (NPWT) bandage for applying negative pressure to a wound, the NPWT bandage comprising:

a membrane configured for disposition over a wound so as to form a wound chamber between the membrane and the wound, the membrane comprising a wound-side surface, an atmosphere-side surface, and an opening extending through the membrane from the wound-side surface to the atmosphere-side surface;

a pump assembly carried by the membrane, the pump assembly comprising:

a pump body comprising a wall structure disposed about a pump chamber, wherein at least a portion of the wall structure is resilient;

a wound-side passageway extending through the wall structure and communicating with the wound chamber through the opening in the membrane; and an atmosphere-side passageway extending through the wall structure and connecting the pump chamber to the atmosphere; and a suction source configured to be connected to the pump assembly for establishing negative air pressure within the wound chamber, wherein when the negative air pressure within the wound chamber is below a predetermined threshold, the pump body is automatically in fully expanded configuration, and when the negative air pressure within the wound chamber is above the predetermined threshold, the pump body is automatically in a fully collapsed configuration, wherein, when the pump body is in the expanded configuration, the suction source increases the negative air pressure within the wound chamber, wherein the pump body is configured to automatically transition from the expanded configuration to the fully collapsed configuration so as to operatively disconnect the pump assembly from the suction source when the negative air pressure within the wound chamber exceeds the predetermined threshold, wherein the pump body comprises a plurality of notches formed in the wall structure of the pump body as interrupted notches separated by full-thickness wall portions, wherein each full-thickness wall portion is disposed between two adjacent interrupted notches, and wherein, when the pump body transitions from the expanded to the fully collapsed configuration, at least two of the full-thickness wall portions of the wall structure of the pump body move radially inwardly to engage one another and automatically seal the pump chamber, thereby preventing the suction source from further increasing the negative pressure within the wound chamber.

14. A negative pressure wound therapy (NPWT) bandage for applying negative pressure to a wound, the NPWT bandage comprising:

a membrane configured for disposition over a wound so as to form a wound chamber between the membrane and the wound, the membrane comprising a wound-side surface, an atmosphere-side surface, and an opening extending through the membrane from the wound-side surface to the atmosphere-side surface;

a pump assembly carried by the membrane, the pump assembly comprising:

a pump body comprising a wall structure disposed about a pump chamber, wherein at least a portion of the wall structure is resilient, a wound-side passageway extending through the wall structure and communicating with the wound chamber through the opening in the membrane, and an atmosphere-side passageway extending through the wall structure and connecting the pump chamber to the atmosphere, wherein when the negative air pressure within the wound chamber is below a predetermined threshold, the pump body is automatically in an expanded configuration, and when the negative air pressure within the wound chamber is above the predetermined threshold, the pump body is automatically in a fully collapsed configuration; and a suction source configured to be (i) connected to the pump assembly to increase the negative air pressure in the wound chamber of the pump body when the pump body is in the expanded configuration, and (ii) automatically and operatively disconnected from the pump assembly when the negative air pressure in the wound chamber exceeds the predetermined threshold causing the pump body automatically transitions from the expanded configuration to the fully collapsed configuration, wherein the pump body has a substantially circular cross-section, wherein the pump body is mounted to the membrane by a pair of pedestals joined to the pump body at the "6 o'clock position", with the pump body being suspended between the pair of pedestals and spaced from the membrane, wherein the pump body comprises a plurality of notches formed in the wall structure of the pump body at the "9 o'clock position" and the "3 o'clock position", wherein the plurality of notches comprises two interrupted notches separated by a full-thickness wall portion at the "9 o'clock position" and two interrupted notches separated by a full-thickness wall portion at the "3 o'clock position", wherein, when the pump body is in the fully collapsed configuration, the side walls of the wall structure of the pump body bow inwardly at the "9 o'clock position" and the "3 o'clock position", and wherein, when the negative pressure within the wound chamber is above the predetermined threshold and the pump body is in the fully collapsed configuration, respective full-thickness wall portions of the wall structure of the pump body bow inwardly to engage each other and automatically seal the pump chamber, thereby preventing the suction source from further increasing the negative pressure in the wound chamber.

15. The NPWT bandage of claim 13, wherein the plurality of notches comprises a first notch and a second notch that are diametrically opposed to each other such that the full-thickness wall portion of the first notch contacts the full-thickness wall portion of the second notch when the pump body is in the fully collapsed configuration.

16. The NPWT bandage of claim 15, wherein the first notch is at 3 o'clock and the second notch is at 9 o'clock around a circumference of the wall structure.

* * * * *